(12) United States Patent
Svenstrup et al.

(10) Patent No.: US 9,533,992 B2
(45) Date of Patent: Jan. 3, 2017

(54) PDE9 INHIBITORS WITH IMIDAZO TRIAZINONE BACKBONE

(71) Applicant: H. Lundbeck A/S, Valby (DK)

(72) Inventors: Niels Svenstrup, København V (DK); Klaus Bæk Simonsen, Odense M (DK); Lars Kyhn Rasmussen, Vanløse (DK); Karsten Juhl, Greve (DK); Morten Langgård, Glostrup (DK); Kate Wen, Shanghai (CN); Yazhou Wang, Shanghai (CN)

( * ) Notice: Subject to any disclaimer, the term of this patent is extended or adjusted under 35 U.S.C. 154(b) by 0 days.

(21) Appl. No.: 15/089,819

(22) Filed: Apr. 4, 2016

(65) Prior Publication Data
US 2016/0213674 A1    Jul. 28, 2016

Related U.S. Application Data

(62) Division of application No. 14/374,278, filed as application No. PCT/EP2013/051451 on Jan. 25, 2013.

(30) Foreign Application Priority Data

Jan. 26, 2012  (WO) ............... PCT/CN2012/070718
Aug. 16, 2012  (WO) ............... PCT/CN2012/080208

(51) Int. Cl.
  *C07D 487/04*    (2006.01)
  *A61K 31/53*    (2006.01)
(52) U.S. Cl.
  CPC ............. *C07D 487/04* (2013.01); *A61K 31/53* (2013.01)
(58) Field of Classification Search
  CPC .............................. C07D 487/04; A61K 31/53
  See application file for complete search history.

(56) References Cited

U.S. PATENT DOCUMENTS

| 2004/0220186 A1 | 11/2004 | Bell et al. |
| 2015/0045348 A1 | 2/2015 | Svenstrup et al. |

FOREIGN PATENT DOCUMENTS

| CA | 2296224 | 7/2000 | |
| CN | 1344268 | 4/2002 | |
| CN | 101448829 | 6/2009 | |
| WO | WO 99/24433 | 5/1999 | |
| WO | WO 03/037432 | 5/2003 | |
| WO | WO 03/037899 | 5/2003 | |
| WO | WO 03/093270 | 11/2003 | |
| WO | WO 2004/096811 | 11/2004 | |
| WO | WO 2005/041972 | 5/2005 | |
| WO | WO 2007/137819 | 12/2007 | |
| WO | WO 2008/139293 | 11/2008 | |
| WO | WO 2010/084438 | 7/2010 | |
| WO | WO 2012/040230 | 3/2012 | |
| WO | WO 2012040230 A1 * | 3/2012 | ........... C07D 487/04 |
| WO | WO 2012/110441 | 8/2012 | |

OTHER PUBLICATIONS

Blokland, A. et al., (2006) "Improving Memory: A Role for Phosphodiesterases," Curr. Pharm. Des. 12(20):2511-2523.
Breer, H. et al., (1990) "Rapid Kinetics of Second Messenger Formation in Olfactory Transduction," Nature 345(6270):65-68.
Cooke, S.F. et al., (2006) "Plasticity in the Human Central Nervous System," Brain 129(7):1659-1673.
Fisher, D.A. et al., (1998) "Isolation and Characterization of PDE9A, a Novel Human cGMP-specificific Phosphodiesterase," J. Biol. Chem. 273(25):15559-15564.
Josef van der Staay, F. et al., (2008) "The Novel Selective PDE9 Inhibitor BAY 73-6691 Improved Learning and Memory in Rodents," Neuropharma. 55(5):908-918.
Mehats, C. et al., (2002) "Cyclic Nucleotide Phosphodiesterases and Their Role in Endocrine Cell Signaling," TRENDS Endocrinol. & Metab. 13:29-35.
Wunder, F. et al., (2005) "Characterization of the First Potent and Selective PDE9 Inhibitor Using a cGMP Reporter Cell Line," Mol. Pharmacol. 68(6):1775-1781.
Zhou, M. et al., (1994) "Role of Guanylyl Cyclase and cGMP-dependent Protein Kinase in Long-term Potentiation," Nature 368(6472):635-639.
International Search Report and Written Opinion issued Sep. 13, 2012 in International Application No. PCT/CN2012/070718 filed Jan. 26, 2012.
International Search issued Feb. 26, 2013 in International Application No. PCT/EP2013/051451 filed Jan. 25, 2013 (4 pages).
International Written Opinion issued Feb. 26, 2013 in International Application No. PCT/EP2013/051451 filed Jan. 25, 2013 (5 pages).

* cited by examiner

*Primary Examiner* — Matthew Coughlin
(74) *Attorney, Agent, or Firm* — DT Ward, PC; Donna T. Ward; Heng Zhu

(57) ABSTRACT

This invention is directed to compounds, which are PDE9 enzyme inhibitors. The invention provides a pharmaceutical composition comprising a therapeutically effective amount of a compound of the invention and a pharmaceutically acceptable carrier. The present invention also provides processes for the preparation of the compounds of formula (I). The present invention further provides a method of treating a subject suffering from a neurodegenerative disorder comprising administering to the subject a therapeutically effective amount of a compound of formula (I). The present invention further provides a compound of formula (I) for use in a method of treating a subject suffering from a psychiatric disorder comprising administering to the subject a therapeutically effective amount of a compound of formula (I).

9 Claims, No Drawings

PDE9 INHIBITORS WITH IMIDAZO TRIAZINONE BACKBONE

CROSS-REFERENCE TO RELATED APPLICATIONS

The present application is a divisional application of U.S. Ser. No. 14/374,278 (filed Jul. 24, 2014, pending), which application is a 371 of PCT Appln. No. PCT/EP2013/051451 (filed Jan. 25, 2013, now lapsed), which claims priority to PCT Applns. No. PCT/CN2012/080208 (filed Aug. 16, 2012, now lapsed) and PCT/CN2012/070718 (filed Jan. 26, 2012, now lapsed).

FIELD OF THE INVENTION

The present invention relates to cyclic guanylate monophosphate (cGMP)-specific phosphodiesterase type 9 inhibitors (hereinafter referred to as PDE9 inhibitors) of the form 3H-imidazo[5,1-f][1,2,4]triazin-4-ones for the use as a medicament. Moreover the invention relates to a pharmaceutical composition comprising 3H-imidazo[5,1-f][1,2,4]triazin-4-ones, as well as a process for preparation of the compounds.

BACKGROUND OF THE INVENTION

The phosphodiesterases (PDEs) are a superfamily of enzymes that metabolically inactivate the ubiquitous intracellular messengers cAMP and cGMP. This function involves the PDEs in a broad range of important cellular functions, such as immune response, memory, and vision. The human genome encodes for 21 PDEs that are categorized into 11 families (Mehats C, Andersen C B, Filopanti M, Jin S L, Conti M. "Cyclic nucleotide phosphodiesterases and their role in endocrine cell signaling." Trends Endocrinol Metab. 2002; 13:29-35). These enzymes share a conserved catalytic domain of approximately 300 amino acids that is located in the C-terminal region of the protein. The N-terminal regions, which vary among different PDEs, serve regulatory functions including autoinhibition of the catalytic domains or control of subcellular localization (Mehats 2002). The PDEs have different substrate preferences: Cyclic guanylate monophosphate (cGMP)-specific phosphodiesterase type 9 (PDE9) is a member of the PDE enzyme family that selectively hydrolyses cGMP over cAMP (D A Fisher et al., J. Biol. Chemistry, vol. 273, No. 25, 15559-15564 (1998)). The different substrate preferences, combined with different expression profiles, cellular compartmentalization, and regulation, allow the PDEs to play a very versatile role in cell signal transduction (Breer H, Boekhoff I, Tareilus E. "Rapid kinetics of second messenger formation in olfactory transduction." Nature. 1990; 345:65-68).

PDE9 inhibitors have been reported as useful to treat cardiovascular disorders (WO 03/037899), and insulin resistance syndrome, hypertension, and/or type 2 diabetes (WO 03/037 432) as well as for treatment of obesity related conditions (WO 2005/041972).

Wunder F. et al (Mol. Pharmacol. 2005 December; 68(6): 1775-81, 2005) report the in vitro characterization of 1-(2-chlorophenyi)-6-[(2R)-3,3,3-trifluoro-2-methylpropyl]-1,5-dihydro-4H-pyrazolo[3,4-d]pyrimidine-4-one, a selective inhibitor of phosphodiesterase 9 (PDE9), which is under development for the treatment of Alzheimer's disease. This compound is reported to inhibit human ($IC_{50=55}$ nM) and murine ($IC_{50=100}$ nM) PDE9 activity in vitro.

Over the years, convincing experimental evidence has accumulated supporting the cognition-enhancing properties of several classes of POE-inhibitors (Biokland et al., 2006: "Improving memory; a role for phosphordiesterases", Current Pharmacological Design 12, 2511-2523).

In a later study, van der Staay et al. (F. Josef van der Staay, Neuropharmacology Volume 55, Issue 5, October 2008, pages 908-918) concludes that the PDE9 inhibitor 1-(2-chlorophenyl)-6-[(2R)-3,3,3-trifluoro-2-methylpropyl]-1,5-dihydro-4H-pyrazolo[3,4-d]pyrimidine-4-one may act as a putative cognition enhancer.

WO 2012/040230 (Envivo Pharmaceuticals, Inc) is directed to imidazotriazinone compounds which are claimed to be inhibitors of phosphordiesterease 9.

Alzheimers disease is the most common form of dementia, it is incurable, degenerative, and terminal. The typical symptoms are cognitive difficulties, difficulties with executive functioning (such as planning, organization, mental flexibility and task coordination) as well as with perception (agnosia) and execution of movements (apraxia).

Because AD cannot be cured and is degenerative, palliative treatment of patients is essential.

SUMMARY OF THE INVENTION

The present invention discloses novel PDE9 inhibitors for the use as a medicament, such as in the treatment of patients suffering from cognitive impairments, in particular cognitive impairments that relate to neurodegenerative diseases such as cortical dementia (e.g. Alzheimer's disease) or subcortical dementia, e.g. AIDS related dementia.

The PDE9 inhibitors of the present invention have the structure I (i.e. a 3H-imidazo[5,1-f][1,2,4]triazin-4-one backbone):

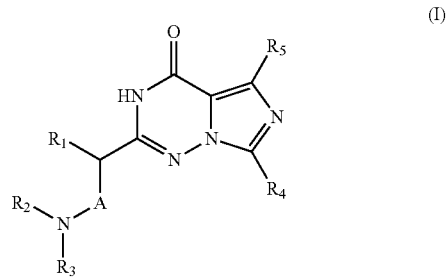

(I)

wherein R2 is cyclized with either R1 or R3.

The invention relates to methods of improving conditions involving PDE9, such as cognition, in particular the invention relates to a method of treating diseases involving cognitive difficulties, difficulties with executive functioning (such as planning, organization, mental flexibility and task coordination) as well as with pereception (agnosia). The methods of improving conditions involving PDE9 and/or treating diseases involving PDE9 comprises the administration of a compound of the present invention or a pharmaceutically acceptable salt, solvate or prodrug thereof to a patient in need thereof. The compound of the present invention or a pharmaceutically acceptable salt, solvate or prodrug thereof may be in the form of a pharmaceutical composition.

In a further aspect the invention relates to an improved pharmaceutical composition comprising a compound of the present invention particularly useful for the treatment of cognitive difficulties, difficulties with executive functioning (such as planning, organization, mental flexibility and task coordination) as well as with pereception (agnosia), in particular when associated neurodegenerative diseases, such as cortical or subcortical dementias, e.g. Alzheimer's disease (AD).

DETAILED DESCRIPTION OF THE INVENTION

Cognitive impairment includes a decline in cognitive functions or cognitive domains, such as, e.g., difficulties with attention, learning, memory and executive function (relevant reactions to external stimuli). Cognitive impairment also may include: deficits in attention, disorganized thinking, slow thinking, difficulty in understanding, poor concentration, impairment of problem solving, poor memory, difficulty in expressing thoughts and/or integrating thoughts, feelings and behaviour, and/or extinction of irrelevant thoughts, and difficulty in attention and vigilance, verbal learning and memory, visual learning and memory, speed of processing, social cognition, reasoning and problem solving, e.g., executive functioning. There are presently no effective drugs for the treatment of cognitive disorders on the market and there is a great need and demand for drugs effective in the treatment of such disorders.

Without being limited to any specific theory it is believed that the mode of action of PDE9 inhibitors can be understood in the light of the following neurological processes: guanylyl cyclase (alt. guanylate cyclase) converts guanosine triphosphate (GTP) to cyclic guanosine monophosphate (cGMP), which in turn activates cGMP-dependent protein kinase G (PKG). PKG is known to lower the threshold for the induction of long-term potentiation (LTP), i.e. the long-lasting improvement in communication between neurons (Zhou et al., 1994: "Role of guanylyl cyclase and cGMP-dependent protein kinase in long-term potentiation", Nature 368, 635-639). The communication between neurons takes place via the chemical synapses (synaptic transmission) and because memories are believed to be stored within these synapses, LTP is considered one of major cellular mechanisms that underlies cognition (Boron, W. F., 2005: Medical Physiology: A Cellular and Molecular Approach. Elsevier/Saunders, ISBN 1-4160-2328-3 and Cooke et al., 2006 "Plasticity in the human central nervous system". Brain 129, 1659-1673). As a result high levels of cGMP will eventually lead to improvement of cognition via the activation of PKG. The level of cGMP can be increased by inhibition of PDE9, which—as mentioned above—has the highest affinity for cGMP of any of the PDEs. Accordingly, PDE9 inhibitors will improve synaptic transmission and thereby enhance cognitive performance as evidenced by the results presented in the experimental section.

The invention will be illustrated in the following non-limiting examples.

EMBODIMENTS ACCORDING TO THE INVENTION

In a first embodiment (E1) the present invention relates to compounds having the structure (I) (also referred to as compounds of formula (I))

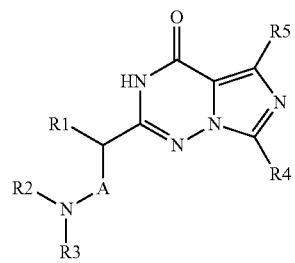

wherein R2 is cyclized with either R1 or R3,
wherein R1, R2 and R3 are
R1, when cyclized with R2, is

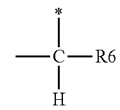

wherein R6 is selected from the group consisting of H, —CH$_3$, —C$_2$H$_5$, and —C$_3$H$_7$,
wherein * denotes the cyclization point, and
R1, when not cyclized, is selected from the group consisting of
H and

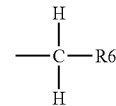

wherein R6 is selected from the group consisting of H, —CH$_3$, —C$_2$H$_5$, and —C$_3$H$_7$
R2 is a compound selected from the group consisting of

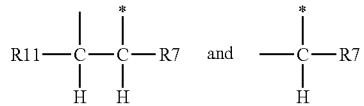

wherein R7 and R11 independently are selected from the group consisting of H, —CH$_3$, —C$_2$H$_5$, and —C$_3$H$_7$
wherein * denotes the cyclization point, and
R3, when cyclized with R2, is

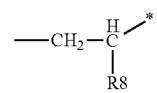

wherein * denotes the cyclization point, and
wherein R8 is selected from the group consisting of H, C$_1$-C$_6$ alkyl, branched C$_3$-C$_6$ alkyl, C$_3$-C$_6$ cycloalkyl, C$_6$-C$_{10}$ aryl, substituted C$_6$-C$_{10}$ aryl, C$_3$-C$_9$ heteroaryl, substituted C$_3$-C$_9$ heteroaryl, C$_1$-C$_6$ alkoxy, branched C$_3$-C$_6$ alkoxy, C$_3$-C$_6$ cycloalkoxy, C$_6$-C$_{10}$ aryloxy, substituted C$_6$-C$_{10}$ aryloxy, C$_3$-C$_9$ heteroaryloxy, substituted C$_3$-C$_9$ heteroaryloxy; and R3, when not cyclized, is $$\begin{array}{c} R9 \\ | \\ C \\ / \backslash \\ H \quad R10 \end{array}$$

wherein
R9 is selected from the group consisting of H, —CH$_3$, and —C$_2$H$_5$; and
R10 is selected from the group consisting of C$_6$-C$_{10}$ aryl, substituted C$_6$-C$_{10}$ aryl, C$_3$-C$_9$ heteroaryl, substituted C$_3$-C$_9$ heteroaryl
R4 is selected from the group consisting of C$_6$-C$_{10}$ aryl, substituted C$_6$-C$_{10}$ aryl, C$_3$-C$_9$ heteroaryl, substituted C$_3$-C$_9$ heteroaryl, C$_3$-C$_6$ heterocyclyl, substituted C$_3$-C$_6$ heterocyclyl, C$_3$-C$_6$ cycloalkyl, and substituted C$_3$-C$_6$ cycloalkyl;
R5 is selected from the group consisting of hydrogen, F, Cl, CN, —CH$_3$, —C$_2$H$_5$, —C$_3$H$_7$, and —CF$_3$;
A is absent or —CH$_2$—
and tautomers and pharmaceutically acceptable acid addition salts thereof, and polymorphic forms thereof, provided that the compound is not 2-[1-[(4-fluorophenyl)methyl]-4-methyl-pyrrolidin-3-yl]-7-tetrahydropyran-4-yl-3H-imidazo[5,1-f][1,2,4]triazin-4-one; 2-(1-benzyl-4-methyl-pyrrolidin-3-yl)-7-tetrahydropyran-4-yl-3H-imidazo[5,1-f][1,2,4]triazin-4-one; 2-[4-methyl-1-(pyrimidin-2-ylmethyl)pyrrolidin-3-yl]-7-tetrahydropyran-4-yl-3H-imidazo[5,1-f][1,2,4]triazin-4-one; 2-(4-methylpyrrolidin-3-yl)-7-tetrahydropyran-4-yl-3H-imidazo[5,1-f][1,2,4]triazin-4-one; 2-[1-[(6-methoxy-2-pyridyl)methyl]-4-methyl-pyrrolidin-3-yl]-7-tetrahydropyran-4-yl-3H-imidazo[5,1-f][1,2,4]triazin-4-one; 2-[(3S,4S)-1-benzyl-4-methyl-pyrrolidin-3-yl]-7-tetrahydropyran-4-yl-3H-imidazo[5,1-f][1,2,4]triazin-4-one; 2-[(3R,4R)-1-benzyl-4-methyl-pyrrolidin-3-yl]-7-tetrahydropyran-4-yl-3H-imidazo[5,1-f][1,2,4]triazin-4-one; 2-[(3S,4S)-4-methylpyrrolidin-3-yl]-7-tetrahydropyran-4-yl-3H-imidazo[5,1-f][1,2,4]triazin-4-one 2-[(3R,4R)-4-methylpyrrolidin-3-yl]-7-tetrahydropyran-4-yl-3H-imidazo[5,1-f][1,2,4]triazin-4-one; 2-[(3S,4S)-4-methyl-1-(pyrimidin-2-ylmethyl)pyrrolidin-3-yl]-7-tetrahydropyran-4-yl-3H-imidazo[5,1-f][1,2,4]triazin-4-one; 2-[(3R,4R)-4-methyl-1-(pyrimidin-2-ylmethyl)pyrrolidin-3-yl]-7-tetrahydropyran-4-yl-3H-imidazo[5,1-f][1,2,4]triazin-4-one; 4-[3-methyl-4-(4-oxo-7-tetrahydropyran-4-yl-3H-imidazo[5,1-f][1,2,4]triazin-2-yl)pyrrolidin-1-yl]benzonitrile; 2-[(3S,4S)-1-[(4-fluorophenyl)methyl]-4-methyl-pyrrolidin-3-yl]-7-tetrahydropyran-4-yl-3H-imidazo[5,1-f][1,2,4]triazin-4-one; 2-[(3R,4R)-1-[(4-fluorophenyl)methyl]-4-methyl-pyrrolidin-3-yl]-7-tetrahydropyran-4-yl-3H-imidazo[5,1-f][1,2,4]triazin-4-one or 2-[4-methyl-1-(pyrazin-2-ylmethyl)pyrrolidin-3-yl]-7-tetrahydropyran-4-yl-3H-imidazo[5,1-f][1,2,4]triazin-4-one.

In a further embodiment (E2) of (E1) the one or more heteroaryls of R4, R8 and R10 independently of each other comprise one or two nitrogen.

In a further embodiment (E3) of (E1) R8 is C$_1$-C$_3$ alkyl.

In a further embodiment (E4) of (E1) R8 is branched C$_1$-C$_3$ alkyl.

In a further embodiment (E5) of (E1) R8 is phenyl or napthyl.

In a further embodiment (E6) of (E1) R8 is substituted phenyl or substituted napthyl.

In a particular embodiment (E7) of any of embodiments (E1) and E(6) the substituent is selected from the group consisting of F, Cl, methyl, trifluoromethyl, methoxy, trifluoromethoxy, cyano, ethyl, dimethylamino, cyclopropyl, and isopropyl.

In a particular embodiment (E8) of (E7) the substituents are selected from the group consisting of F, Cl, methyl, trifluoromethyl, methoxy, trifluoromethoxy, cyano, ethyl, and dimethylamino.

In an embodiment (E9) of any of embodiments (E1) and (E2) R8 is a C$_4$-C$_9$ heteroaryl.

In a particular embodiment (E10) of embodiment (E9) R8 is selected from the group consisting of pyridyl, pyridazine, pyrimidinyl, pyrazinyl, quinolinyl, quinazolinyl, and quinoxalinyl.

In a further embodiment (E11) of any of embodiments (E1) and (E2) R8 is a substituted C$_4$-C$_9$ heteroaryl.

In a particular embodiment (E12) of embodiment (E11) R8 is selected from the group consisting of substituted pyridyl, substituted pyridazine, substituted pyrimidinyl, substituted pyrazinyl, substituted quinolinyl, and substituted quinazolinyl, and substituted quinoxalinyl.

In a particular embodiment (E13) of embodiment (E10) R8 is selected from the group consisting of 2-pyridyl, 3-pyridyl, 2-pyridazine, 2-pyrimidinyl, 4-pyrimidinyl, 2-pyrazinyl, 2-quinolinyl, 2-quinoxalinyl, 6-quinoxalinyl, and 2-quinazolinyl.

In a particular embodiment (E14) embodiment (E12) R8 is selected from the group consisting of substituted 2-pyridyl, substituted 3-pyridyl, substituted 2-pyridazine, substituted 2-pyrimidinyl, substituted 4-pyrimidinyl, substituted 2-pyrazinyl, substituted 2-quinolinyl, substituted 2-quinoxalinyl, substituted 6-quinoxalinyl, and substituted 2-quinazolinyl.

In a particular embodiment (E15) of any of embodiments (E1), (E2), (E11), (E12) and (E14) the substituent of R8 is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E16) of embodiment (E1) R8 is C$_1$-C$_4$ alkoxy.

In a particular embodiment (E17) of (E16) R8 is methoxy or ethoxy.

In an embodiment (E18) of embodiment (E1) R8 is branched C$_3$-C$_4$ alkoxy.

In a particular embodiment (E19) of (E18) R8 is isopropoxy or isobutoxy.

In an embodiment (E20) of (E1), when R8 is C$_6$-C$_{10}$ aryloxy, R8 is selected from the group consisting of phenyloxy and naphtyloxy.

In an embodiment (E21) of (E1), when R8 is substituted C$_6$-C$_{10}$ aryloxy, R8 is selected from the group consisting of substituted phenyloxy and substituted naphtyloxy.

In a particular embodiment (E22) of any of embodiments (E1) and (E21) the substituents of R8, when R8 is a substituted C$_6$-C$_{10}$ aryloxy, is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E23) of any of embodiments (E1) and (E2) R8 is a $C_4$-$C_9$ heteroaryloxy.

In an embodiment (E24) of embodiment (E23) R8 is selected from the group consisting of pyridineoxy, pyridazineoxy, pyrimidineoxy and quinoxalineoxy In an embodiment (E25) of any of embodiments (E1) and (E2) R8 is a substituted $C_4$-$C_9$ heteroaryloxy.

In an embodiment (E26) of embodiment (E25) R8 is selected from the group consisting of substituted pyridineoxy, pyridazineoxy, substituted pyrimidineoxy and quinoxalineoxy In an embodiment (E27) of any of embodiments (E1), (E2), (E25) and (E26) the substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E28) of embodiment (E1) R10 is a $C_6$-$C_{10}$ aryl selected from the group consisting of phenyl and naphthyl.

In a preferred embodiment (E29) of embodiment (E28) R10 is phenyl.

In an embodiment (E30) of embodiment (E1) R10 is a substituted $C_6$-$C_{10}$ aryl selected from the group consisting of substituted phenyl and substituted naphthyl.

In a preferred embodiment (E31) of embodiment (E28) R10 is substituted phenyl.

In an embodiment (E32) of any of embodiments (E1), E(30) and E(31) the substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E33) of any of embodiments (E1) and (E2) R10 is a $C_4$-$C_9$ heteroaryl.

In a particular embodiment (E34) of embodiment (E33) R10 is selected from the group consisting of pyridyl, pyridazine, pyrimidinyl, pyrazinyl, quinolinyl, quinazolinyl, and quinoxalinyl.

In a particular embodiment (E35) of embodiment (E34) R10 is selected from the group consisting of 2-pyridyl, 3-pyridyl, 2-pyridazine, 2-pyrimidinyl, 4-pyrimidinyl, 2-pyrazinyl, 2-quinolinyl, 2-quinoxalinyl, 6-quinoxalinyl, and 2-quinazolinyl.

In a further embodiment (E36) of any of embodiments (E1) and (E2) R10 is a substituted $C_4$-$C_9$ heteroaryl.

In a particular embodiment (E37) of embodiment (E36) R10 is selected from the group consisting of substituted pyridyl, substituted pyridazine, substituted pyrimidinyl, substituted pyrazinyl, substituted quinolinyl, and substituted quinazolinyl, and substituted quinoxalinyl.

In a particular embodiment (E38) of embodiment (E37) R10 is selected from the group consisting of substituted 2-pyridyl, substituted 3-pyridyl, substituted 2-pyridazine, substituted 2-pyrimidinyl, substituted 4-pyrimidinyl, substituted 2-pyrazinyl, substituted 2-quinolinyl, substituted 2-quinoxalinyl, substituted 6-quinoxalinyl, and substituted 2-quinazolinyl.

In a particular embodiment (E39) of any of embodiments (E1), (E2), (E36), (E37) and (E38) the substituent of R10 is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E40) of embodiment of embodiment (E1) R4 is selected from the group consisting of phenyl and naphthyl.

In an embodiment (E41) of embodiment (E1) R4 is substituted phenyl.

In an embodiment (E42) of embodiment (E41) the substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E43) of embodiment of embodiment (E1) R4 is pyridyl.

In an embodiment (E44) of embodiment (E1) R4 is substituted pyridyl.

In an embodiment (E45) of embodiment (E44) the substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E46) of embodiment (E1) R4 is selected from the group consisting of tetrahydropyranyl, tetrahydrofuranyl and piperidyl.

In an embodiment (E47) of embodiment (E1) R4 is selected from the group consisting of substituted tetrahydropyranyl, substituted tetrahydrofuranyl and substituted piperidyl.

In a particular embodiment (E48) of embodiment E(47) the substituent is selected from group consisting of F, Cl, methyl, cyano and methoxy.

In an embodiment (E49) of embodiment (E1) R4 is selected from the group consisting of cyclobutyl, cyclopentyl and cyclohexyl.

In a preferred embodiment (E50) of embodiment (E49) R4 is cyclopentyl or cyclohexyl.

In an embodiment (E51) of embodiment (E1) R4 is selected from the group consisting of substituted cyclobutyl, substituted cyclopentyl and substituted cyclohexyl.

In a preferred embodiment (E52) of embodiment (E51) R4 is substituted cyclopentyl or substituted cyclohexyl.

In an embodiment (E53) of any of embodiments (E51) and (E52) substituent is selected from the group consisting of F, Cl, methyl, trifluoromethyl, methoxy, trifluoromethoxy, cyano, ethyl, dimethylamino, cyclopropyl, and isopropyl; in particular the substituents are selected from the group consisting of F, Cl, methyl, trifluoromethyl, methoxy, trifluoromethoxy, cyano, ethyl, and dimethylamino.

In an embodiment (E54) of embodiment (E1), the compound of formula (I) is selected among the compounds listed in Table 1, in the form of the free base, one or more tautomers thereof or a pharmaceutically acceptable acid addition salt thereof.

In an embodiment (E55) of any of embodiments (E1) to (E54) the compound has an IC50 value, determined as described in the section "PDE9 inhibition assay", of 1 micro molar or less.

In an embodiment (E56) of embodiment (E1) the compound is selected from the compounds listed in Table 1.

In an embodiment (E57) of any of embodiments (E1) to (E56) the compound is for use as a medicament.

In an embodiment (E58) of any of embodiments (E1) to (E56) the compound is for use in the treatment of a disease selected from the group consisting of Alzheimer's disease, mental retardation; CIAS, attention-deficit/hyperactivity disorder; and age-related cognitive decline, substance-induced psychotic disorder, for example psychosis induced by alcohol, amphetamine, cannabis, cocaine, hallucinogens, inhalants, opioids, or phencyclidine.

In an embodiment (E59) of any of embodiments (E1) to (E56) the compound is for preparation of a medicament for use in the treatment of a disease selected from the group consisting of Alzheimer's disease, mental retardation; CIAS, attention-deficit/hyperactivity disorder; and age-related cognitive decline, substance-induced psychotic disorder, for example psychosis induced by alcohol, amphetamine, cannabis, cocaine, hallucinogens, inhalants, opioids, or phencyclidine.

Embodiment (E60) of the present invention covers a method of treating a subject suffering from a disease selected from the group consisting of Alzheimer's disease, mental retardation; CIAS, attention-deficit/hyperactivity disorder; and age-related cognitive decline, substance-induced psychotic disorder, for example psychosis induced by alcohol, amphetamine, cannabis, cocaine, hallucinogens, inhalants, opioids, or phencyclidine, which method comprises administering to said subject a compound of any of embodiments (E1)-(E56).

In an embodiment (E61) the present invention covers a pharmaceutical composition comprising a therapeutically effective amount of a compound of any of embodiments (E1) to (E56), and one or more pharmaceutically acceptable carriers, diluents and excipients.

In an embodiment (E62) of embodiment (E61) the pharmaceutical composition is for the treatment of a disease selected from the group consisting of Alzheimer's disease, mental retardation; CIAS, attention-deficit/hyperactivity disorder; and age-related cognitive decline, substance-induced psychotic disorder, for example psychosis induced by alcohol, amphetamine, cannabis, cocaine, hallucinogens, inhalants, opioids, or phencyclidine.

Table 1 lists compounds of the invention and the corresponding $IC_{50}$ values (nM) determined as described in the section "PDE9 inhibition assay". Each of the compounds constitutes an individual embodiment of the present invention:

TABLE 1

Compounds of the invention and IC50 values

| Compound | PDE9_IC50 (nM) |
| --- | --- |
| 7-(4-fluorophenyl)-2-[4-methyl-1-[[6-(trifluoromethyl)-3-pyridyl]methyl]pyrrolidin-3-yl]-3H-imidazo[5,1-f][1,2,4]triazin-4-one | 86 |
| 2-[1-[(6-methoxy-3-pyridyl)methyl]-4-methyl-pyrrolidin-3-yl]-7-tetrahydropyran-4-yl-3H-imidazo[5,1-f][1,2,4]triazin-4-one | 67 |
| 2-[4-methyl-1-[[4-(trifluoromethyl)phenyl]methyl]pyrrolidin-3-yl]-7-tetrahydropyran-4-yl-3H-imidazo[5,1-f][1,2,4]triazin-4-one | 12 |
| 2-(1-benzyl-4-methyl-pyrrolidin-3-yl)-7-(3,6-dihydro-2H-pyran-4-yl)-3H-imidazo[5,1-f][1,2,4]triazin-4-one | 281 |
| 7-(4-fluorophenyl)-2-[1-[(6-methoxy-3-pyridyl)methyl]-4-methyl-pyrrolidin-3-yl]-3H-imidazo[5,1-f][1,2,4]triazin-4-one | 372 |
| 2-(1-benzyl-4-methyl-pyrrolidin-3-yl)-7-(3-pyridyl)-3H-imidazo[5,1-f][1,2,4]triazin-4-one | 656 |

TABLE 1-continued

Compounds of the invention and IC50 values

| Compound | PDE9_IC50 (nM) |
| --- | --- |
| 2-[1-[(2,4-difluorophenyl)methyl]-4-methyl-pyrrolidin-3-yl]-7-tetrahydropyran-4-yl-3H-imidazo[5,1-f][1,2,4]triazin-4-one | 48 |
| 2-(1-benzyl-4-methyl-pyrrolidin-3-yl)-7-(2,4-difluorophenyl)-3H-imidazo[5,1-f][1,2,4]triazin-4-one | 201 |
| 2-[4-methyl-1-[[4-(trifluoromethoxy)phenyl]methyl]pyrrolidin-3-yl]-7-tetrahydropyran-4-yl-3H-imidazo[5,1-f][1,2,4]triazin-4-one | 19 |
| 2-[[3-(4-methoxyphenyl)azetidin-1-yl]methyl]-7-tetrahydropyran-4-yl-3H-imidazo[5,1-f][1,2,4]triazin-4-one | 327 |
| 2-[1-[(2-chloro-4-methoxy-phenyl)methyl]-4-methyl-pyrrolidin-3-yl]-7-tetrahydropyran-4-yl-3H-imidazo[5,1-f][1,2,4]triazin-4-one | 41 |
| 2-[4-methyl-1-(quinoxalin-6-ylmethyl)pyrrolidin-3-yl]-7-tetrahydropyran-4-yl-3H-imidazo[5,1-f][1,2,4]triazin-4-one | 24 |
| 2-[[3-(4-fluorophenyl)azetidin-1-yl]methyl]-7-tetrahydropyran-4-yl-3H-imidazo[5,1-f][1,2,4]triazin-4-one | 563 |
| 2-[1-[(4-methoxyphenyl)methyl]-4-methyl-pyrrolidin-3-yl]-7-tetrahydropyran-4-yl-3H-imidazo[5,1-f][1,2,4]triazin-4-one | 49 |
| 2-[4-methyl-1-(4-pyridylmethyl)pyrrolidin-3-yl]-7-tetrahydropyran-4-yl-3H-imidazo[5,1-f][1,2,4]triazin-4-one | 52 |
| 2-[[3-(4-fluorophenoxy)azetidin-1-yl]methyl]-7-tetrahydropyran-4-yl-3H-imidazo[5,1-f][1,2,4]triazin-4-one | 80 |
| 2-[4-methyl-1-(pyrimidin-5-ylmethyl)pyrrolidin-3-yl]-7-tetrahydropyran-4-yl-3H-imidazo[5,1-f][1,2,4]triazin-4-one | 135 |
| 2-[1-[[4-(diethylamino)phenyl]methyl]-4-methyl-pyrrolidin-3-yl]-7-tetrahydropyran-4-yl-3H-imidazo[5,1-f][1,2,4]triazin-4-one | 13 |
| 2-[1-(2-furylmethyl)-4-methyl-pyrrolidin-3-yl]-7-tetrahydropyran-4-yl-3H-imidazo[5,1-f][1,2,4]triazin-4-one | 25 |
| 7-(4-fluorophenyl)-2-[(3S,4S)-4-methyl-1-(pyrimidin-2-ylmethyl)pyrrolidin-3-yl]-3H-imidazo[5,1-f][1,2,4]triazin-4-one | 341 |
| 2-[1-[(2-chloro-4-fluoro-phenyl)methyl]-4-methyl-pyrrolidin-3-yl]-7-tetrahydropyran-4-yl-3H-imidazo[5,1-f][1,2,4]triazin-4-one | 21 |
| 2-[1-[(4-dimethylaminophenyl)methyl]-4-methyl-pyrrolidin-3-yl]-7-tetrahydropyran-4-yl-3H-imidazo[5,1-f][1,2,4]triazin-4-one | 27 |
| 2-[4-methyl-1-(p-tolylmethyl)pyrrolidin-3-yl]-7-tetrahydropyran-4-yl-3H-imidazo[5,1-f][1,2,4]triazin-4-one | 47 |
| 2-(benzyloxymethyl)-7-tetrahydropyran-4-yl-3H-imidazo[5,1-f][1,2,4]triazin-4-one | 384 |
| 2-[[3-(2,6-difluorophenoxy)azetidin-1-yl]methyl]-7-tetrahydropyran-4-yl-3H-imidazo[5,1-f][1,2,4]triazin-4-one | 155 |
| 2-[1-(cyclohexylmethyl)-4-methyl-pyrrolidin-3-yl]-7-tetrahydropyran-4-yl-3H-imidazo[5,1-f][1,2,4]triazin-4-one | 409 |
| 7-tetrahydropyran-4-yl-2-[[3-[4-(trifluoromethoxy)phenoxy]azetidin-1-yl]methyl]-3H-imidazo[5,1-f][1,2,4]triazin-4-one | 158 |
| 2-[[3-(4-dimethylaminophenyl)azetidin-1-yl]methyl]-7-tetrahydropyran-4-yl-3H-imidazo[5,1-f][1,2,4]triazin-4-one | 86 |
| 2-[4-methyl-1-(3-pyridylmethyl)pyrrolidin-3-yl]-7-tetrahydropyran-4-yl-3H-imidazo[5,1-f][1,2,4]triazin-4-one | 37 |
| 2-[1-[(2,6-difluorophenyl)methyl]-4-methyl-pyrrolidin-3-yl]-7-tetrahydropyran-4-yl-3H-imidazo[5,1-f][1,2,4]triazin-4-one | 62 |
| 2-[(3-phenoxyazetidin-1-yl)methyl]-7-tetrahydropyran-4-yl-3H-imidazo[5,1-f][1,2,4]triazin-4-one | 153 |

TABLE 1-continued

Compounds of the invention and IC50 values

| Compound | PDE9_IC50 (nM) |
|---|---|
| 2-[[3-[(4-fluorophenyl)methoxy]azetidin-1-yl]methyl]-7-tetrahydropyran-4-yl-3H-imidazo[5,1-f][1,2,4]triazin-4-one | 10 |
| 2-[1-[3-(4-methoxyphenyl)azetidin-1-yl]ethyl]-7-tetrahydropyran-4-yl-3H-imidazo[5,1-f][1,2,4]triazin-4-one | 47 |
| 2-[4-methyl-1-[(5-methyl-2-furyl)methyl]pyrrolidin-3-yl]-7-tetrahydropyran-4-yl-3H-imidazo[5,1-f][1,2,4]triazin-4-one | 28 |
| 2-[1-[(5-chloro-2-furyl)methyl]-4-methyl-pyrrolidin-3-yl]-7-tetrahydropyran-4-yl-3H-imidazo[5,1-f][1,2,4]triazin-4-one | 63 |
| 2-[1-[3-(4-fluorophenyl)azetidin-1-yl]ethyl]-7-tetrahydropyran-4-yl-3H-imidazo[5,1-f][1,2,4]triazin-4-one | 128 |
| 2-[(3-phenylazetidin-1-yl)methyl]-7-tetrahydropyran-4-yl-3H-imidazo[5,1-f][1,2,4]triazin-4-one | 208 |
| 2-[[3-(4-methylphenoxy)azetidin-1-yl]methyl]-7-tetrahydropyran-4-yl-3H-imidazo[5,1-f][1,2,4]triazin-4-one | 91 |
| 2-[1-[(5-fluoro-3-pyridyl)methyl]-4-methyl-pyrrolidin-3-yl]-7-tetrahydropyran-4-yl-3H-imidazo[5,1-f][1,2,4]triazin-4-one | 25 |
| 2-[[3-(4-isopropylphenoxy)azetidin-1-yl]methyl]-7-tetrahydropyran-4-yl-3H-imidazo[5,1-f][1,2,4]triazin-4-one | 134 |
| 2-[1-[(3,4-difluorophenyl)methyl]-4-methyl-pyrrolidin-3-yl]-7-tetrahydropyran-4-yl-3H-imidazo[5,1-f][1,2,4]triazin-4-one | 23 |
| 2-[1-[(4-chlorophenyl)methyl]-4-methyl-pyrrolidin-3-yl]-7-tetrahydropyran-4-yl-3H-imidazo[5,1-f][1,2,4]triazin-4-one | 32 |
| 2-[1-[[6-(dimethylamino)-3-pyridyl]methyl]-4-methyl-pyrrolidin-3-yl]-7-tetrahydropyran-4-yl-3H-imidazo[5,1-f][1,2,4]triazin-4-one | 36 |
| methyl 5-[[3-methyl-4-(4-oxo-7-tetrahydropyran-4-yl-3H-imidazo[5,1-f][1,2,4]triazin-2-yl)pyrrolidin-1-yl]methyl]thiophene-2-carboxylate | 8 |
| 7-tetrahydropyran-4-yl-2-[[3-[5-(trifluoromethyl)-2-pyridyl]azetidin-1-yl]methyl]-3H-imidazo[5,1-f][1,2,4]triazin-4-one | 560 |
| 2-[[3-(3-pyridyloxy)azetidin-1-yl]methyl]-7-tetrahydropyran-4-yl-3H-imidazo[5,1-f][1,2,4]triazin-4-one | 350 |
| 2-[(3R,4R)-1-[(2,4-difluorophenyl)methyl]-4-methyl-pyrrolidin-3-yl]-7-tetrahydropyran-4-yl-3H-imidazo[5,1-f][1,2,4]triazin-4-one | 47 |
| 2-[(1R)-1-[3-(4-methoxyphenyl)azetidin-1-yl]ethyl]-7-tetrahydropyran-4-yl-3H-imidazo[5,1-f][1,2,4]triazin-4-one | 22 |
| 2-[1-[3-(4-fluorophenoxy)azetidin-1-yl]ethyl]-7-tetrahydropyran-4-yl-3H-imidazo[5,1-f][1,2,4]triazin-4-one | 57 |
| 2-[4-methyl-1-[(5-methyl-2-thienyl)methyl]pyrrolidin-3-yl]-7-tetrahydropyran-4-yl-3H-imidazo[5,1-f][1,2,4]triazin-4-one | 22 |
| 2-[1-[(5-chloro-2-thienyl)methyl]-4-methyl-pyrrolidin-3-yl]-7-tetrahydropyran-4-yl-3H-imidazo[5,1-f][1,2,4]triazin-4-one | 13 |
| 2-[4-methyl-1-[(4-pyrrolidin-1-ylphenyl)methyl]pyrrolidin-3-yl]-7-tetrahydropyran-4-yl-3H-imidazo[5,1-f][1,2,4]triazin-4-one | 61 |
| 2-(1-benzyl-4-methoxy-pyrrolidin-3-yl)-7-tetrahydropyran-4-yl-3H-imidazo[5,1-f][1,2,4]triazin-4-one | 54 |
| 2-[4-methyl-1-(pyrimidin-4-ylmethyl)pyrrolidin-3-yl]-7-tetrahydropyran-4-yl-3H-imidazo[5,1-f][1,2,4]triazin-4-one | Not determined |
| 2-[1-[3-(4-hydroxyphenyl)azetidin-1-yl]ethyl]-7-tetrahydropyran-4-yl-3H-imidazo[5,1-f][1,2,4]triazin-4-one | 120 |
| 2-[1-[(4-fluorophenyl)methyl]-4-methoxy-pyrrolidin-3-yl]-7-tetrahydropyran-4-yl-3H-imidazo[5,1-f][1,2,4]triazin-4-one | 94 |
| 2-[4-methoxy-1-(p-tolylmethyl)pyrrolidin-3-yl]-7-tetrahydropyran-4-yl-3H-imidazo[5,1-f][1,2,4]triazin-4-one | 90 |
| 2-[[3-(p-tolylmethoxy)azetidin-1-yl]methyl]-7-tetrahydropyran-4-yl-3H-imidazo[5,1-f][1,2,4]triazin-4-one | 150 |
| 2-[(3-benzylazetidin-1-yl)methyl]-7-tetrahydropyran-4-yl-3H-imidazo[5,1-f][1,2,4]triazin-4-one | Not determined |
| 2-[(3S,4S)-1-benzyl-4-methoxy-pyrrolidin-3-yl]-7-tetrahydropyran-4-yl-3H-imidazo[5,1-f][1,2,4]triazin-4-one | Not determined |
| 2-[1-[3-(4-methylphenoxy)azetidin-1-yl]ethyl]-7-tetrahydropyran-4-yl-3H-imidazo[5,1-f][1,2,4]triazin-4-one | 110 |
| 2-[[3-[(4-methoxyphenoxy)methyl]azetidin-1-yl]methyl]-7-tetrahydropyran-4-yl-3H-imidazo[5,1-f][1,2,4]triazin-4-one | 82 |
| 2-[(3-pyrimidin-2-ylazetidin-1-yl)methyl]-7-tetrahydropyran-4-yl-3H-imidazo[5,1-f][1,2,4]triazin-4-one | 3400 |
| 2-[1-[3-(4-pyrrolidin-1-ylphenyl)azetidin-1-yl]ethyl]-7-tetrahydropyran-4-yl-3H-imidazo[5,1-f][1,2,4]triazin-4-one | 110 |
| 2-[1-benzyl-4-(trifluoromethyl)pyrrolidin-3-yl]-7-tetrahydropyran-4-yl-3H-imidazo[5,1-f][1,2,4]triazin-4-one | 50 |
| 2-[[3-(5-pyrrolidin-1-ylpyrimidin-2-yl)azetidin-1-yl]methyl]-7-tetrahydropyran-4-yl-3H-imidazo[5,1-f][1,2,4]triazin-4-one | 120 |
| 2-[1-[3-(4-dimethylaminophenyl)azetidin-1-yl]ethyl]-7-tetrahydropyran-4-yl-3H-imidazo[5,1-f][1,2,4]triazin-4-one | 86 |
| 2-[4-methoxy-1-[(4-methoxyphenyl)methyl]pyrrolidin-3-yl]-7-tetrahydropyran-4-yl-3H-imidazo[5,1-f][1,2,4]triazin-4-one | 83 |
| 2-[1-(3-phenylazetidin-1-yl)ethyl]-7-tetrahydropyran-4-yl-3H-imidazo[5,1-f][1,2,4]triazin-4-one | 360 |
| 2-[1-[3-(3-fluoro-4-methoxy-phenyl)azetidin-1-yl]ethyl]-7-tetrahydropyran-4-yl-3H-imidazo[5,1-f][1,2,4]triazin-4-one | 240 |
| 2-[1-[3-(2-fluoro-4-methoxy-phenyl)azetidin-1-yl]ethyl]-7-tetrahydropyran-4-yl-3H-imidazo[5,1-f][1,2,4]triazin-4-one | 300 |
| 2-[1-[3-(4-ethoxyphenyl)azetidin-1-yl]ethyl]-7-tetrahydropyran-4-yl-3H-imidazo[5,1-f][1,2,4]triazin-4-one | 290 |
| 2-[1-[3-[(4-methoxyphenyl)methyl]azetidin-1-yl]ethyl]-7-tetrahydropyran-4-yl-3H-imidazo[5,1-f][1,2,4]triazin-4-one | 68 |
| 7-tetrahydropyran-4-yl-2-[1-[3-[4-(trifluoromethoxy)phenyl]azetidin-1-yl]ethyl]-3H-imidazo[5,1-f][1,2,4]triazin-4-one | 210 |
| 2-[1-[3-(4-methylphenoxy)azetidin-1-yl]ethyl]-7-tetrahydropyran-4-yl-3H-imidazo[5,1-f][1,2,4]triazin-4-one | 110 |
| 2-[[3-[(4-methoxyphenoxy)methyl]azetidin-1-yl]methyl]-7-tetrahydropyran-4-yl-3H-imidazo[5,1-f][1,2,4]triazin-4-one | 82 |
| 2-[(3-pyrimidin-2-ylazetidin-1-yl)methyl]-7-tetrahydropyran-4-yl-3H-imidazo[5,1-f][1,2,4]triazin-4-one | 3400 |
| 2-[1-[3-(4-pyrrolidin-1-ylphenyl)azetidin-1-yl]ethyl]-7-tetrahydropyran-4-yl-3H-imidazo[5,1-f][1,2,4]triazin-4-one | 110 |

DEFINITION OF SUBSTITUENTS

As used in the context of the present invention, the terms "halo" and "halogen" are used interchangeably and refer to fluorine, chlorine, bromine or iodine.

The term "$C_1$-$C_6$ alkyl" refers to a straight-chain or branched saturated hydrocarbon having from one to six carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, and n-hexyl. The expression "$C_1$-$C_6$ hydroxyalkyl" refers to a $C_1$-$C_6$ alkyl group as defined above which is substituted with one hydroxy group.

The term "halo($C_1$-$C_6$)alkyl" refers to a $C_1$-$C_6$ alkyl group as defined above which is substituted with up to three halogen atoms, such as trifluoromethyl.

The expression "$C_1$-$C_6$ alkoxy" refers to a straight-chain or branched saturated alkoxy group having from one to six carbon atoms, inclusive, with the open valency on the oxygen. Examples of such groups include, but are not limited to, methoxy, ethoxy, n-butoxy, 2-methylpentoxy and n-hexyloxy.

The term "$C_3$-$C_8$ cycloalkyl" typically refers to cyclopropyl, cyclobutyl, cyclopentyl, cyclohexyl, cycloheptyl or cyclooctyl.

The expression "$C_1$-$C_6$ alkyl($C_3$-$C_8$)cycloalkyl" refers to a $C_3$-$C_8$ cycloalkyl as defined above which is substituted with a straight-chain or branched $C_1$-$C_6$ alkyl. Examples of such groups include, but are not limited to, cyclopropylmethyl.

The term "heterocycloalkyl" refers to a four to eight membered ring containing carbon atoms and up to three N, O or S atoms, provided that the four to eight membered ring does not contain adjacent O or adjacent S atoms. The open valency is on either the heteroatom or carbon atom. Examples of such groups include, but are not limited to, azetidinyl, oxetanyl, piperazinyl, morpholinyl, thiomorpholinyl and [1,4]diazepanyl.

The term "hydroxyheterocycloalkyl" refers to a heterocycloalkyl as defined above which is substituted with one hydroxy group.

The term "$C_1$-$C_6$ alkyl-heterocycloalkyl" refers to a heterocycloalkyl as defined above which is substituted with a $C_1$-$C_6$ alkyl group. Examples of such groups include, but are not limited to, tetrahydropyran-4-yl-methyl and 2-morpholin-4-yl-ethyl.

The term "aryl" refers to a phenyl ring, optionally substituted with halogen, $C_1$-$C_6$ alkyl, $C_1$-$C_6$ alkoxy or halo($C_1$-$C_6$)alkyl as defined above. Examples of such groups include, but are not limited to, phenyl and 4-chlorophenyl.

The term "$C_1$-$C_6$arylalkyl" refers to an aryl as defined above which is substituted with a straight-chain or branched $C_1$-$C_6$ alkyl. Examples of such groups include, but are not limited to, benzyl and 4-chlorobenzyl.

The term aryloxy refers to an univalent radical of the form Ar—O (such as phenoxy) composed of an aryl group (Ar) united with oxygen (O).

The term heteroaryloxy refers to an aryloxy where one or more carbon atoms have been substituted with one more hetero atoms, such as N, O, S.

In the context of the present invention the term 'cyclization point' is understood to mean that connecting the atoms indicated to be cyclization points by a bond results in a cyclic structure (a ring). The cyclization point is indicated with a * in the illustrative reaction scheme below:

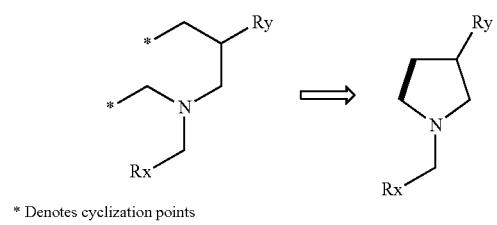

* Denotes cyclization points

Additionally, the present invention further provides certain embodiments of the invention, which are described below. Additionally, the present invention further provides certain embodiments of the invention that are described below.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., J. Pharm. Sci. 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Composition

The present invention further provides a pharmaceutical composition comprising a therapeutically effective amount of a compound of formula (I) and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of formula (I) and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound having the utility of a free base. When a compound of formula (I) contains a free base such salts are prepared in a conventional manner by treating a solution or suspension of a free base of formula (I) with a molar equivalent of a pharmaceutically acceptable acid. Representative examples of suitable organic and inorganic acids are described above.

For parenteral administration, solutions of the compounds of formula (I) in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula (I) may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water.

Similarly, the carrier or diluent may include any sustained release material known in the art, such as glyceryl monostearate or glyceryl distearate, alone or mixed with a wax. The pharmaceutical compositions formed by combining the compounds of formula (I) and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Diseases

In a particular embodiment the PDE9 inhibitors of the present invention may be used in the treatment of cognition deficiencies related to neurodegenerative disorders, such dementia, such as cortical dementia or subcortical dementia.

Cortical dementias arise from a disorder affecting the cerebral cortex, the outer layers of the brain that play a critical role in cognitive processes such as memory and language. Particularly considered cortical dementias are Alzheimer's disease; vascular dementia (also known as multi-infarct dementia), including Binswanger's disease; Dementia with Lewy bodies (DLB); Alcohol-Induced Persisting Dementia, including Korsakoff's syndrome and Wernicke's encephalopathy; frontotemporal lobar degeneration (FTLD), including: Pick's disease, frontotemporal dementia (or frontal variant FTLD), semantic dementia (or temporal variant FTLD), and progressive non-fluent aphasia; Creutzfeldt-Jakob disease; dementia pugilistica; Moya-moya disease; and posterior cortical atrophy (an Alzheimer's disease variant).

Subcortical dementias result from dysfunction in the parts of the brain that are beneath the cortex. Usually, the memory loss and language difficulties that are characteristic of cortical dementias are not present. Rather, people with subcortical dementias, such as Huntington's disease, Parkinson's Disease, and AIDS dementia complex, tend to show changes in their personality and attention span, and their thinking slows down. Particularly considered subcortical dementias are dementia due to Huntington's disease, dementia due to hypothyroidism, dementia due to Parkinson's disease, dementia due to Vitamin B1 deficiency, dementia due to Vitamin B12 deficiency, dementia due to folate deficiency, dementia due to syphilis, dementia due to subdural hematoma, dementia due to hypercalcaemia, dementia due to hypoglycaemia, AIDS dementia complex, pseudodementia (a major depressive episode with prominent cognitive symptoms), substance-induced persisting dementia, dementia due to multiple etiologies, dementia due to other general medical conditions (i.e. end stage renal failure, cardiovascular disease etc.), dementia not otherwise specified (used in cases where no specific criteria is met).

EXPERIMENTAL

General Description of Pyrrolidine-Substituted 3H-imidazo[5,1-f][1,2,4]triazin-4-ones Compounds of formula I can be made by reductive amination of compounds of formula X, with aryl aldehydes in the presence of $NaBH_3CN$ or $Na(OAc)_3BH$, and a few drops of acetic acid as catalyst in DME or MeOH, or by alkylation of compound X with aryl methyl halides, in the presence of bases, such as $K_2COO_3$ or DIEA, in DMF or $CH_3CN$.

Boc protection with $Boc_2O$ of compounds with formula VIII. Compounds of formula VIII can be synthesized by Suzuki reaction of compounds of formula VII, with a variety of organo boronic acids or boronic esters in the presence of Xantphos, and a palladium catalyst, such as $Pd(dppf)Cl_2$, $Pd(PPh_3)_2Cl_2$, $Pd(PPh_3)_4$ and a base, such as $K_3PO_4$, $K_2CO_3$, or $Cs_2CO_3$, with conventional heating or microwave heating in DMF or Toluene. Compounds of formula VII can be prepared by deprotonation with n-BuLi, followed by treatment with $I_2$, of compound VI, which can be made by cyclization in the presence of $NH_4OAc$ in MeOH with heating of compound V. Compound V can be made by coupling reaction of compound III, obtained from reaction between compound II with (aminooxy)diphenylphosphine oxide, with compound IV, which can be prepared from a known compound XI. Compound XI is made according to the procedures in patent WO 2009/76387.

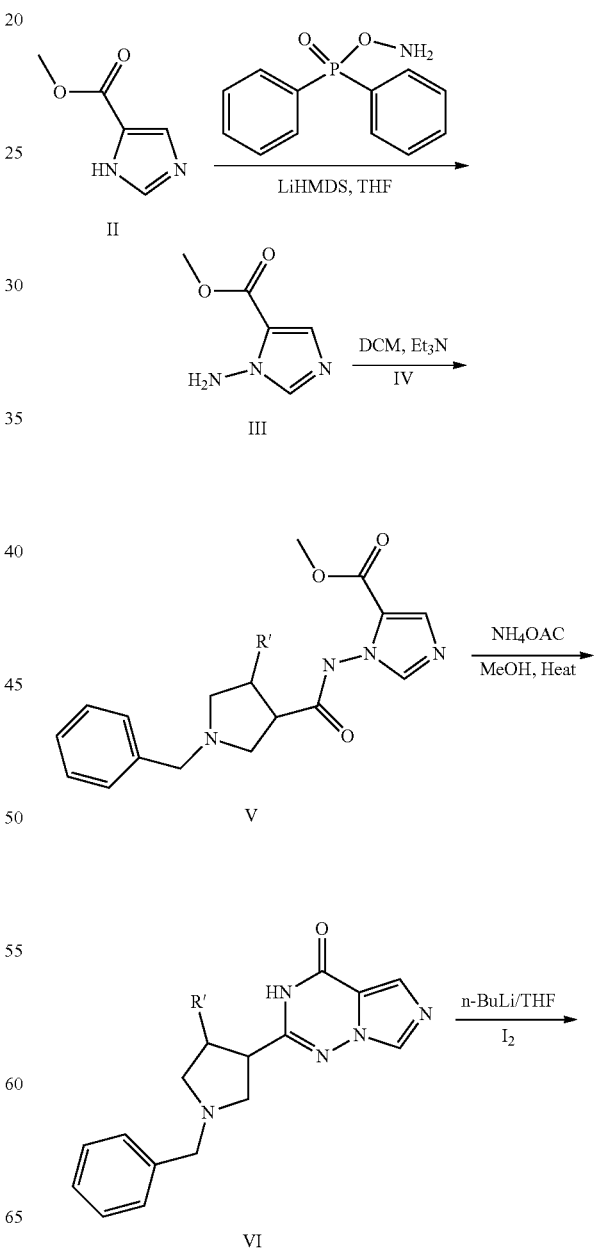

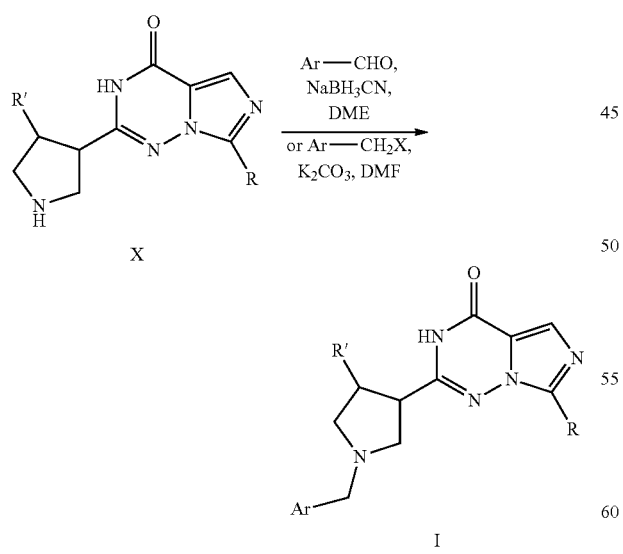

R' = Methyl, Trifluoromethyl, Methoxyl

Compounds of formula X can be prepared by deprotection with HCl in MeOH of compound of formula IX, which can be obtained by one-pot hydrogenolysis debenzylation and

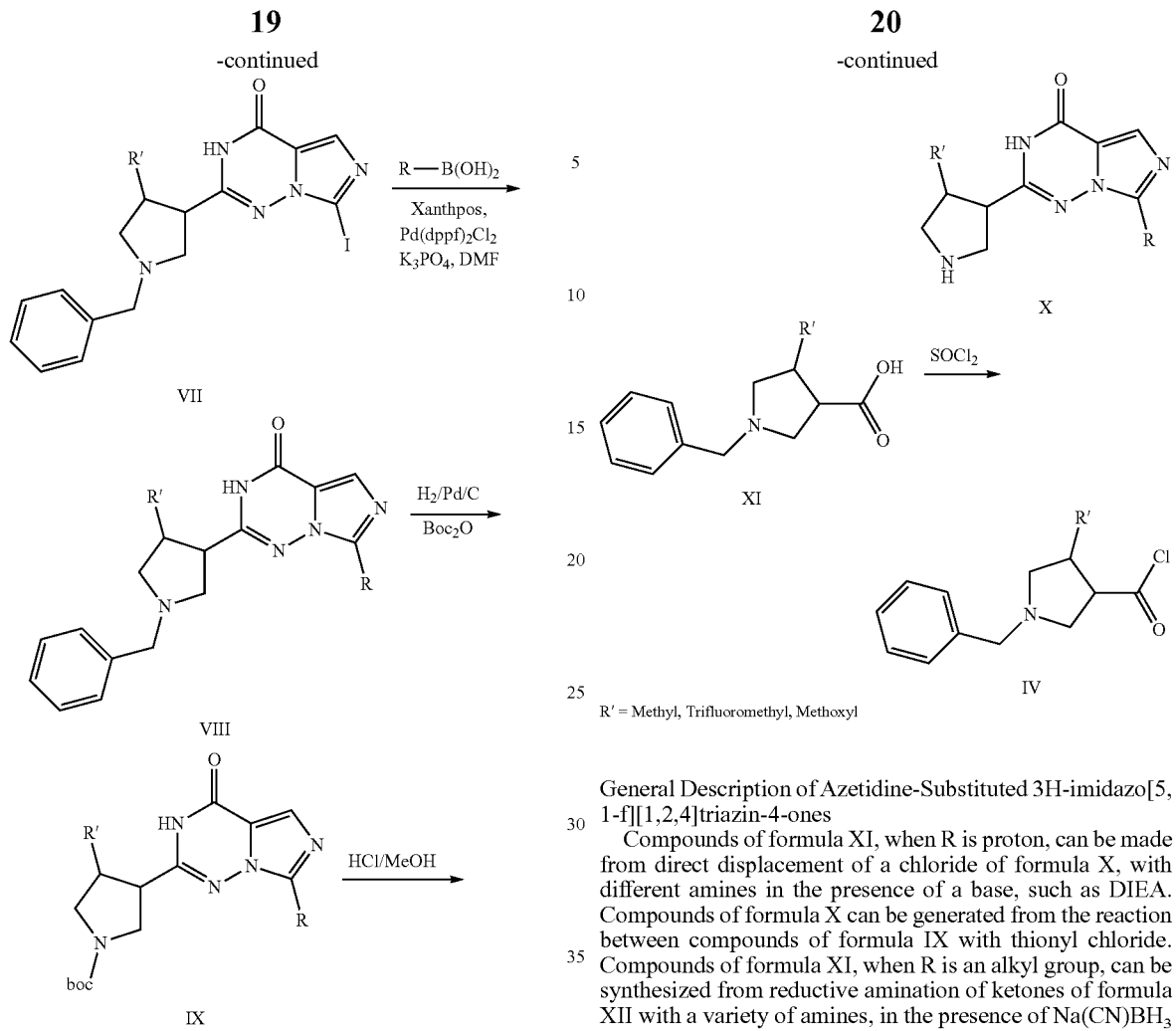

General Description of Azetidine-Substituted 3H-imidazo[5,1-f][1,2,4]triazin-4-ones Compounds of formula XI, when R is proton, can be made from direct displacement of a chloride of formula X, with different amines in the presence of a base, such as DIEA. Compounds of formula X can be generated from the reaction between compounds of formula IX with thionyl chloride. Compounds of formula XI, when R is an alkyl group, can be synthesized from reductive amination of ketones of formula XII with a variety of amines, in the presence of Na(CN)BH$_3$ or Na(OAc)$_3$BH. Ketones of formula XII can be made from oxidation of the alcohol of formula IX with MnO$_2$ in DCM.

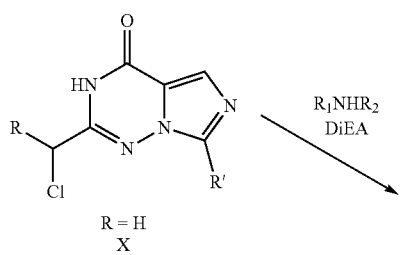

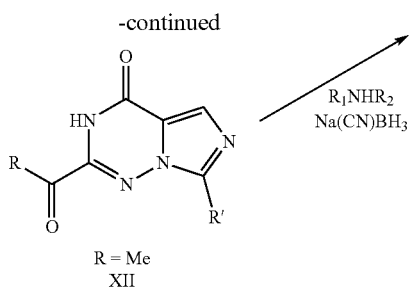

Alcohols of formula IX can be prepared from debenzylation, with Pd/C in 50 psi of $H_2$, of compounds of formula VIII, which can be synthesized by Suzuki coupling of compounds of formula VII, with a variety of boronic acids or boronic esters, in the presence of a palladium catalyst, such as $Pd(PPh_3)_4$, $Pd(dppf)CL_2$, etc, with microwave heating. Compounds of formula VII can be generated from deprotonation of compounds of formula VI with a base, such as n-BuLi, followed by treatment with $I_2$.

prepared by coupling in the presence of HATU of carboxylic acid III with 1-aminoimidazole II, which was made from the reaction of methyl 1H-imidazole-5-carboxylate (1) with (aminooxy)diphenylphosphine oxide in the presence of a base, such as LiHMDS.

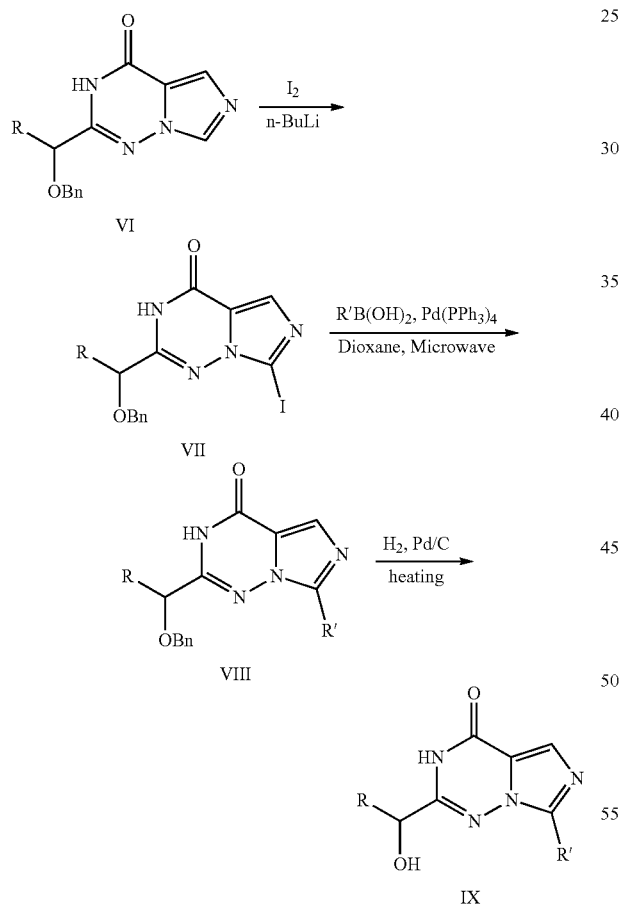

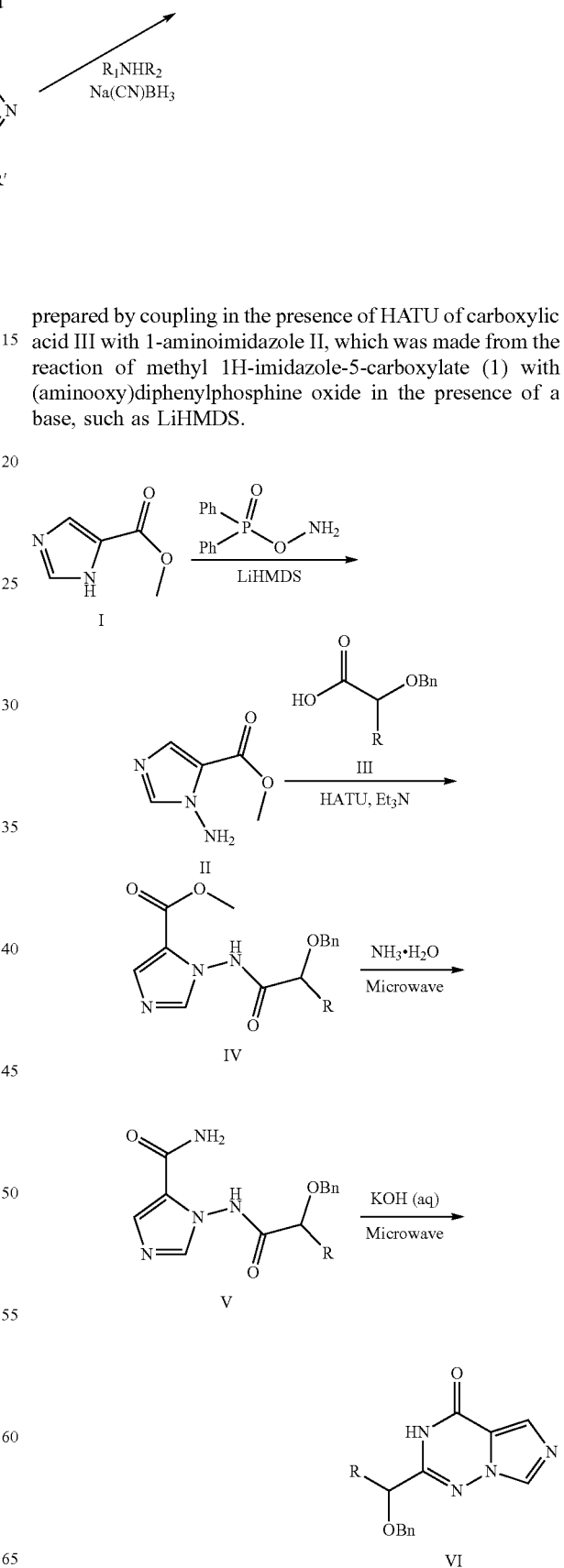

Compounds of formula VI can be made from microwave heating of amide of formula V in the presence of aqueous solution of a base, such as KOH. Amide of formula V can be generated from aminolysis of esters of formula IV with aqueous solution of ammonia. Esters of formula IV can be

Part I (Pyrrolidine Series)

Preparation of Intermediates 2-(1-Benzyl-4-methyl-pyrrolidin-3-yl)-7-iodo-3H-imidazo[5,1-f][1,2,4]triazin-4-one

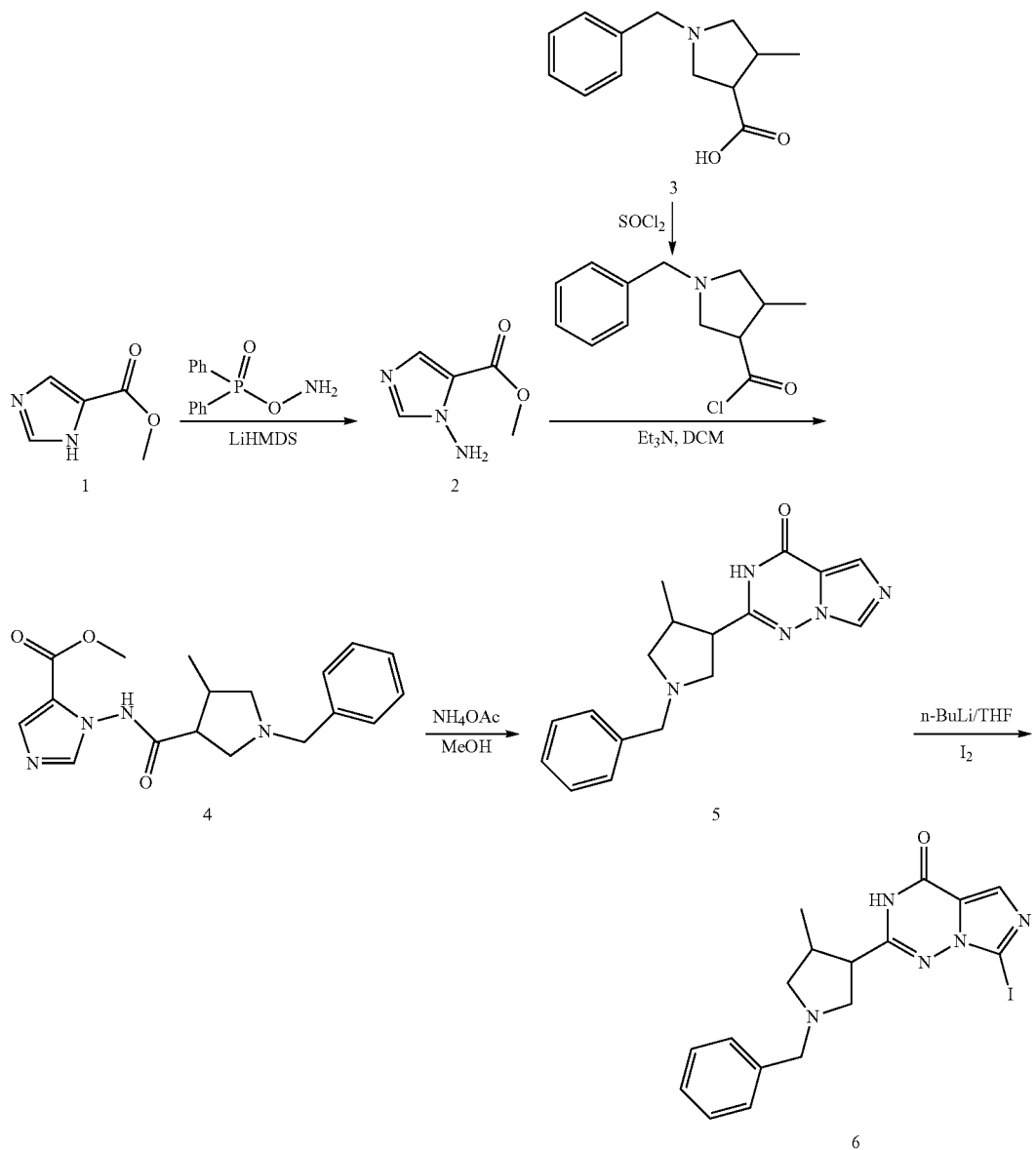

Scheme 1

3-Amino-3H-imidazole-4-carboxylic acid methyl ester (2)

To a suspension of compound 1 (4.0 g, 31.7 mmol) in dry THF was dropwise added LiHMDS (38 mL, 38 mmol) at −78° C. in $N_2$. The mixture was stirred at −78° C. for 2 hours. Then it was stirred at −30° C. for 20 minutes. (Aminooxy)diphenylphosphine oxide (8.14 g, 31.7 mmol) was added in portions at −10° C. The reaction mixture was allowed to warm to r.t overnight. The reaction mixture was diluted with EtOAc (100 mL) and filtered. The filtrate was concentrated in vacuum. The residue was purified by silica gel column chromatography (eluted with DCM/MeOH=150:1 to 100:1) to afford the desired product 2 (2.4 g, 53% yield) as a white powder. LC-MS: m/z 142.50 $[M+1]^+$. $^1H$ NMR (400 MHz, DMSO-d6): δ 7.82 (s, 1H), 7.54 (s, 1H), 6.20 (br. s, 2H), 3.79 (s, 3H).

3-[(1-Benzyl-4-methyl-pyrrolidine-3-carbonyl)-amino]-3H-imidazole-4-carboxylic acid methyl ester (4)

A mixture of compound 3 (prepared according to procedures in patent WO 2009/76387) (13 g, 59.4 mmol) in 30 mL of $SOCl_2$ was refluxed at 85° C. for 4 hours. The solvent was removed by concentration in vacuo to afford the acid chloride of 3.

The acid chloride was dissolved in 30 mL of $CH_2Cl_2$. This resulting solution was added dropwise to a solution of compound 2 (3.5 g, 24.8 mmol) and $Et_3N$ (10 mL, 68.2 mmol) in 100 mL of $CH_2Cl_2$ at 0° C. over 20 minutes. Then the reaction mixture was stirred at room temperature for 8 hours. The reaction mixture was washed with brine (100 mL×2). The organic phase was dried over $Na_2SO_4$, filtered and concentrated to afford the crude residue, which was purified by column chromatography on silica gel (eluted with DCM/MeOH=100:1 to 50:1) to afford compound 4 (5.0 g, 58.9% yield) as a red oil. LC-MS: m/z 343.11 $[M+1]^+$. $^1H$ NMR (400 MHz, $CDCl_3$): δ 7.70 (s, 1H), 7.63 (s, 1H), 7.33~7.25 (m, 5H), 3.78 (s, 3H), 3.80~3.77 (d, J=12.4 Hz, 1H), 3.68~3.65 (d, J=12.4 Hz, 1H), 3.36~3.28 (m, 2H), 2.70~2.65 (m, 1H), 2.56~2.50 (m, 2H), 1.92 (m, 1H), 1.16 (d, J=7.2 Hz, 3H).

2-(1-Benzyl-4-methyl-pyrrolidin-3-yl)-3H-imidazo[5,1-f][1,2,4]triazin-4-one (5)

To a 300 mL sealed tube was added a mixture of compound 4 (4.7 g, 13.7 mmol), $NH_4OAc$ (11 g, 14.3 mmol) and ammonium hydroxide (50 mL) in MeOH (120 mL). The reaction mixture was stirred at 130° C. for 2 days. After cooling down, the reaction mixture was concentrated in vacuo. The residue was diluted with $CH_2Cl_2$ (100 mL) and washed with water (50 mL×2). The organic phase was separated and dried over $Na_2SO_4$. After filtering, the filtrate was concentrated under reduced pressure. The residue was purified by column chromatography on silica gel (eluted with DCM/MeOH=50:1 to 30:1) to afford compound 5 (1.8 g, 40.6% yield) as a white solid. LC-MS: m/z 310.17 $[M+1]^+$. $^1H$ NMR (400 MHz, $CDCl_3$): δ 8.02 (s, 1H), 7.85 (s, 1H), 7.39~7.28 (m, 5H), 3.82 (d, J=12.4 Hz, 1H), 3.58 (d, J=12.4 Hz, 1H), 3.41~3.37 (m, 1H), 2.99 (d, J=6.4 Hz, 1H), 2.72~2.70 (m, 1H), 2.54~2.50 (m, 1H), 2.44~2.40 (m, 1H), 1.95~1.91 (m, 1H), 1.20 (d, J=6.4 Hz, 3H).

2-(1-Benzyl-4-methyl-pyrrolidin-3-yl)-7-iodo-3H-imidazo[5,1-f][1,2,4]triazin-4-one (6)

To a solution of compound 5 (1.0 g, 3.24 mmol) in dry THF (70 mL) was added n-BuLi (2.5 M, 2 mL) dropwise at −78° C. over 30 minutes. The reaction was stirred at −45° C. for 30 minutes.

Then a solution of iodine in THF (20 mL) was dropwise added at −78° C. over 10 minutes. The resulting mixture was stirred at 0° C. for 2 hours. The reaction was quenched with saturated aqueous $Na_2S_2O_3$ solution (10 mL). Then the reaction mixture was diluted with EtOAc (200 mL), and washed with brine (50 mL×2). The separated organic phase was dried over $Na_2SO_4$, filtered and concentrated under reduced pressure. The residue was purified by column chromatography on silica gel (eluted by PE/EtOAc=10:1 to 2:1) to afford compound 6 (930 mg, 66% yield) as a white solid. LC-MS: m/z 435.99 $[M+1]^+$. $^1H$ NMR (400 MHz, $CDCl_3$): δ 7.89 (s, 1H), 7.37~7.26 (m, 5H), 3.82 (d, J=12.4 Hz, 1H), 3.59 (d, J=12.4 Hz, 1H), 3.42~3.38 (m, 1H), 2.98 (d, J=8.4 Hz, 1H), 2.82~2.81 (m, 1H), 2.55~2.51 (m, 1H), 2.45~2.42 (m, 1H), 1.96~1.92 (m, 1H), 1.22 (d, J=7.2 Hz, 3H).

2-(4-Methyl-pyrrolidin-3-yl)-7-(tetrahydro-pyran-4-yl)-3H-imidazo[5,1-f][1,2,4]triazin-4-one Hydrochloric acid salt Scheme 2

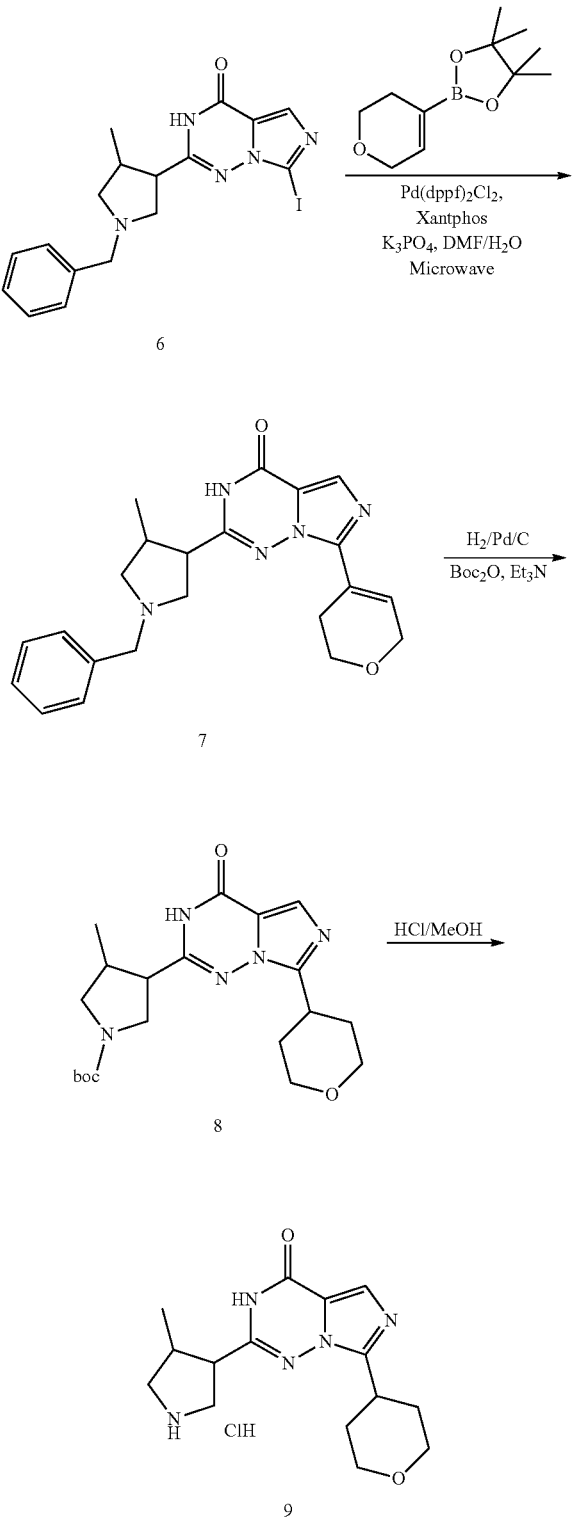

2-(1-Benzyl-4-methyl-pyrrolidin-3-yl)-7-(3,6-dihydro-2H-pyran-4-yl)-3H-imidazo[5,1-f][1,2,4]triazin-4-one (7)

To a mixture of compound 6 (100 mg, 0.23 mmol) and 4-(4,4,5,5-Tetramethyl-[1,3,2]dioxaborolan-2-yl)-3,6-dihydro-2H-pyran (145 mg, 0.69 mmol) in DMF (10 mL) was added potassium phosphate (146 mg, dissolved in 1 mL of $H_2O$). The reaction mixture was degassed by purging with $N_2$ for 15 min, before Pd(dppf)$_2$Cl$_2$ (28 mg, 0.035 mmol) and Xantphos (40 mg, 0.069 mmol) were added. The resulting suspension was bubbled with nitrogen for 10 minutes. The reaction mixture was heated to 150° C. under microwave irradiation for one hour. After cooling down, the reaction mixture was diluted with EtOAc (50 mL), and the precipitate was filtered off. The filtrate was washed with brine (50 mL), dried over $Na_2SO_4$, filtered and the filtrate was concentrated. The crude product was purified by column chromatography on silica gel (eluting with EtOAc) to afford 7 (50 mg, 55% yield) as a white solid. LC-MS: m/z 393.03 [M+1]$^+$. $^1$H NMR (400 MHz, CDCl$_3$): δ 7.85 (s, 1H), 7.37~7.22 (m, 6H), 4.40 (d, J=2.8 Hz, 2H), 3.95~3.92 (m, 2H), 3.82~3.79 (d, J=12.6 Hz, 1H), 3.61~3.58 (d, J=12.6 Hz, 1H), 3.39~3.37 (m, 1H), 3.00~2.98 (d, J=10.0 Hz, 1H), 2.76~2.73 (m, 3H), 2.54~2.52 (m, 1H), 2.44~2.42 (m, 1H), 1.95~1.90 (m, 2H), 1.21 (d, J=7.2 Hz, 3H).

3-Methyl-4-[4-oxo-7-(tetrahydro-pyran-4-yl)-3,4-dihydro-imidazo[5,1-f][1,2,4]triazin-2-yl]-pyrrolidine-1-carboxylic acid tert-butyl ester (8)

To a 75 mL flask was added compound 7 (0.3 g, 0.76 mmol), di-tert-butyl dicarbonate (1.6 g, 7.6 mmol), potassium acetate (0.75 g, 7.6 mmol), 10% Pd/C (300 mg, 0.28 mmol) and methanol (40 mL). The reaction mixture was stirred with hydrogen (50 psi) at 50° C. until LCMS showed that the starting material was almost consumed. After cooling down, the reaction mixture was filtered through Celite. The filtrate was concentrated under reduced pressure. The crude product was purified by column chromatography on silica gel (eluting with EtOAc) to afford compound 8 (50 mg, 42% yield) as a white solid. LC-MS: m/z 404.35 [M+1]$^+$. $^1$H NMR (400 MHz, CDCl$_3$): δ 10.49 (br. s, 1H), 7.86 (s, 1H), 4.11~4.08 (m, 2H), 3.91 (m, 1H), 3.76 (m, 1H), 3.63~3.57 (m, 3H), 3.46~3.41 (m, 1H), 3.11~3.06 (m, 1H), 2.91~2.89 (m, 1H), 2.69~2.65 (m, 1H), 2.11~2.05 (m, 2H), 1.93~1.90 (m, 2H), 1.48 (s, 9H), 1.20~1.18 (d, J=6.8 Hz, 3H).

2-(4-Methyl-pyrrolidin-3-yl)-7-(tetrahydro-pyran-4-yl)-3H-imidazo[5,1-f][1,2,4]triazin-4-one Hydrochloric acid salt (9)

To a solution of compound 8 (130 mg, 0.32 mmol) in $CH_2Cl_2$ (10 mL) was added a saturated solution of HCl in diethylether (20 mL). The resulting mixture was stirred at room temperature for 2 hours. The reaction was concentrated in vacuo to dryness to afford compound 9 (110 mg, 100% yield). LC-MS (free base): m/z 304.37 [M+1]$^+$. $^1$H NMR (400 MHz, D$_2$O-d2): δ 8.02 (s, 1H), 3.98~3.95 (dd, J=2.8, 8.8 Hz, 2H), 3.64~3.60 (m, 3H), 3.56~3.50 (m, 3H), 3.15~3.09 (m, 1H), 3.01~2.96 (m, 1H), 2.72~2.67 (m, 1H), 1.92~1.87 (m, 4H), 1.09 (d, J=6.8 Hz, 3H).

7-(4-Fluoro-phenyl)-2-(4-methyl-pyrrolidin-3-yl)-3H-imidazo[5,1-f][1,2,4]triazin-4-one Hydrochloric acid salt

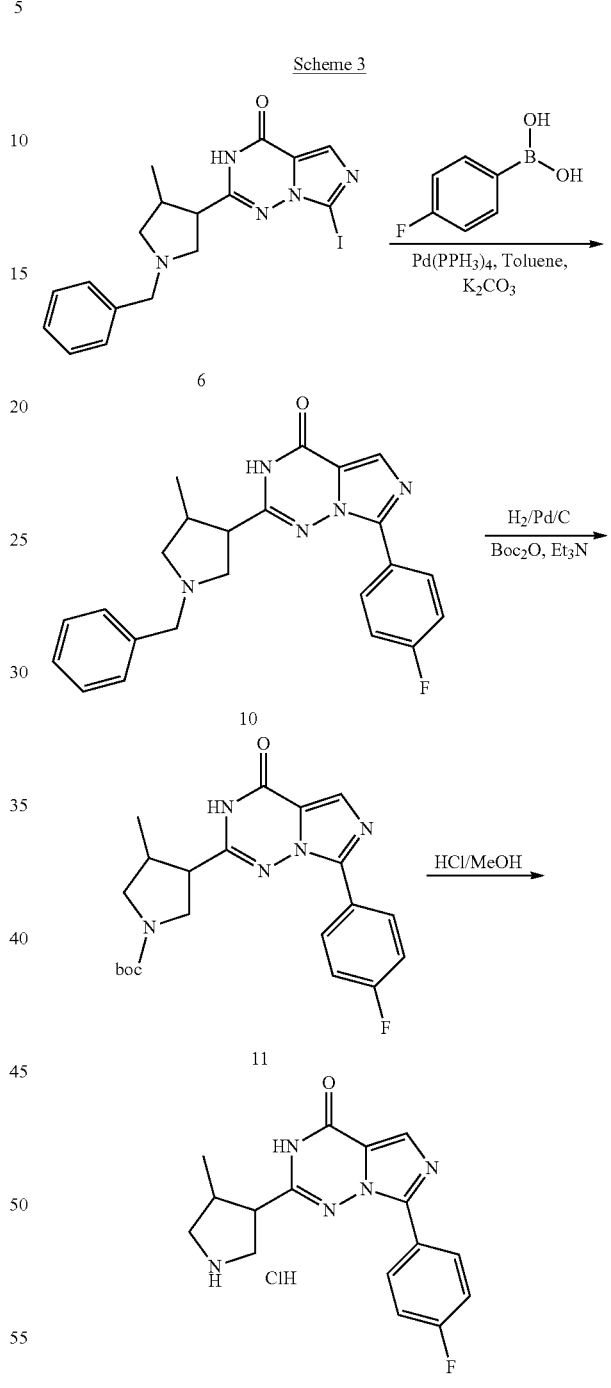

Scheme 3

2-(1-Benzyl-4-methyl-pyrrolidin-3-yl)-7-(4-fluorophenyl)-3H-imidazo[5,1-f][1,2,4]triazin-4-one (10)

To a solution of compound 6 (500 mg, 1.14 mmol) and 4-fluorophenylboronic acid (300 mg, 2.14 mmol) in 30 mL of toluene was added $K_2CO_3$ (1.0 g, 7.24 mmol). The resulting mixture was degassed by purging with nitrogen for 15 min, before Pd(PPh$_3$)$_4$ (120 mg, 0.10 mmol) was added. The resulting suspension was bubbled with nitrogen for 10 minutes. The reaction mixture was heated to 100° C. for 18 hours and then cooled to room temperature. After removal of the solvent, the residue was purified by chromatography on silica gel column (eluted with PE/EtOAc=5:1 to 1:2) to afford compound 10 (398 mg, 86% yield) as a white solid. LC-MS: m/z 404.31 [M+1]$^+$. $^1$H NMR (400 MHz, CDCl$_3$): δ 8.34~8.31 (m, 2H), 7.95 (s, 1H), 7.38 (m, 4H), 7.31 (m, 1H), 7.16 (m, 2H), 3.85 (d, J=12.4 Hz, 1H), 3.63 (d, J=12.4 Hz, 1H), 3.44~3.40 (m, 1H). 3.05 (d, J=10 Hz, 1H), 2.84 (m, 1H), 2.61 (m, 1H), 2.50~2.47 (m, 1H), 1.99 (m, 1H), 1.22 (d, J=6.8 Hz, 3H).

3-[7-(4-Fluoro-phenyl)-4-oxo-3,4-dihydro-imidazo [5,1-f][1,2,4]triazin-2-yl]-4-methyl-pyrrolidine-1-carboxylic acid tert-butyl ester (11)

Compound 11 was prepared in the same method as described for preparation of compound 8.46% yield. LC-MS: m/z 414.08 [M+1]$^+$. $^1$H NMR (400 MHz, DMSO-d6): δ 12.01 (br. s, 1H), 8.36 (m, 2H), 7.88 (s, 1H), 7.35 (m, 2H), 3.75 (m, 1H), 3.56 (m, 2H). 2.95 (m, 2H), 2.64 (m, 1H), 1.39 (s, 9H), 1.10 (d, J=6.4 Hz, 3H).

7-(4-Fluoro-phenyl)-2-(4-methyl-pyrrolidin-3-yl)-3H-imidazo[5,1-f][1,2,4]triazin-4-one Hydrochloric acid salt (12)

Compound 12 was prepared in the same way as described for preparation for compound 9. 95% yield. LC-MS: m/z 314.31 [M+1]$^+$. $^1$H NMR (400 MHz, DMSO-d6): δ 12.19 (s, 1H), 9.47~9.49 (br. s, 2H), 8.37 (dd, J=5.6, 8.4 Hz, 2H), 7.93 (s, 1H), 7.39 (m, 2H), 3.67 (m, 1H), 3.48 (m, 2H). 3.09 (m, 1H), 2.91 (m, 1H), 2.71 (m, 1H), 1.15 (d, J=6.8 Hz, 3H).

Scheme 4

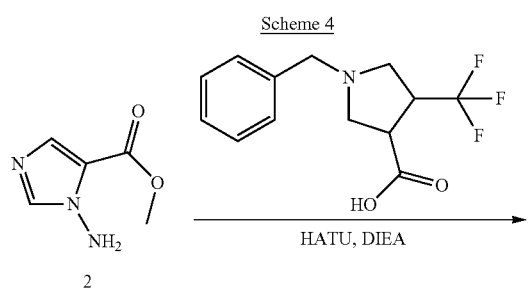

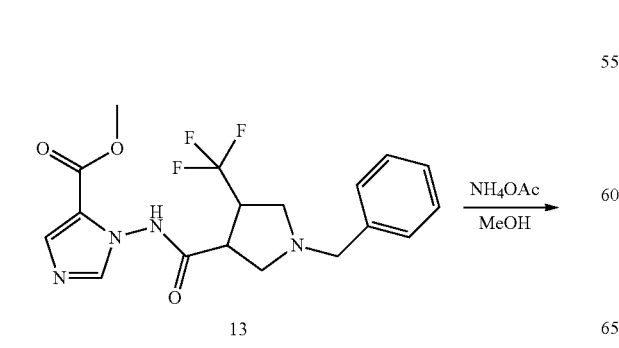

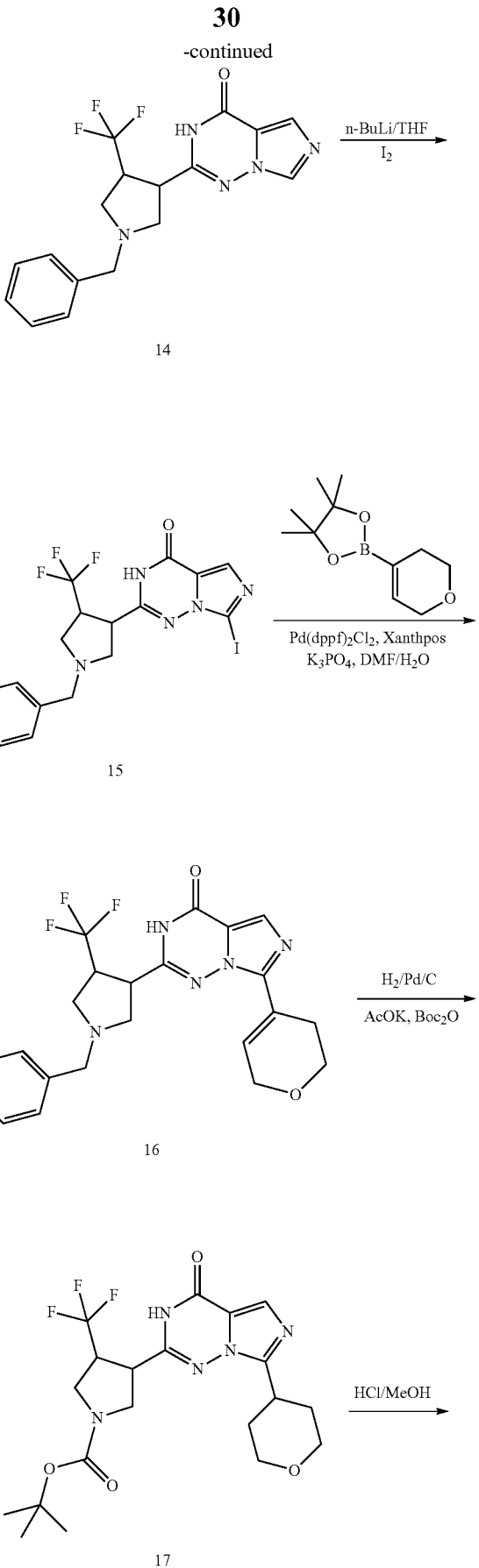

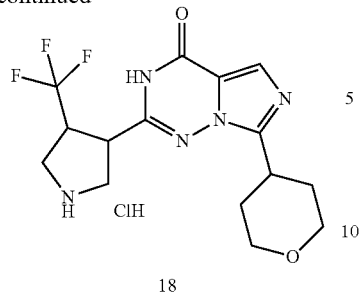

18

3-[(1-Benzyl-4-trifluoromethyl-pyrrolidine-3-carbonyl)-amino]-3H-imidazole-4-carboxylic acid methyl ester (13)

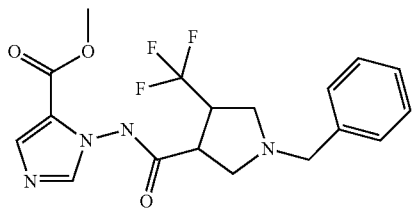 [SMILES: COC(=O)c1cncn1NC(=O)C1CN(Cc2ccccc2)CC1C(F)(F)F]

To a solution of compound 2 (2.0 g, 14.1 mmol), 1-Benzyl-4-trifluoromethyl-pyrrolidine-3-carboxylic acid (4.06 g, 14.9 mmol) and DIEA (10 mL, 42.5 mmol) in DMF (30 mL) was added HATU (8.1 g, 21.2 mmol). The resulting reaction mixture was stirred at r.t. overnight. The reaction was monitored by LC-MS. The reaction was quenched with water (100 mL) when it was complete. The aqueous solution was extracted with EtOAc (80 mL×3). The combined organic phase was washed with brine and concentrated to afford the crude product. The residue was purified by silica gel column (eluted with PE/EA=5:1 to 1:2) to afford compound 13 (4.8 g, 85.6% yield) as white oil. LC-MS: m/z 397 [M+1]$^+$. $^1$H NMR (400 MHz, CDCl$_3$): δ 8.00 (br. s, 1H), 7.70 (s, 1H), 7.65 (s, 1H), 7.34~7.28 (m, 5H), 3.81 (s, 3H), 3.78~3.72 (m, 2H), 3.41~3.38 (m, 1H), 3.30~3.24 (m, 2H), 3.14~3.12 (m, 1H), 2.71~2.67 (m, 1H), 2.58~2.53 (m, 1H).

2-(1-Benzyl-4-trifluoromethyl-pyrrolidin-3-yl)-3H-imidazo[5,1-f][1,2,4]triazin-4-one (14)

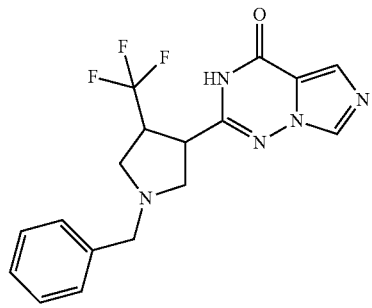 [SMILES: O=c1[nH]c(C2CN(Cc3ccccc3)CC2C(F)(F)F)nn2cncc12]

The procedure for the preparation of compound 14 was similar to that of compound 5.

28.8% yield. LC-MS: m/z 364 [M+1]$^+$. $^1$H NMR (400 MHz, CDCl$_3$): δ 8.06 (s, 1H), 7.88 (s, 1H), 7.41~7.30 (m, 5H), 3.88 (d, J=12.8 Hz, 1H), 3.67 (d, J=12.4 Hz, 1H), 3.45~3.40 (m, 1H), 3.35~3.33 (m, 1H), 3.08~3.06 (m, 2H), 2.65~2.61 (m, 1H), 2.52~2.48 (m, 1H).

2-(1-Benzyl-4-trifluoromethyl-pyrrolidin-3-yl)-7-iodo-3H-imidazo[5,1-f][1,2,4]triazin-4-one (15)

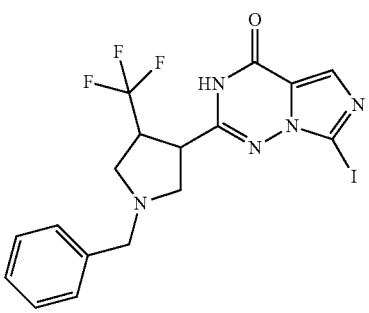 [SMILES: O=c1[nH]c(C2CN(Cc3ccccc3)CC2C(F)(F)F)nn2c(I)ncc12]

The procedure for the preparation of compound 15 was similar to that of compound 6.

38.7% yield. LC-MS: m/z 490 [M+1]$^+$. $^1$H NMR (400 MHz, CDCl$_3$): δ 7.91 (s, 1H), 7.40~7.29 (m, 5H), 3.87 (d, J=12.8 Hz, 1H), 3.66 (d, J=12.4 Hz, 1H), 3.46~3.41 (m, 2H), 3.08~3.05 (m, 2H), 2.67~2.62 (m, 1H), 2.54~2.49 (m, 1H).

2-(1-Benzyl-4-trifluoromethyl-pyrrolidin-3-yl)-7-(3,6-dihydro-2H-pyran-4-yl)-3H-imidazo[5,1-f][1,2,4]triazin-4-one (16)

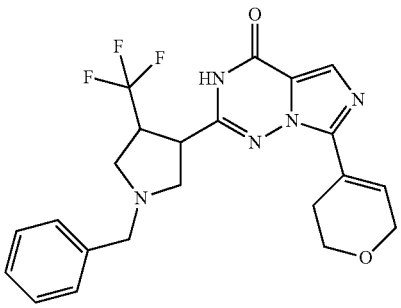 [SMILES: O=c1[nH]c(C2CN(Cc3ccccc3)CC2C(F)(F)F)nn2c(C3=CCOCC3)ncc12]

The procedure for the preparation of compound 16 was similar to that of compound 7.

91% yield. LC-MS: m/z 446 [M+1]$^+$. $^1$HNMR (400 MHz, CDCl$_3$): δ 7.87 (s, 1H), 7.37~7.27 (m, 5H), 7.18 (m, 1H), 4.39 (m, 2H), 3.94~3.91 (m, 2H), 3.88~3.85 (m, 1H), 3.68~3.65 (m, 1H), 3.41~3.36 (m, 2H), 3.09~3.04 (m, 2H), 2.76 (m, 2H), 2.65~2.60 (m, 1H), 2.52~2.47 (m, 1H).

3-[4-Oxo-7-(tetrahydro-pyran-4-yl)-3,4-dihydro-imidazo[5,1-f][1,2,4]triazin-2-yl]-4-trifluoromethyl-pyrrolidine-1-carboxylic acid tert-butyl ester (17)

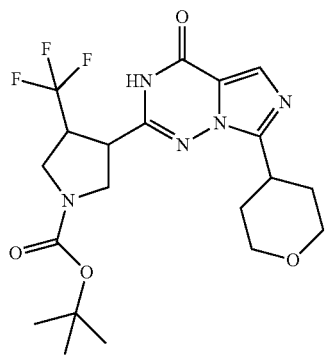 [SMILES: CC(C)(C)OC(=O)N1CC(c2nn3c(C4CCOCC4)ncc3c(=O)[nH]2)C(C(F)(F)F)C1]

The procedure for the preparation of compound 17 was similar to that of compound 8.

27% yield. LC-MS: m/z 458 [M+1]$^+$. $^1$H NMR (400 MHz, CDCl$_3$): δ 7.89 (s, 1H), 4.13~4.03 (m, 3H), 3.89~3.87 (m, 1H), 3.68~3.58 (m, 3H), 3.46~3.39 (m, 1H), 2.14~2.05 (m, 2H), 1.92~1.89 (m, 2H), 1.77~1.59 (m, 3H), 1.47 (s, 9H).

7-(Tetrahydro-pyran-4-yl)-2-(4-trifluoromethyl-pyrrolidin-3-yl)-3H-imidazo[5,1-f][1,2,4]triazin-4-one Hydrochloric acid salt (18)

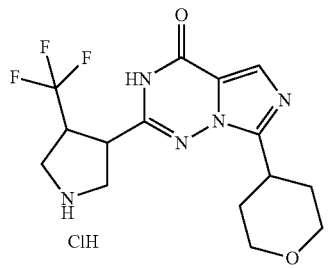 [SMILES: O=c1[nH]c(C2CNCC2C(F)(F)F)nn2c(C3CCOCC3)ncc12 ; Cl]

The procedure for the preparation of compound 18 was similar to that of compound 9.

100% yield. LC-MS: m/z 358 [M+1]$^+$. $^1$H NMR (400 MHz, DMSO-d6): δ 7.90 (br. s, 1H), 3.96~3.93 (m, 3H), 3.75~3.70 (m, 3H), 3.56~3.50 (m, 5H), 1.87~1.82 (m, 4H).

Scheme 5

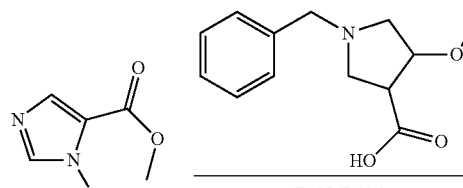

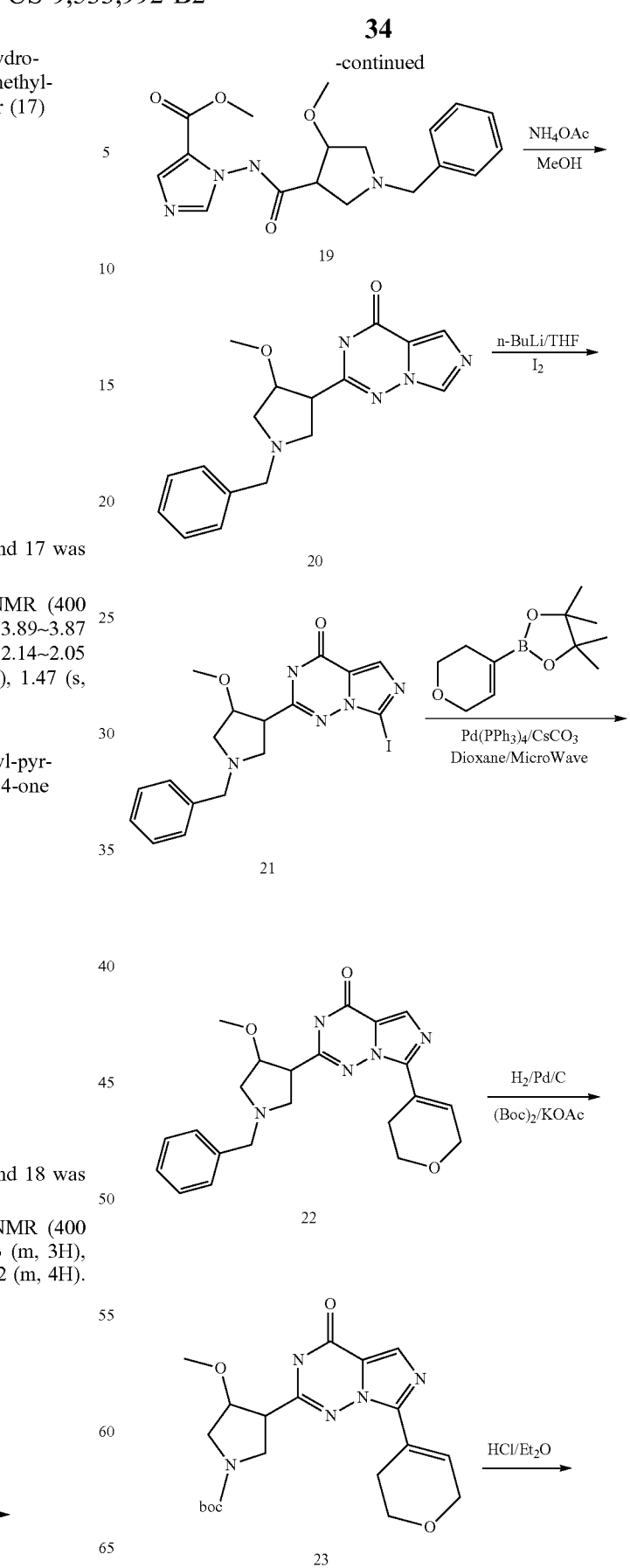

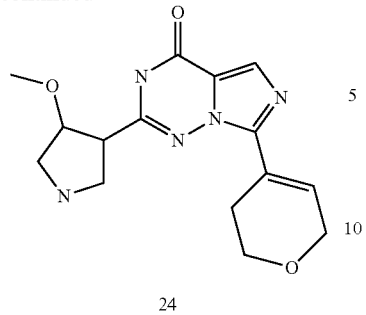

24

3-[(1-Benzyl-4-methoxy-pyrrolidine-3-carbonyl)-amino]-3H-imidazole-4-carboxylic acid methyl ester (19)

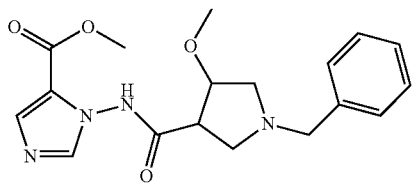 [SMILES: COC(=O)c1cncn1NC(=O)C1CN(Cc2ccccc2)CC1OC]

The procedure for the preparation of compound 19 was similar to that of compound 4.

77% yield. LC-MS (ESI): m/z=359.1 [M+1]$^+$. $^1$H NMR (400 MHz, CDCl$_3$): δ 7.70 (d, J=0.4 Hz, 1H), 7.64 (d, J=0.8 Hz, 1H), 7.33~7.27 (m, 5H), 4.22~4.19 (m, 1H), 3.80 (s, 3H), 3.76 (d, J=6.8 Hz, 2H), 3.45~3.41 (m, 1H), 3.37 (s, 3H), 3.25~3.22 (m, 1H), 2.98~2.95 (m, 1H), 2.74~2.69 (m, 1H), 2.40~2.37 (m, 1H).

2-(1-Benzyl-4-methoxy-pyrrolidin-3-yl)-3H-imidazo[5,1-f][1,2,4]triazin-4-one (20)

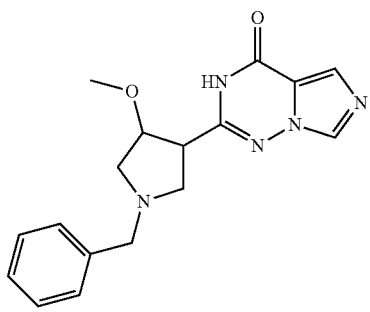 [SMILES: COC1CN(Cc2ccccc2)CC1c1nn2cncc2c(=O)[nH]1]

The procedure for the preparation of compound 20 was similar to that of compound 5.

32% yield. LC-MS (ESI): m/z=325.3 [M+1]$^+$. 1H NMR (300 MHz, CDCl$_3$): δ 8.05 (s, 1H), 7.87 (s, 1H), 7.38~7.30 (m, 5H), 4.00~3.96 (m, 1H), 3.86 (d, J=12.6 Hz, 1H), 3.62 (d, J=12.6 Hz, 1H), 3.57~3.53 (m, 1H), 3.38 (s, 3H), 3.14~3.12 (m, 1H), 3.02~2.99 (m, 1H), 2.74~2.68 (m, 1H), 2.36~2.31 (m, 1H).

2-(1-Benzyl-4-methoxy-pyrrolidin-3-yl)-7-iodo-3H-imidazo[5,1-f][1,2,4]triazin-4-one (21)

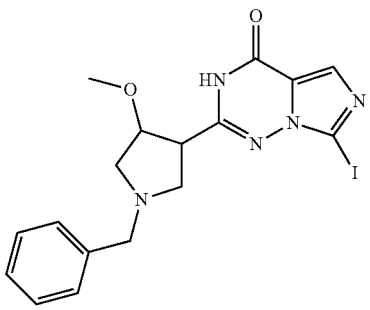 [SMILES: COC1CN(Cc2ccccc2)CC1c1nn2c(I)ncc2c(=O)[nH]1]

The procedure for the preparation of compound 21 was similar to that of compound 6.

38% yield. LC-MS (ESI): m/z=452.2 [M+1]$^+$. 1H NMR (300 MHz, CDCl$_3$): δ 7.91 (s, 1H), 7.40~7.30 (m, 5H), 4.00~3.96 (m, 1H), 3.88~3.84 (m, 1H), 3.66~3.49 (m, 2H), 3.40 (s, 3H), 3.24~3.22 (m, 1H), 3.03~2.99 (m, 1H), 2.74~2.69 (m, 1H), 2.37~2.32 (m, 1H).

2-(1-Benzyl-4-methoxy-pyrrolidin-3-yl)-7-(3,6-dihydro-2H-pyran-4-yl)-3H-imidazo[5,1-f][1,2,4]triazin-4-one (22)

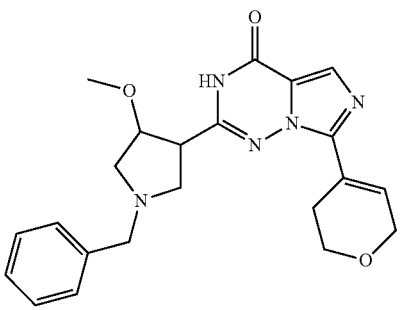 [SMILES: COC1CN(Cc2ccccc2)CC1c1nn2c(C3=CCOCC3)ncc2c(=O)[nH]1]

The procedure for the preparation of compound 22 was similar to that of compound 7.

85% yield. LC-MS (ESI): m/z=408 [M+1]$^+$. $^1$H NMR (400 MHz, CDCl$_3$): δ 7.91 (s, 1H), 7.40~7.29 (m, 5H), 7.21 (m, 1H), 4.39~4.38 (m, 2H), 4.00~3.97 (m, 1H), 3.95~3.92 (m, 2H), 3.87~3.84 (m, 1H), 3.65~3.62 (m, 1H), 3.55~3.49 (m, 2H), 3.40~3.37 (s, 3H), 3.17~3.14 (m, 1H), 3.03~3.00 (m, 1H), 2.78~2.70 (m, 2H), 2.36~2.32 (m, 1H).

3-Methoxy-4-[4-oxo-7-(tetrahydro-pyran-4-yl)-3,4-dihydro-imidazo[5,1-f][1,2,4]triazin-2-yl]-pyrrolidine-1-carboxylic acid tert-butyl ester (23)

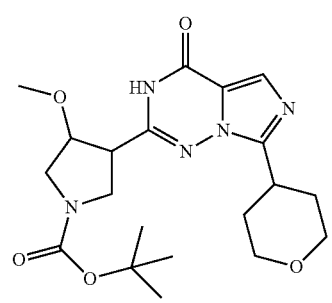 [SMILES: COC1CN(C(=O)OC(C)(C)C)CC1c1nn2c(C3CCOCC3)ncc2c(=O)[nH]1]

The procedure for the preparation of compound 23 was similar to that of compound 8.

46% yield. LC-MS (ESI): m/z=420 [M+1]⁺. ¹H NMR (400 MHz, CDCl₃): δ 7.84 (s, 1H), 4.10~4.06 (m, 2H), 3.96~3.80 (m, 2H), 3.61~3.54 (m, 2H), 3.48 (s, 3H), 3.42~3.31 (m, 1H), 3.31~3.22 (m, 2H), 2.09~2.03 (m, 2H), 2.02~1.89 (m, 2H), 1.62~1.58 (m, 2H), 1.49 (s, 9H).

2-(4-Methoxy-pyrrolidin-3-yl)-7-(tetrahydro-pyran-4-yl)-3H-imidazo[5,1-f][1,2,4]triazin-4-one Hydrochloric acid salt (24)

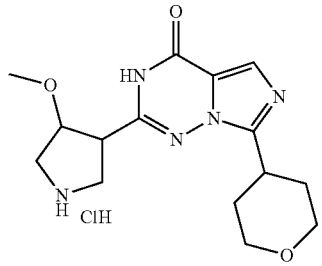 [SMILES: COC1CNCC1c1nn2c(C3CCOCC3)ncc2c(=O)[nH]1 ; Cl]

The procedure for the preparation of compound 24 was similar to that of compound 9.

100% yield. LC-MS (ESI): m/z=320.2 [M+1]⁺. ¹H NMR (400 MHz, DMSO-d6): δ 9.77~9.62 (br. s, 2H), 7.88 (s, 1H), 4.40~4.35 (m, 1H), 3.95~3.91 (m, 2H), 3.69~3.49 (m, 6H), 3.36 (s, 3H), 1.85~1.79 (m, 4H), 1.30~1.23 (m, 1H), 1.11~1.05 (m, 1H).

Preparation of Target Compounds:

Example 1

2-[1-(4-Fluoro-benzyl)-4-methyl-pyrrolidin-3-yl]-7-(tetrahydro-pyran-4-yl)-3H-imidazo[5,1-f][1,2,4]triazin-4-one

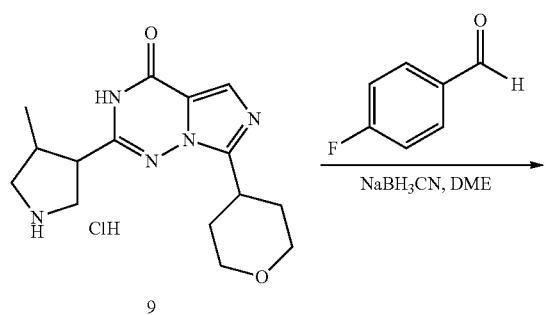

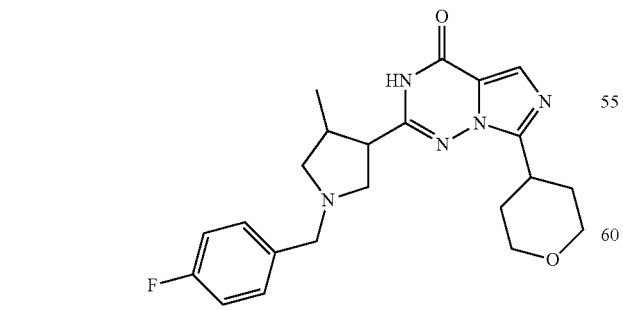

To a solution of compound 9 (80 mg, 0.263 mmol) and 4-fluorobenzaldehyde (326 mg, 2.63 mmol) in 1,2-dichloroethane (15 mL) was added 2 drops of acetic acid. The resulting solution was stirred at room temperature for one hour. Then NaBH₃CN (178 mg, 2.63 mmol) was added to the reaction in portions. The resulting mixture was stirred at room temperature for 16 hours. LC-MS showed that the starting material was almost consumed. The reaction mixture was quenched with water (40 mL), and extracted with CH₂Cl₂ (30 mL×3). The combined organic phases were washed with brine (30 mL), and dried over Na₂SO₄. After filtered, the filtrate was concentrated in vacuum. The residue was purified by preparative TLC to afford the desired product (20 mg, 21% yield) as a white solid. LC-MS: m/z 412.2 [M+1]⁺. ¹H NMR (400 MHz, CD₃OD-d4): δ 8.27 (s, 1H), 7.61 (s, 1H), 7.35~7.31 (m, 2H), 7.02~6.98 (m, 2H), 3.96~3.93 (m, 2H), 3.79~3.70 (m, 2H), 3.51~3.39 (m, 3H), 3.15~3.11 (m, 1H), 3.05~2.95 (m, 2H), 2.84~2.79 (m, 1H), 2.61~2.57 (m, 1H), 2.33~2.29 (m, 1H), 1.93~1.87 (m, 2H), 1.80~1.77 (m, 2H), 1.09 (d, J=6.8 Hz, 3H).

The racemic mixture of 2-[1-(4-Fluoro-benzyl)-4-methyl-pyrrolidin-3-yl]-7-(tetrahydro-pyran-4-yl)-3H-imidazo[5,1-f][1,2,4]triazin-4-one was submitted for preparative chiral HPLC (Column=chiralcel OJ-H; Mobile phase=n-Hexane/EtOH 70/30; Flow rate=12 mL/min; UV: 230 nm; 30 mg/inj in) and give two enantiomers:

2-((3S,4S)-1-(4-fluorobenzyl)-4-methylpyrrolidin-3-yl)-7-(tetrahydro-2H-pyran-4-yl)imidazo[1,5-f][1,2,4]triazin-4(3H)-one

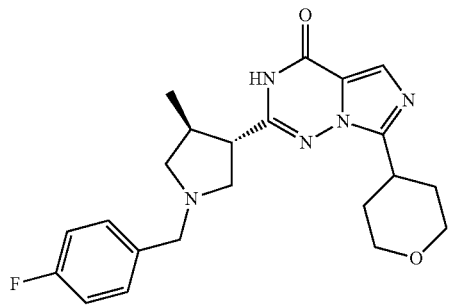 [SMILES: C[C@@H]1CN(Cc2ccc(F)cc2)C[C@H]1c1nn2c(C3CCOCC3)ncc2c(=O)[nH]1]

30% yield. Chiral analytical HPLC (Column=chiralcel OJ-H; Mobile phase=n-Hexane/EtOH 70/30; Flow rate=1.0 mL/min): T_R=7.03. LC-MS: m/z 412.2 [M+1]⁺. ¹H NMR (400 MHz, CDCl₃): δ 7.79 (s, 1H), 7.34~7.31 (m, 2H), 7.07~7.03 (m, 2H), 4.11~4.05 (m, 2H), 3.79~3.76 (d, J=12.8 Hz, 1H), 3.62~3.53 (m, 3H), 3.41~3.35 (m, 2H), 2.97~2.95 (d, J=10.4 Hz, 1H), 2.76~2.74 (m, 1H), 2.52~2.48 (m, 1H), 2.43~2.41 (m, 1H), 2.10~2.02 (m, 2H), 1.93~1.86 (m, 3H), 1.09 (d, J=6.8 Hz, 3H).

2-((3R,4R)-1-(4-fluorobenzyl)-4-methyl pyrrolidin-3-yl)-7-(tetrahydro-2H-pyran-4-yl)imidazo[1,5-f][1,2,4]triazin-4(3H)-one

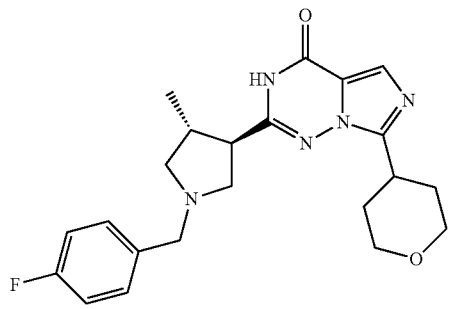 [SMILES: C[C@H]1CN(Cc2ccc(F)cc2)C[C@@H]1c1nn2c(C3CCOCC3)ncc2c(=O)[nH]1]

30% yield. Chiral analytical HPLC (Column=chiralcel OJ-H; Mobile phase=n-Hexane/EtOH 70/30; Flow rate=1.0 mL/min): $T_R$=9.03. LC-MS: m/z 412.2 [M+1]$^+$. $^1$H NMR (400 MHz, CDCl$_3$): δ 7.78 (s, 1H), 7.33~7.30 (m, 2H), 7.06~7.02 (m, 2H), 4.10~4.05 (m, 2H), 3.78~3.74 (d, J=12.8 Hz, 1H), 3.60~3.52 (m, 3H), 3.41~3.36 (m, 2H), 2.98~2.95 (d, J=10.0 Hz, 1H), 2.76~2.73 (m, 1H), 2.52~2.49 (m, 1H), 2.43~2.41 (m, 1H), 2.08~2.01 (m, 2H), 1.93~1.85 (m, 3H), 1.09 (d, J=6.4 Hz, 3H).

The following compounds were prepared in a similar way:

7-(4-fluorophenyl)-2-(1-(4-methoxybenzyl)-4-methylpyrrolidin-3-yl)imidazo[1,5-f][1,2,4]triazin-4(3H)-one

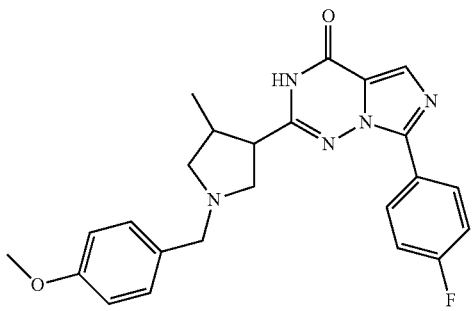 [SMILES: COc1ccc(CN2CC(C)C(c3nn4c(-c5ccc(F)cc5)ncc4c(=O)[nH]3)C2)cc1]

42% yield. LC-MS: m/z 434.2 [M+1]$^+$. $^1$H NMR (400 MHz, CD$_3$OD-d4): δ 8.25~8.22 (m, 2H), 7.78 (s, 1H), 7.23~7.15 (m, 4H), 6.85~6.82 (m, 2H), 3.72 (s, 3H), 3.69 (m, 2H), 3.13 (m, 1H), 3.06~3.02 (m, 1H), 2.98~2.88 (m, 1H), 2.86~2.84 (m, 1H), 2.62~2.59 (m, 1H), 2.30~2.26 (m, 1H), 1.12 (d, J=6.8 Hz, 3H).

7-(4-Fluoro-phenyl)-2-[4-methyl-1-(6-trifluoromethyl-pyridin-3-ylmethyl)-pyrrolidin-3-yl]-3H-imidazo[5,1-f][1,2,4]triazin-4-one

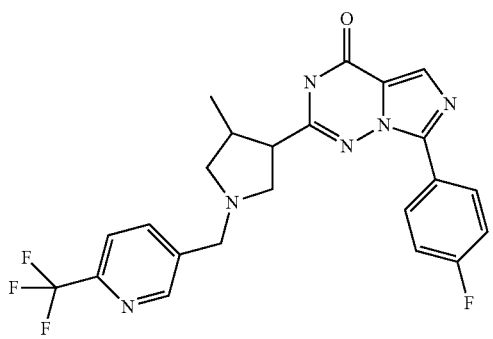 [SMILES: CC1CN(Cc2ccc(C(F)(F)F)nc2)CC1c1nn2c(-c3ccc(F)cc3)ncc2c(=O)[nH]1]

29% yield. LC-MS: m/z 473.2 [M+1]$^+$. $^1$H NMR (400 MHz, CDCl$_3$): δ 8.67 (br. s, 1H), 8.36~8.32 (m, 2H), 8.00~7.96 (m, 1H), 7.96 (s, 1H), 7.77~7.75 (d, J=8.0 Hz, 1H), 7.19~7.15 (m, 2H), 3.87~3.79 (m, 2H), 3.42~3.48 (m, 1H), 3.09~3.06 (d, J=10.0 Hz, 1H), 2.90~2.87 (m, 1H), 2.68~2.64 (m, 1H), 2.51~2.49 (m, 1H), 2.01~1.97 (dd, J=8.4, 9.2 Hz, 1H), 1.25 (d, J=6.8 Hz, 3H).

2-[1-(6-Methoxy-pyridin-3-ylmethyl)-4-methyl-pyrrolidin-3-yl]-7-(tetrahydro-pyran-4-yl)-3H-imidazo[5,1-f][1,2,4]triazin-4-one

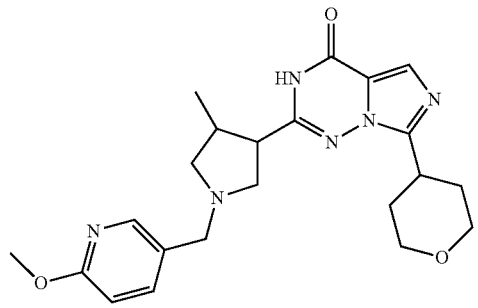 [SMILES: COc1ccc(CN2CC(C)C(c3nn4c(C5CCOCC5)ncc4c(=O)[nH]3)C2)cn1]

23% yield, LC-MS: m/z 425.2 [M+1]$^+$. $^1$H NMR (400 MHz, CD$_3$OD-d4): δ 8.22 (br. s, 1H), 7.92 (s, 1H), 7.78 (dd, J=2.4, 8.4 Hz, 1H), 6.80 (d, J=8.4 Hz, 1H), 4.42~4.27 (m, 2H), 3.96~3.94 (m, 2H), 3.89 (s, 3H), 3.84~3.81 (m, 2H), 3.68~3.64 (m, 2H), 3.64~3.56 (m, 2H), 3.20 (m, 2H), 2.85~2.82 (m, 1H), 1.98~1.85 (m, 4H), 1.18 (d, J=6.4 Hz, 3H).

2-[4-Methyl-1-(6-trifluoromethyl-pyridin-3-ylmethyl)-pyrrolidin-3-yl]-7-(tetrahydro-pyran-4-yl)-3H-imidazo[5,1-f][1,2,4]triazin-4-one

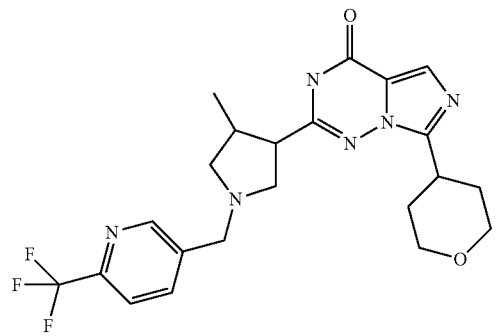 [SMILES: CC1CN(Cc2ccc(C(F)(F)F)nc2)CC1c1nn2c(C3CCOCC3)ncc2c(=O)[nH]1]

18% yield, LC-MS: m/z 463.2 [M+1]$^+$. 1H NMR (400 MHz, CDCl$_3$): δ 8.66 (s, 1H), 7.98 (d, J=8.0 Hz, 1H), 7.81 (s, 1H), 7.76 (d, J=8.0 Hz, 1H), 4.11~4.06 (m, 2H), 3.87~3.84 (d, J=13.2 Hz, 1H), 3.78~3.74 (d, J=13.2 Hz, 1H), 3.62~3.54 (m, 2H), 3.36~3.41 (m, 2H), 3.04~3.02 (d, J=9.6 Hz, 1H), 2.83~2.81 (m, 1H), 2.63 (m, 1H), 2.54 (m, 1H), 2.11~2.09 (m, 1H), 2.07~1.98 (m, 2H), 1.90~1.88 (m, 2H), 1.25 (d, J=6.8 Hz, 3H).

2-[1-(6-Methoxy-pyridin-2-ylmethyl)-4-methyl-pyrrolidin-3-yl]-7-(tetrahydro-pyran-4-yl)-3H-imidazo[5,1-f][1,2,4]triazin-4-one

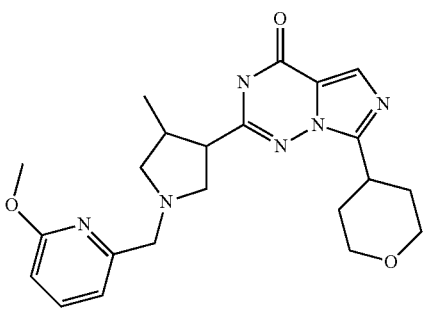 [SMILES: COc1cccc(CN2CC(C)C(c3nn4c(C5CCOCC5)ncc4c(=O)[nH]3)C2)n1]

9% yield, LC-MS: m/z 425.2 [M+1]⁺. ¹H NMR (400 MHz, CD₃OD-d4): δ 7.59 (s, 1H), 7.53~7.51 (m, 1H), 6.89 (d, J=7.2 Hz, 1H), 6.58 (d, J=8.0 Hz, 1H), 3.95~3.92 (m, 2H), 3.82 (s, 3H), 3.73~3.62 (m, 2H), 3.52~3.46 (m, 3H), 3.19~3.15 (m, 1H), 3.05~3.03 (m, 1H), 2.93~2.91 (m, 1H), 2.78 (m, 1H), 2.54 (m, 1H), 2.25~2.23 (m, 1H), 1.92~1.87 (m, 2H), 1.81~1.78 (m, 2H), 1.09 (d, J=6.8 Hz, 3H).

7-(4-Fluoro-phenyl)-2-[1-(6-methoxy-pyridin-2-ylmethyl)-4-methyl-pyrrolidin-3-yl]-3H-imidazo[5,1-f][1,2,4]triazin-4-one

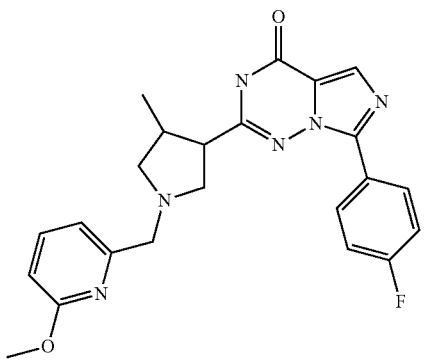 [SMILES: COc1cccc(CN2CC(C)C(c3nn4c(-c5ccc(F)cc5)ncc4c(=O)[nH]3)C2)n1]

47% yield. LC-MS: m/z 435.2 [M+1]⁺. ¹H NMR (400 MHz, CDCl₃): δ 8.29 (m, 2H), 7.87 (s, 1H), 7.48 (m, 1H), 7.09 (m, 2H), 6.81 (m, 1H), 6.58 (m, 1H), 3.91 (s, 3H), 3.85~3.77 (m, 1H), 3.62~3.59 (m, 1H), 3.42~3.38 (m, 1H), 3.07 (m, 1H), 2.77 (m, 1H), 2.60 (m, 1H), 2.40 (m, 1H), 1.95 (m, 1H), 1.09 (d, J=6.8 Hz, 3H).

7-(4-Fluoro-phenyl)-2-[1-(6-methoxy-pyridin-3-ylmethyl)-4-methyl-pyrrolidin-3-yl]-3H-imidazo[5,1-f][1,2,4]triazin-4-one

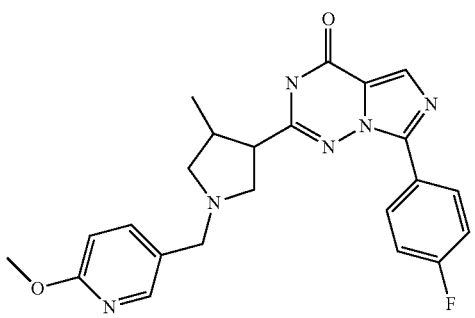 [SMILES: COc1ccc(CN2CC(C)C(c3nn4c(-c5ccc(F)cc5)ncc4c(=O)[nH]3)C2)cn1]

22% yield. LC-MS: m/z 435.2 [M+1]⁺. ¹H NMR (400 MHz, CDCl₃): δ 8.36~8.33 (m, 2H), 8.07 (d, J=1.2 Hz, 1H), 7.95 (s, 1H), 7.68~7.65 (dd, J=2.4, 8.4 Hz, 1H), 7.18~7.14 (m, 2H), 6.80 (d, J=8.4 Hz, 1H), 3.93 (s, 3H), 3.74~3.70 (d, J=12.8 Hz, 1H), 3.60~3.57 (d, J=12.8 Hz, 1H), 3.40~3.36 (m, 1H), 3.05~3.02 (d, J=10.4 Hz, 1H), 2.82 (m, 1H), 2.56 (m, 1H), 1.95~1.91 (m, 2H), 1.14 (d, J=6.8 Hz, 3H).

7-(4-Fluoro-phenyl)-2-(4-methyl-1-pyridin-2-ylmethyl-pyrrolidin-3-yl)-3H-imidazo[5,1-f][1,2,4]triazin-4-one

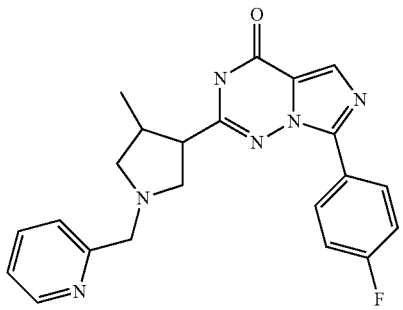 [SMILES: CC1CN(Cc2ccccn2)CC1c1nn2c(-c3ccc(F)cc3)ncc2c(=O)[nH]1]

49% yield. LC-MS: m/z 405.2 [M+1]⁺. ¹H NMR (400 MHz, CD₃OD-d4): δ 8.44 (d, J=4.4 Hz, 1H), 8.24~8.22 (m, 2H), 7.77 (s, 1H), 7.73~7.69 (m, 1H), 7.41 (d, J=8.0 Hz, 1H), 7.24~7.21 (m, 1H), 7.17~7.12 (m, 2H), 3.84~3.73 (m, 2H), 3.12~3.10 (m, 1H), 3.04~3.00 (m, 1H), 2.94~2.89 (m, 1H), 2.85~2.81 (m, 1H), 2.61~2.59 (m, 1H), 2.26~2.22 (t, J=8.4 Hz, 1H), 1.10 (d, J=6.8 Hz, 3H).

2-[1-(2,4-Difluoro-benzyl)-4-methyl-pyrrolidin-3-yl]-7-(tetrahydro-pyran-4-yl)-3H-imidazo[5,1-f][1,2,4]triazin-4-one

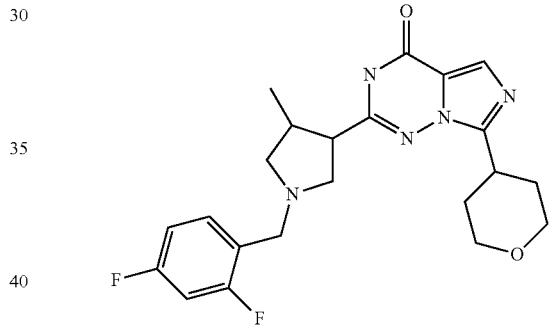

88% yield. LC-MS: m/z 387.1 [M+1]⁺. ¹H NMR (400 MHz, CD₃OD-d4): δ 7.73 (s, 1H), 7.52~7.46 (m, 1H), 6.96~7.01 (m, 2H), 4.08~4.05 (m, 2H), 3.79 (s, 2H), 3.65~3.55 (m, 3H), 3.18~3.14 (m, 1H), 3.03~2.97 (m, 2H), 2.88 (m, 1H), 2.69~2.62 (m, 1H), 2.29 (m, 1H), 2.06~1.97 (m, 2H), 1.93~1.90 (m, 2H), 1.20 (d, J=6.8 Hz, 3H).

2-(3S,4S)-[1-(2,4-Difluoro-benzyl)-4-methyl-pyrrolidin-3-yl]-7-(tetrahydro-pyran-4-yl)-3H-imidazo[5,1-f][1,2,4]triazin-4-one

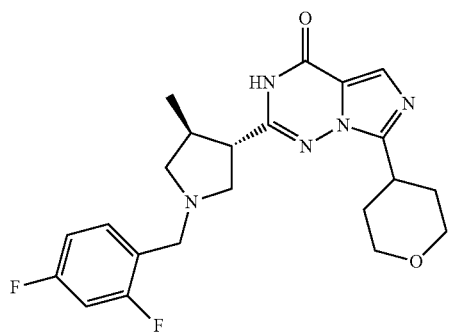 [SMILES: C[C@@H]1CN(Cc2ccc(F)cc2F)C[C@H]1c1nn2c(C3CCOCC3)ncc2c(=O)[nH]1]

16% yield. Chiral analytical HPLC (Column=chiralcel AD; Mobile phase=CO$_2$/MeOH/DEA 80/20/0.02 (v/v/v); Flow rate=2.5 mL/min): T$_R$=1.43. LC-MS: m/z 430.2 [M+1]$^+$. $^1$H NMR (400 MHz, CDCl$_3$): δ 7.79 (s, 1H), 7.34~7.30 (m, 1H), 6.91~6.83 (m, 2H), 4.11~4.05 (m, 2H), 3.75~3.62 (m, 2H), 3.62~3.55 (m, 2H), 3.41~3.33 (m, 2H), 3.01 (d, J=9.6 Hz, 1H), 2.76~2.74 (m, 1H), 2.59~2.55 (m, 1H), 2.42~2.40 (m, 1H), 2.12~2.02 (m, 2H), 1.95~1.86 (m, 3H), 1.21 (d, J=6.8 Hz, 3H).

2-(3R,4R)-[1-(2,4-difluoro-benzyl)-4-methyl-pyrrolidin-3-yl]-7-(tetrahydro-pyran-4-yl)-3H-imidazo[5,1-f][1,2,4]triazin-4-one

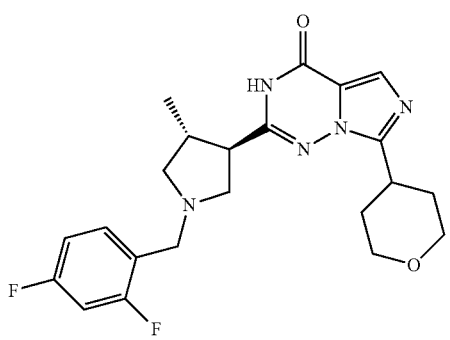 [SMILES: C[C@H]1CN(Cc2ccc(F)cc2F)C[C@@H]1c1nn2c(C3CCOCC3)ncc2c(=O)[nH]1]

16% yield. Chiral analytical HPLC (Column=chiralcel AD; Mobile phase=CO$_2$/IPA/DEA 60/40/0.04 (v/v/v); Flow rate=2.4 mL/min): T$_R$=3.81. LC-MS: m/z 430.2 [M+1]$^+$. $^1$H NMR (300 MHz, CDCl$_3$): δ 7.80 (s, 1H), 7.36~7.27 (m, 1H), 6.93~6.84 (m, 2H), 4.11~4.08 (m, 2H), 3.77~3.76 (m, 2H), 3.63~3.56 (m, 2H), 3.43~3.34 (m, 2H), 3.01 (d, J=10.2 Hz, 1H), 2.77~2.76 (m, 1H), 2.61~2.58 (m, 1H), 2.44~2.40 (m, 1H), 2.15~2.03 (m, 2H), 1.97~1.87 (m, 3H), 1.22 (d, J=10.0 Hz, 3H).

2-(1-(4-fluorobenzyl)-4-methylpyrrolidin-3-yl)-7-(4-fluorophenyl)imidazo[1,5-f][1,2,4]triazin-4(3H)-one

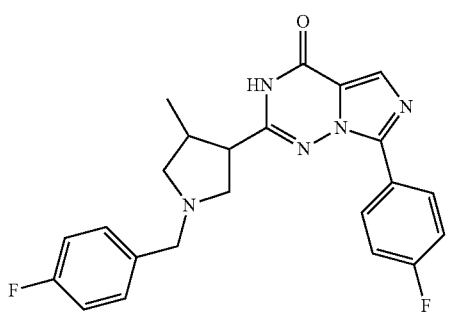 [SMILES: CC1CN(Cc2ccc(F)cc2)CC1c1nn2c(-c3ccc(F)cc3)ncc2c(=O)[nH]1]

39% yield. LC-MS: m/z 422.1 [M+1]$^+$. $^1$H NMR (400 MHz, DMSO-d6): δ 8.41~8.38 (m, 2H), 7.87 (s, 1H), 7.40~7.32 (m, 4H), 7.15~7.10 (m, 2H), 3.62 (s, 2H), 2.98 (m, 1H), 2.88~2.78 (m, 2H), 2.71~2.67 (m, 1H), 2.30~2.26 (m, 1H), 2.01~1.97 (m, 1H), 1.12 (d, J=6.8 Hz, 3H).

2-(4-methyl-1-(4-(trifluoromethoxy)benzyl)pyrrolidin-3-yl)-7-(tetrahydro-2H-pyran-4-yl)imidazo[1,5-f][1,2,4]triazin-4(3H)-one

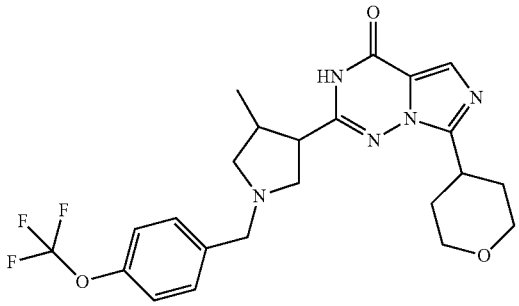 [SMILES: CC1CN(Cc2ccc(OC(F)(F)F)cc2)CC1c1nn2c(C3CCOCC3)ncc2c(=O)[nH]1]

36% yield. LC-MS: m/z 478 [M+1]$^+$. $^1$H NMR (400 MHz, CDCl$_3$): δ 7.74 (s, 1H), 7.32 (d, J=8.4 Hz, 2H), 7.14 (d, J=8.4 Hz, 2H), 4.00 (m, 2H), 3.73 (d, J=12.8 Hz, 1H), 3.57~3.48 (m, 3H), 3.35~3.30 (m, 2H), 2.95 (d, J=10.0 Hz, 1H), 2.73~2.71 (m, 1H), 2.40 (m, 1H), 2.38 (m, 1H), 1.89~1.82 (m, 5H), 1.15 (d, J=6.8 Hz, 3H).

2-(1-(2-chloro-4-methoxybenzyl)-4-methylpyrrolidin-3-yl)-7-(tetrahydro-2H-pyran-4-yl)imidazo[1,5-f][1,2,4]triazin-4(3H)-one

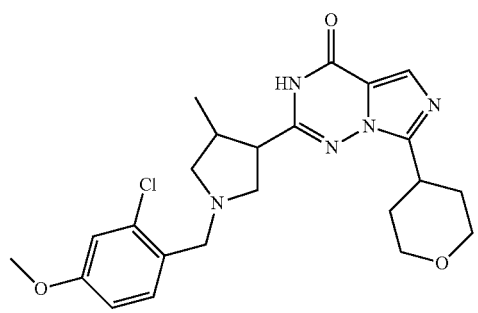 [SMILES: COc1ccc(CN2CC(C)C(c3nn4c(C5CCOCC5)ncc4c(=O)[nH]3)C2)c(Cl)c1]

27% yield. LC-MS: m/z 458.2 [M+1]$^+$. 1H NMR (400 MHz, CDCl$_3$): δ 7.77 (s, 1H), 7.25 (d, J=8.4 Hz, 1H), 6.97 (d, J=2.8 Hz, 1H), 6.82~6.79 (dd, J=8.4, 2.8 Hz, 1H), 4.08~4.05 (m, 2H), 3.79 (s, 3H), 3.79~3.61 (m, 2H), 3.61~3.55 (m, 2H), 3.44~3.00 (m, 2H), 3.02 (m, 1H), 2.76~2.74 (m, 1H), 2.62~2.58 (m, 1H), 2.42~2.37 (m, 1H), 2.15~2.00 (m, 2H), 1.99~1.86 (m, 3H), 1.26 (d, J=12.4 Hz, 3H).

2-(4-methyl-1-(quinoxalin-6-ylmethyl)pyrrolidin-3-yl)-7-(tetrahydro-2H-pyran-4-yl)imidazo[1,5-f][1,2,4]triazin-4(3H)-one

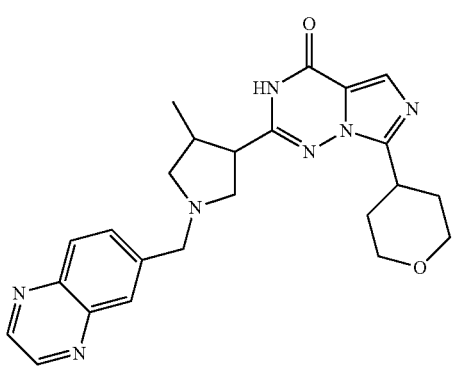 [SMILES: CC1CN(Cc2ccc3nccnc3c2)CC1c1nn2c(C3CCOCC3)ncc2c(=O)[nH]1]

30% yield. LC-MS: m/z 446 [M+1]+. 1H NMR (400 MHz, CDCl3): δ 8.10 (d, J=8.4 Hz, 1H), 7.96 (s, 1H), 7.85 (d, J=8.4 Hz, 1H), 7.72 (s, 1H), 4.02~3.88 (m, 3H), 3.88~3.86 (m, 1H), 3.53~3.46 (m, 2H), 3.43~3.29 (m, 2H), 3.05 (m, 1H), 2.77 (m, 1H), 2.67 (m, 1H), 2.46 (m, 1H), 2.09~1.91 (m, 3H), 1.83~1.78 (m, 2H), 1.19 (d, J=6.8 Hz, 3H).

2-[1-(5-Methoxy-2-methyl-penta-2,4-dienyl)-4-methyl-pyrrolidin-3-yl]-7-(tetrahydro-pyran-4-yl)-3H-imidazo[5,1-f][1,2,4]triazin-4-one

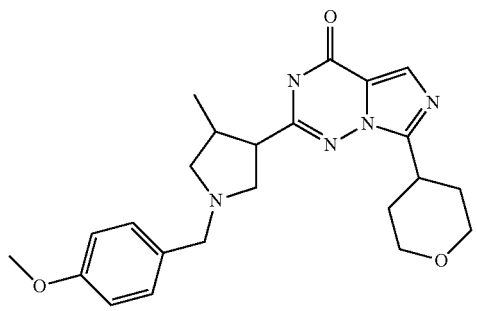 [SMILES: COc1ccc(CN2CC(C)C(c3nn4c(C5CCOCC5)ncc4c(=O)[nH]3)C2)cc1]

20% yield. LC-MS: m/z 424.2 [M+1]+. 1H NMR (400 MHz, CDCl3): δ 7.79 (s, 1H), 7.27 (d, J=8.4 Hz, 2H), 6.89 (d, J=8.4 Hz, 2H), 4.11~4.05 (m, 2H), 3.79 (s, 3H), 3.78 (m, 1H), 3.61~3.55 (m, 2H), 3.50~3.36 (m, 3H), 2.97~2.94 (d, J=10.0 Hz, 1H), 2.73 (m, 1H), 2.49~2.41 (m, 2H), 2.13~2.02 (m, 3H), 1.92~1.86 (m, 2H), 1.20 (d, J=6.8 Hz, 3H).

2-(4-methyl-1-(pyridin-4-ylmethyl)pyrrolidin-3-yl)-7-(tetrahydro-2H-pyran-4-yl)imidazo[1,5-f][1,2,4]triazin-4(3H)-one

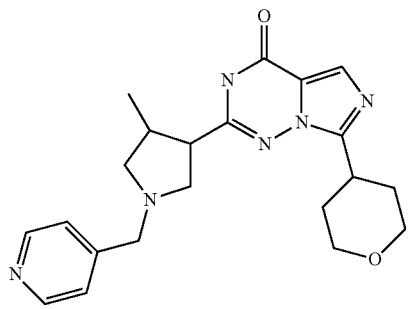 [SMILES: CC1CN(Cc2ccncc2)CC1c1nn2c(C3CCOCC3)ncc2c(=O)[nH]1]

12% yield. LC-MS: m/z 395.2 [M+1]+. 1H NMR (400 MHz, CDCl3): δ 8.60 (d, J=5.2 Hz, 2H), 7.82 (s, 1H), 7.29 (d, J=5.2 Hz, 2H), 4.11 (m, 2H), 3.81 (d, J=13.6 Hz, 1H), 3.65~3.55 (m, 3H), 3.44~3.38 (m, 3H), 3.03 (d, J=10.0 Hz, 1H), 2.81~2.79 (m, 1H), 2.60~2.55 (m, 1H), 2.48~2.45 (m, 1H), 2.16~2.03 (m, 2H), 1.97~1.74 (m, 3H), 1.24 (d, J=6.0 Hz, 3H)

2-(4-Methyl-1-pyridin-2-ylmethyl-pyrrolidin-3-yl)-7-(tetrahydro-pyran-4-yl)-3H-imidazo[5,1-f][1,2,4]triazin-4-one

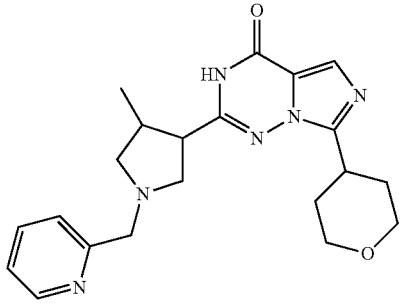 [SMILES: CC1CN(Cc2ccccn2)CC1c1nn2c(C3CCOCC3)ncc2c(=O)[nH]1]

7% yield. LC-MS: m/z 395.2 [M+1]+. 1H NMR (400 MHz, CD3OD-d4): δ 8.43 (d, J=4.8 Hz, 1H), 7.75~7.70 (m, 1H), 7.60 (s, 1H), 7.40 (d, J=8.0 Hz, 1H), 7.24~7.21 (m, 1H), 3.93 (m, 2H), 3.82~3.71 (m, 2H), 3.52~3.46 (m, 2H), 3.10~3.05 (m, 1H), 2.98~2.94 (m, 1H), 2.87~2.76 (m, 2H), 2.56~2.53 (m, 1H), 2.21~2.17 (m, 1H), 1.93~1.87 (m, 2H), 1.81~1.78 (m, 2H), 1.07 (d, J=7.2 Hz, 3H).

2-(4-methyl-1-(pyrimidin-5-yl methyl)pyrrolidin-3-yl)-7-(tetrahydro-2H-pyran-4-yl)imidazo[1,5-f][1,2,4]triazin-4(3H)-one

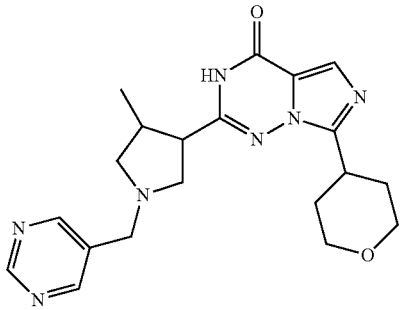 [SMILES: CC1CN(Cc2cncnc2)CC1c1nn2c(C3CCOCC3)ncc2c(=O)[nH]1]

44% yield. LC-MS: m/z 396.2 [M+1]+. 1H NMR (400 MHz, CDCl3): δ 9.17 (br. s, 1H), 8.75 (s, 2H), 7.79 (s, 1H), 4.09~4.05 (m, 2H), 3.73 (s, 2H), 3.61~3.54 (m, 2H), 3.47~3.31 (m, 2H), 3.06 (d, J=6.0 Hz, 1H), 2.83~2.80 (m, 1H), 2.66~2.61 (dd, J=10.0, 7.2 Hz, 1H), 2.47~2.44 (m, 1H), 2.12~1.96 (m, 2H), 1.94~1.74 (m, 3H), 1.25 (d, J=6.8 Hz, 3H).

2-[1-(4-Diethylamino-benzyl)-4-methyl-pyrrolidin-3-yl]-7-(tetrahydro-pyran-4-yl)-3H-imidazo[5,1-f][1,2,4]triazin-4-one

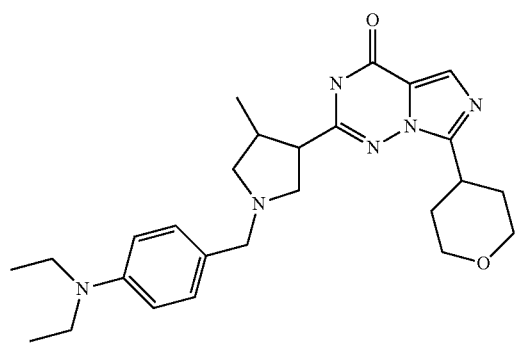 [SMILES: CCN(CC)c1ccc(CN2CC(C)C(c3nn4c(C5CCOCC5)ncc4c(=O)[nH]3)C2)cc1]

35% yield. LC-MS: m/z 465.3 [M+1]$^+$. $^1$H NMR (400 MHz, CDCl$_3$): δ 7.78 (s, 1H), 7.17 (d, J=8.4 Hz, 2H), 6.65 (d, J=8.4 Hz, 2H), 4.11~4.05 (m, 2H), 3.76~3.73 (d, J=12.4 Hz, 1H), 3.62~3.55 (m, 2H), 3.49~3.30 (m, 7H), 2.98 (d, J=10.0 Hz, 1H), 2.70 (m, 1H), 2.46~2.39 (m, 2H), 2.15~1.81 (m, 5H), 1.19 (d, J=7.2 Hz, 3H), 1.16~1.13 (t, J=7.2 Hz, 6H).

2-(1-(furan-2-ylmethyl)-4-methylpyrrolidin-3-yl)-7-(tetrahydro-2H-pyran-4-yl)imidazo[1,5-f][1,2,4]triazin-4(3H)-one

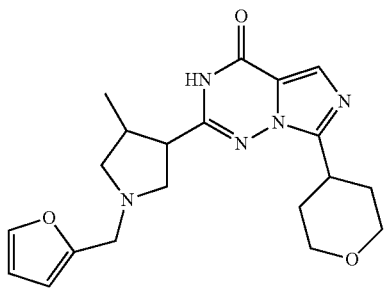 [SMILES: CC1CN(Cc2ccco2)CC1c1nn2c(C3CCOCC3)ncc2c(=O)[nH]1]

35% yield. LC-MS: m/z 384.2 [M+1]$^+$. 1H NMR (400 MHz, CDCl$_3$): δ 7.80 (s, 1H), 7.41 (d, J=2.0 Hz, 1H), 6.34 (dd, J=2.0, 2.8 Hz, 1H), 6.26 (d, J=2.8 Hz, 1H), 4.11~4.07 (m, 2H), 3.88~3.84 (d, J=14.0 Hz, 1H), 3.67~3.56 (m, 3H), 3.45~3.37 (m, 2H), 3.03 (d, J=10.0 Hz, 1H), 2.77~2.74 (m, 1H), 2.61~2.58 (m, 1H), 2.45~2.42 (m, 1H), 2.14~1.98 (m, 3H), 1.92~1.88 (m, 2H), 1.21 (d, J=7.2 Hz, 3H)

2-(1-((1H-imidazol-2-yl)methyl)-4-methylpyrrolidin-3-yl)-7-(tetrahydro-2H-pyran-4-yl)imidazo[1,5-f][1,2,4]triazin-4(3H)-one

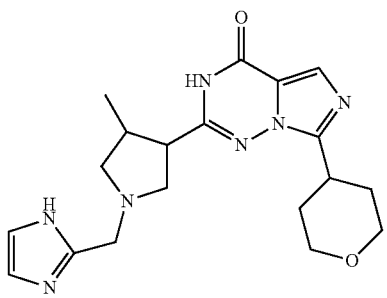 [SMILES: CC1CN(Cc2ncc[nH]2)CC1c1nn2c(C3CCOCC3)ncc2c(=O)[nH]1]

5% yield. LC-MS: m/z 384.2 [M+1]$^+$. $^1$H NMR (400 MHz, CD$_3$OD-d4): δ 8.44 (br. s, 2H), 7.75 (s, 1H), 7.11 (s, 1H), 4.08~4.06 (m, 2H), 3.87 (s, 2H), 3.65~3.53 (m, 3H), 3.18~3.14 (dd, J=7.6, 8.8 Hz, 1H), 3.07~3.00 (m, 2H), 2.93~2.88 (m, 1H), 2.73~2.69 (m, 1H), 2.38~2.34 (dd, J=7.6, 9.2 Hz, 1H), 2.07~1.91 (m, 4H), 1.09 (d, J=6.8 Hz, 3H).

2-((3S,4S)-4-methylpyrrolidin-3-yl)-7-(tetrahydro-2H-pyran-4-yl)imidazo[1,5-f][1,2,4]triazin-4(3H)-one

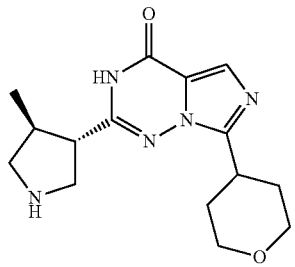 [SMILES: C[C@@H]1CNC[C@H]1c1nn2c(C3CCOCC3)ncc2c(=O)[nH]1]

45% yield. Chiral analytical HPLC (Column=chiralcel OJ-H; Mobile phase=n-Hexane/EtOH/DEA 80/20:0.3; Flow rate=1.0 mL/min): T$_R$=7.44. LC-MS: m/z=304.2 [M+1]$^+$. $^1$H NMR (400 MHz, CD$_3$OD-d4): δ 7.49 (s, 1H), 3.96~3.93 (m, 2H), 3.53~3.31 (m, 6H), 2.82~2.77 (m, 1H), 2.69~2.66 (m, 1H), 2.64~2.53 (m, 1H), 1.95~1.88 (m, 2H), 1.82~1.78 (m, 2H), 1.10 (d, J=6.8 Hz, 3H).

2-((3R,4R)-4-methylpyrrolidin-3-yl)-7-(tetrahydro-2H-pyran-4-yl)imidazo[1,5-f][1,2,4]triazin-4(3H)-one

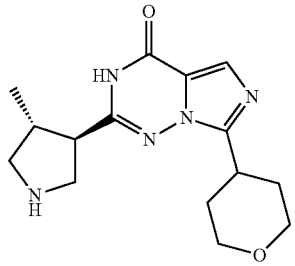 [SMILES: C[C@H]1CNC[C@@H]1c1nn2c(C3CCOCC3)ncc2c(=O)[nH]1]

45% yield. Chiral analytical HPLC (Column=chiralcel OJ-H; Mobile phase=n-Hexane/EtOH/DEA 80/20:0.3; Flow rate=1.0 mL/min): T$_R$=9.93. LC-MS: m/z 304.2 [M+1]$^+$. $^1$H NMR (400 MHz, CD$_3$OD-d4): δ 8.42 (br. s, 2H), 7.63 (s, 1H), 3.97~3.93 (m, 2H), 3.68~3.41 (m, 6H), 3.05~2.99 (m, 1H), 2.96~2.91 (m, 1H), 2.70~2.66 (m, 1H), 1.95~1.90 (m, 2H), 1.82~1.78 (m, 2H), 1.10 (d, J=6.8 Hz, 3H).

4-((3-methyl-4-(4-oxo-7-(tetrahydro-2H-pyran-4-yl)-3,4-dihydroimidazo[1,5-f][1,2,4]triazin-2-yl)pyrrolidin-1-yl)methyl)benzonitrile

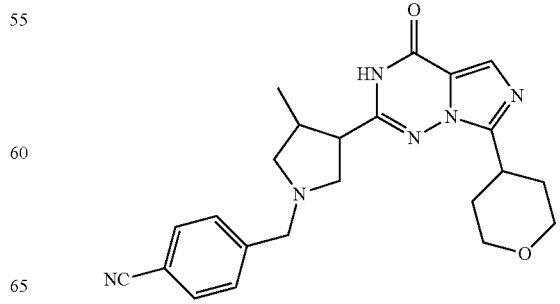

36% yield. LC-MS: m/z 419.2 [M+1]⁺. ¹H NMR (400 MHz, CD₃OD-d4): δ 7.63 (d, J=7.6 Hz, 1H), 7.62 (s, 1H), 7.49 (d, J=7.6 Hz, 2H), 3.96~3.93 (m, 2H), 3.76~3.72 (d, J=13.6 Hz, 1H), 3.70~3.66 (d, J=13.6 Hz, 1H), 3.53~3.40 (m, 3H), 3.05~3.00 (dd, J=8.0, 8.8 Hz, 1H), 2.91~2.84 (m, 2H), 2.80~2.75 (m, 1H), 2.60~2.57 (m, 1H), 2.21~2.17 (m, 1H), 1.95~1.90 (m, 2H), 1.81~1.78 (m, 2H), 1.10 (d, J=6.8 Hz, 3H).

2-(1-(2-chloro-4-fluorobenzyl)-4-methylpyrrolidin-3-yl)-7-(tetrahydro-2H-pyran-4-yl)imidazo[1,5-f][1,2,4]triazin-4(3H)-one

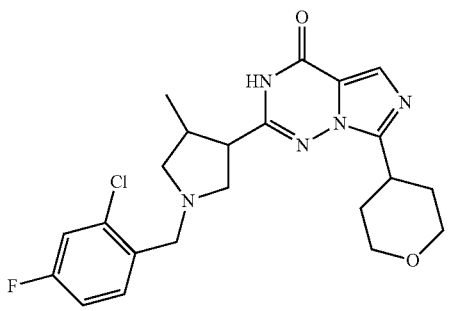 [SMILES: CC1CN(Cc2ccc(F)cc2Cl)CC1c1nn2c(C3CCOCC3)ncc2c(=O)[nH]1]

72% yield. LC-MS: m/z 446 [M+1]⁺. ¹H NMR (400 MHz, CDCl₃): δ 7.77 (s, 1H), 7.35~7.31 (m, 1H), 7.19~7.16 (m, 1H), 7.01~6.99 (m, 1H), 4.10~4.05 (m, 2H), 3.83 (d, J=12.8 Hz, 1H), 3.72 (d, J=12.8 Hz, 1H), 3.61~3.55 (m, 2H), 3.40~3.30 (m, 2H), 3.03 (d, J=10.0 Hz, 1H), 2.77 (m, 1H), 2.65~2.61 (m, 1H), 2.41~2.39 (m, 1H), 2.10~2.03 (m, 2H), 1.95~1.88 (m, 3H), 1.22 (d, J=8.8 Hz, 3H).

2-(1-(4-(di methylamino)benzyl)-4-methyl pyrrolidin-3-yl)-7-(tetrahydro-2H-pyran-4-yl)imidazo[1,5-f][1,2,4]triazin-4(3H)-one

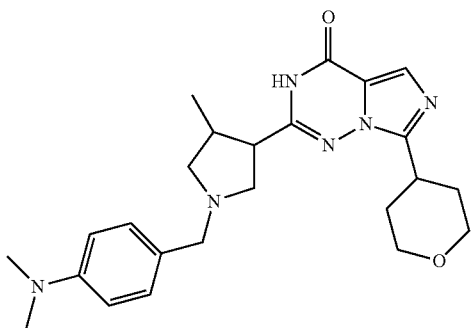 [SMILES: CC1CN(Cc2ccc(N(C)C)cc2)CC1c1nn2c(C3CCOCC3)ncc2c(=O)[nH]1]

25% yield. LC-MS: m/z 437 [M+1]⁺. ¹H NMR (400 MHz, CDCl₃): δ 7.78 (s, 1H), 7.22 (d, J=8.4 Hz, 2H), 6.72 (d, J=8.4 Hz, 2H), 4.10~4.05 (m, 2H), 3.79 (d, J=12.8 Hz, 1H), 3.61~3.55 (m, 2H), 3.45~3.36 (m, 3H), 2.97 (d, J=8.0 Hz, 1H), 2.93 (s, 6H), 2.88 (m, 1H), 2.72 (m, 1H), 2.48~2.40 (m, 2H), 2.12~2.01 (m, 2H), 1.91~1.85 (m, 2H), 1.19 (d, J=6.8 Hz, 3H).

2-(4-methyl-1-(4-methylbenzyl)pyrrolidin-3-yl)-7-(tetrahydro-2H-pyran-4-yl)imidazo[1,5-f][1,2,4]triazin-4(3H)-one

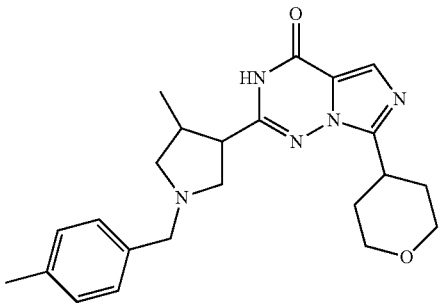 [SMILES: Cc1ccc(CN2CC(C)C(c3nn4c(C5CCOCC5)ncc4c(=O)[nH]3)C2)cc1]

62% yield. LC-MS: m/z 408 [M+1]⁺. ¹H NMR (400 MHz, CDCl₃): δ 8.05 (br. s, 1H), 7.79 (s, 1H), 7.24 (d, J=7.2 Hz, 2H), 7.17 (d, J=7.2 Hz, 2H), 4.10~4.05 (m, 2H), 3.82 (d, J=12.4 Hz, 1H), 3.61~3.55 (m, 2H), 3.51 (d, J=12.8 Hz, 1H), 3.41~3.37 (m, 2H), 2.99 (d, J=10.0 Hz, 1H), 2.74 (d, J=4.4 Hz, 1H), 2.52~2.42 (m, 2H), 2.32 (s, 3H), 2.13~2.01 (m, 2H), 1.95~1.85 (m, 3H), 1.20 (d, J=6.4 Hz, 3H).

2-(1-Cyclohexylmethyl-4-methyl-pyrrolidin-3-yl)-7-(tetrahydro-pyran-4-yl)-3H-imidazo[5,1-f][1,2,4]triazin-4-one

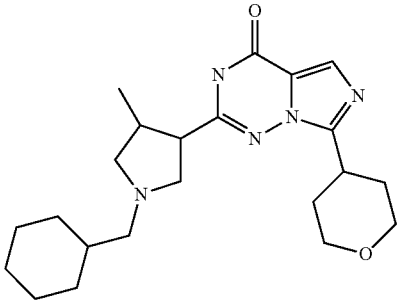 [SMILES: CC1CN(CC2CCCCC2)CC1c1nn2c(C3CCOCC3)ncc2c(=O)[nH]1]

37% yield. LC-MS: m/z 400.2 [M+1]⁺. ¹H NMR (400 MHz, CDCl₃): δ 7.79 (s, 1H), 4.09~4.05 (m, 2H), 3.63~3.59 (m, 2H), 3.43~3.41 (m, 2H), 3.09~3.06 (d, J=11.6 Hz, 1H), 2.75 (m, 1H), 2.41~2.44 (m, 1H), 2.37~2.34 (m, 3H), 2.17~2.01 (m, 2H), 1.90~1.93 (m, 3H), 1.80~1.76 (m, 5H), 1.68~1.65 (m, 1H), 1.46~1.43 (m, 1H), 1.24 (m, 2H), 1.21 (d, J=7.2 Hz, 3H), 0.98 (m, 2H).

2-(4-Methyl-1-pyridin-3-ylmethyl-pyrrolidin-3-yl)-7-(tetrahydro-pyran-4-yl)-3H-imidazo[5,1-f][1,2,4]triazin-4-one

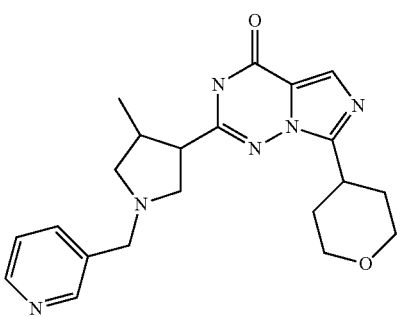 [SMILES: CC1CN(Cc2cccnc2)CC1c1nn2c(C3CCOCC3)ncc2c(=O)[nH]1]

60% yield. LC-MS: m/z 395.2 [M+1]⁺. ¹HNMR (400 MHz, CDCl₃): δ 8.55 (m, 2H), 7.80 (s, 1H), 7.78 (m, 1H), 7.37~7.35 (m, 1H), 4.08 (m, 2H), 3.81~3.78 (d, J=12.8 Hz, 1H), 3.67~3.64 (d, J=12.8 Hz, 1H), 3.62~3.58 (m, 2H), 3.41~3.38 (m, 2H), 2.99 (d, J=10.0 Hz, 1H), 2.79~2.77 (m, 1H), 2.59~2.57 (m, 1H), 2.50~2.40 (m, 1H), 1.99~1.89 (m, 5H), 1.22 (d, J=7.2 Hz, 3H).

2-[1-(2,6-Difluoro-benzyl)-4-methyl-pyrrolidin-3-yl]-7-(tetrahydro-pyran-4-yl)-3H-imidazo[5,1-f][1,2,4]triazin-4-one

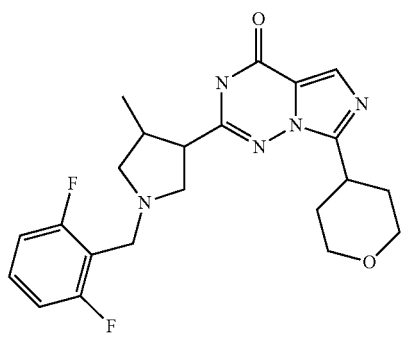 [SMILES: CC1CN(Cc2c(F)cccc2F)CC1c1nn2c(C3CCOCC3)ncc2c(=O)[nH]1]

9% yield. LC-MS: m/z 430.2 [M+1]⁺. ¹H NMR (400 MHz, CDCl₃): δ 7.78 (s, 1H), 7.28 (m, 1H), 6.97~6.94 (t, J=8.0 Hz, 2H), 4.10~4.06 (m, 2H), 3.91 (s, 2H), 3.61~3.55 (m, 2H), 3.40~3.38 (m, 2H), 3.15 (m, 1H), 2.74~2.62 (m, 2H), 2.42 (m, 1H), 2.10~2.02 (m, 3H), 1.90~1.87 (m, 2H), 1.19 (d, J=7.2 Hz, 3H).

2-[4-Methyl-1-(5-methyl-thiophen-2-ylmethyl)-pyrrolidin-3-yl]-7-(tetrahydro-pyran-4-yl)-3H-imidazo[5,1-f][1,2,4]triazin-4-one

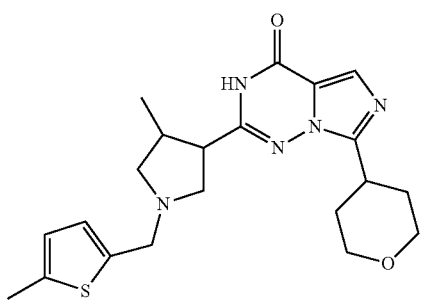 [SMILES: Cc1ccc(CN2CC(C)C(c3nn4c(C5CCOCC5)ncc4c(=O)[nH]3)C2)s1]

15% yield. LC-MS: m/z=414.2 [M+1]⁺. ¹H NMR (300 MHz, CDCl₃): δ 7.81 (s, 1H), 6.73 (d, J=3.3 Hz, 1H), 6.58~6.57 (m, 1H), 4.13~4.06 (m, 2H), 3.97 (d, J=13.5 Hz, 1H), 3.67 (d, J=13.5 Hz, 1H), 3.64~3.55 (m, 2H), 3.48~3.38 (m, 2H), 3.08 (d, J=9.9 Hz, 1H), 2.78~2.75 (m, 1H), 2.53~2.43 (m, 5H), 2.16~1.88 (m, 5H), 1.22 (d, J=7.2 Hz, 3H).

2-[1-(5-Chloro-thiophen-2-yl methyl)-4-methyl-pyrrolidin-3-yl]-7-(tetrahydro-pyran-4-yl)-3H-imidazo[5,1-f][1,2,4]triazin-4-one

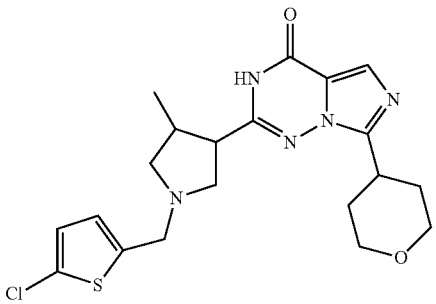 [SMILES: CC1CN(Cc2ccc(Cl)s2)CC1c1nn2c(C3CCOCC3)ncc2c(=O)[nH]1]

20% yield. LC-MS: m/z=434.1 [M+1]⁺. ¹H NMR (400 MHz, CDCl₃): δ 7.81 (s, 1H), 6.77~6.75 (m, 2H), 4.11~4.06 (m, 2H), 3.94 (d, J=14.4 Hz, 1H), 3.69 (d, J=13.2 Hz, 1H), 3.62~3.56 (m 2H), 3.47~3.42 (m, 2H), 3.10 (d, J=10.0 Hz, 1H), 2.79~2.78 (m, 1H), 2.55~2.43 (m, 2H), 2.15~1.96 (m, 2H), 1.92~1.90 (m, 3H), 1.22 (d, J=6.8 Hz, 3H).

2-[4-Methyl-1-(4-pyrrolidin-1-yl-benzyl)-pyrrolidin-3-yl]-7-(tetrahydro-pyran-4-yl)-3H-imidazo[5,1-f][1,2,4]triazin-4-one

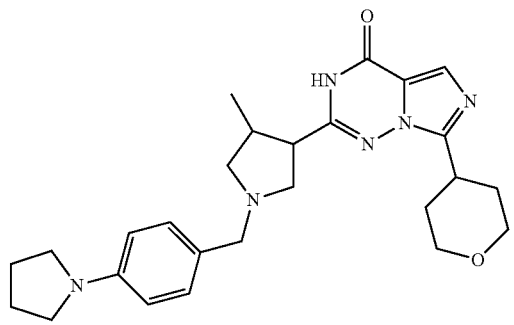 [SMILES: CC1CN(Cc2ccc(N3CCCC3)cc2)CC1c1nn2c(C3CCOCC3)ncc2c(=O)[nH]1]

10% yield. LC-MS: m/z=463.3 [M+1]⁺. ¹H NMR (300 MHz, CDCl₃): δ 7.80 (s, 1H), 7.19 (d, J=8.4 Hz, 2H), 6.54 (d, J=8.7 Hz, 2H), 4.11~4.03 (m, 2H), 3.78 (d, J=12.9 Hz, 1H), 3.62~3.54 (m 2H), 3.44~3.35 (m, 3H), 3.28~3.23 (m, 4H), 2.98~2.95 (m, 1H), 2.72~2.70 (m, 1H), 2.47~2.42 (m, 2H), 2.17~1.85 (m, 9H), 1.19 (d, J=6.9 Hz, 3H).

2-[1-(4-Fluoro-benzyl)-4-methoxy-pyrrolidin-3-yl]-7-(tetrahydro-pyran-4-yl)-3H-imidazo[5,1-f][1,2,4]triazin-4-one

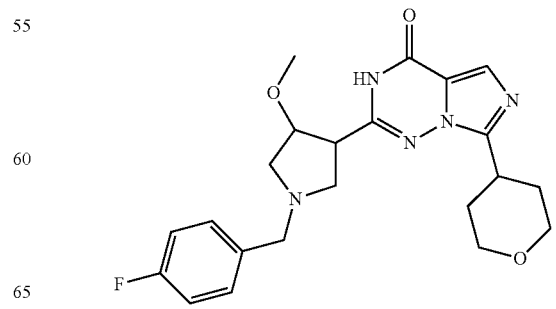

19% yield. LC-MS: m/z=428.2 [M+1]+. 1H NMR (400 MHz, CDCl3): δ 7.81 (s, 1H), 7.34~7.31 (m, 2H), 7.08~7.04 (m, 2H), 4.10~4.07 (m, 2H), 3.99~3.97 (m, 1H), 3.84 (d, J=12.4 Hz, 1H), 3.61~3.50 (m, 4H), 3.39 (s, 3H), 3.16 (d, J=6.4 Hz, 1H), 3.99 (d, J=9.6 Hz, 1H), 2.72~2.69 (m, 1H), 2.35~2.30 (m, 1H), 2.15~2.01 (m, 2H), 1.90~1.88 (m, 2H), 1.25~1.24 (m, 1H).

2-[4-Methoxy-1-(4-methyl-benzyl)-pyrrolidin-3-yl]-7-(tetrahydro-pyran-4-yl)-3H-imidazo[5,1-f][1,2,4]triazin-4-one

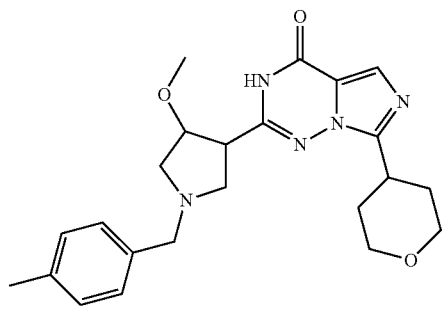 [SMILES: COC1CN(Cc2ccc(C)cc2)CC1c1nn2c(C3CCOCC3)ncc2c(=O)[nH]1]

13% yield. LC-MS: m/z=424.3 [M+1]+. 1H NMR (300 MHz, CDCl3): δ 7.80 (s, 1H), 7.25 (d, J=6.6 Hz, 2H), 7.17 (d, J=7.8 Hz, 2H), 4.09~4.00 (m, 3H), 3.88 (d, J=12.6 Hz, 1H), 3.61~3.53 (m, 4H), 3.44~3.40 (m, 1H), 3.37 (s, 3H), 3.19~3.17 (m, 1H), 3.07~3.03 (m, 1H), 2.77~2.76 (m, 1H), 2.41~2.37 (m, 1H), 2.33 (s, 3H), 2.13~1.99 (m, 2H), 1.90~1.96 (m, 2H).

2-[4-Methoxy-1-(4-methoxy-benzyl)-pyrrolidin-3-yl]-7-(tetrahydro-pyran-4-yl)-3H-imidazo[5,1-f][1,2,4]triazin-4-one

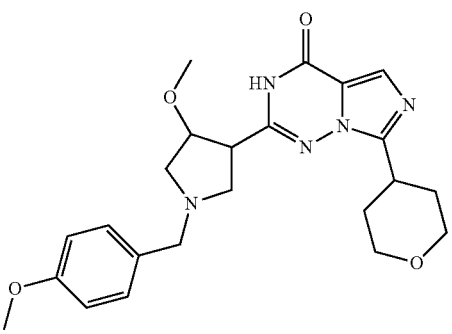 [SMILES: COc1ccc(CN2CC(OC)C(c3nn4c(C5CCOCC5)ncc4c(=O)[nH]3)C2)cc1]

25% yield. LC-MS: m/z=440.1 [M+1]+. 1H NMR (400 MHz, CDCl3): δ 7.81 (s, 1H), 7.27 (d, J=6.0 Hz, 2H), 6.89 (d, J=8.4 Hz, 2H), 4.09~4.07 (m, 2H), 3.99~3.96 (m, 1H), 3.79 (s, 3H), 3.61~3.51 (m, 4H), 3.38 (s, 3H), 3.15~3.13 (m, 1H), 3.00~2.97 (m, 1H), 2.69~2.65 (m, 1H), 2.34~2.30 (m, 1H), 2.13~2.00 (m, 3H), 1.90~1.87 (m, 3H).

Example 2

2-(1-Benzyl-4-methyl-pyrrolidin-3-yl)-7-(tetrahydro-pyran-4-yl)-3H-imidazo[5,1-f][1,2,4]triazin-4-one

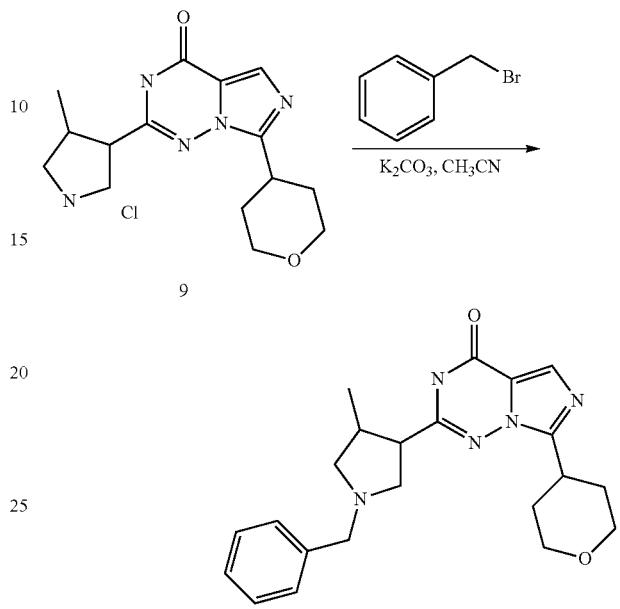

To a solution of compound 6 (70 mg, 0.296 mmol) and potassium carbonate (70 mg, 0.296 mmol) in acetonitrile (10 mL) was added benzyl bromide (70 mg, 0.296 mmol). The resulting solution was stirred at room temperature for 2 h. LC-MS showed that the reaction was complete. The reaction was quenched with water (40 mL), and the reaction mixture was extracted with CH2Cl2 (30 mL×3). The combined organic phases were washed with brine (30 mL), dried over Na2SO4 and concentrated in vacuum. The residue was purified by preparative TLC (CH2Cl2/MeOH=10:1) to afford the desired product (28.6 mg, 25% yield) as a white solid. LC-MS: m/z 394.2 [M+1]+. 1H NMR (400 MHz, CD3OD-d4): δ 7.60 (s, 1H), 7.29~7.22 (m, 4H), 7.19~7.17 (m, 1H), 3.95~3.92 (m, 2H), 3.69~3.58 (m, 2H), 3.52~3.46 (m, 3H), 3.21 (m, 1H), 3.06~3.04 (m, 1H), 2.91~2.76 (m, 2H), 2.58~2.56 (m, 1H), 2.16 (m, 1H), 1.89~1.81 (m, 2H), 1.78 (m, 2H), 1.27 (d, J=6.8 Hz, 3H).

The racemic mixture of 2-(1-Benzyl-4-methyl-pyrrolidin-3-yl)-7-(tetrahydro-pyran-4-yl)-3H-imidazo[5,1-f][1,2,4]triazin-4-one was submitted for preparative chiral HPLC (Column=chiralpak OD-H; Mobile phase=n-Hexane/EtOH 70/30; Flow rate=25 mL/min; UV: 230 nm; 30 mg/inj in) and gave two enantiomers:

2-((3S,4S)-1-benzyl-4-methylpyrrolidin-3-yl)-7-(tetrahydro-2H-pyran-4-yl)imidazo[1,5-f][1,2,4]triazin-4(3H)-one

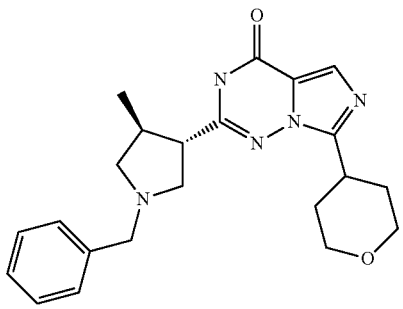 [SMILES: C[C@@H]1CN(Cc2ccccc2)C[C@H]1c1nn2c(C3CCOCC3)ncc2c(=O)[nH]1]

80% yield. Chiral analytical HPLC (Column=chiralpak OD-H; Mobile phase=n-Hexane/EtOH 70/30; Flow rate=1.0 mL/min): $T_R$=5.85. LC-MS: m/z 394.2 [M+I]$^+$. $^1$H NMR (400 MHz, CD$_3$OD-d4): δ 7.79 (s, 1H), 7.37~7.35 (m, 4H), 7.31~7.29 (m, 1H), 4.11~4.05 (m, 2H), 3.84~3.81 (d, J=12.4 Hz, 1H), 3.62~3.55 (m, 3H), 3.43~3.38 (m, 2H), 2.99~2.96 (d, J=10.4 Hz, 1H), 2.75~2.73 (m, 1H), 2.53~2.48 (m, 1H), 2.43~2.41 (m, 1H), 2.13~2.02 (m, 2H), 1.95~1.86 (m, 3H), 1.21 (d, J=7.2 Hz, 3H).

2-((3R,4R)-1-benzyl-4-methylpyrrolidin-3-yl)-7-(tetrahydro-2H-pyran-4-yl)imidazo[1,5-f][1,2,4]triazin-4(3H)-one

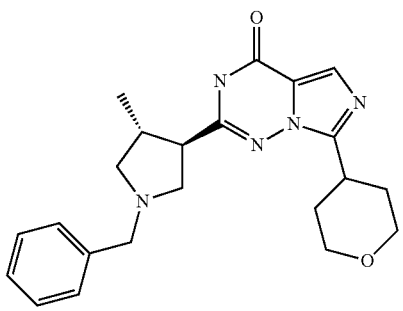 [SMILES: C[C@H]1CN(Cc2ccccc2)C[C@@H]1c1nn2c(C3CCOCC3)ncc2c(=O)[nH]1]

80% yield. Chiral analytical HPLC (Column=chiralpak OD-H; Mobile phase=n-Hexane/EtOH 70/30; Flow rate=1.0 mL/min): $T_R$=7.57. LC-MS: m/z 394.2 [M+I]$^+$. $^1$H NMR (400 MHz, CD$_3$OD-d4): δ 7.79 (s, 1H), 7.37~7.35 (m, 4H), 7.31~7.26 (m, 1H), 4.11~4.05 (m, 2H), 3.84~3.81 (d, J=12.4 Hz, 1H), 3.62~3.55 (m, 3H), 3.43~3.37 (m, 2H), 2.99~2.96 (d, J=10.0 Hz, 1H), 2.75~2.73 (m, 1H), 2.53~2.48 (m, 1H), 2.43~2.41 (m, 1H), 2.13~2.02 (m, 2H), 1.95~1.85 (m, 3H), 1.21 (d, J=7.2 Hz, 3H).

The following compounds were prepared in a similar way:

7-(4-Fluoro-phenyl)-2-(4-methyl-1-pyrimidin-2-ylmethyl-pyrrolidin-3-yl)-3H-imidazo[5,1-f][1,2,4]triazin-4-one

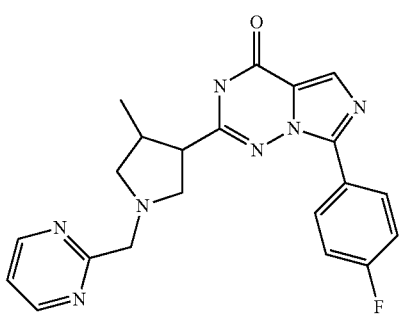

40% yield. LC-MS: m/z 405.9 [M+1]$^+$. $^1$H NMR (400 MHz, CD$_3$OD-d4): δ 8.76 (d, J=4.8 Hz, 2H), 8.15 (m, 2H), 7.84 (s, 1H), 7.42 (t, J=4.8 Hz, 1H), 7.20~7.16 (d, J=8.8 Hz, 2H), 4.62~4.47 (m, 3H), 4.01~3.91 (m, 3H), 3.30~3.20 (m, 1H), 2.94~2.86 (m, 1H), 1.24 (d, J=6.4 Hz, 3H).

7-(4-fluorophenyl)-2-((3S,4S)-4-methyl-1-(pyrimidin-2-yl methyl)pyrrolidin-3-yl)imidazo[1,5-f][1,2,4]triazin-4(3H)-one

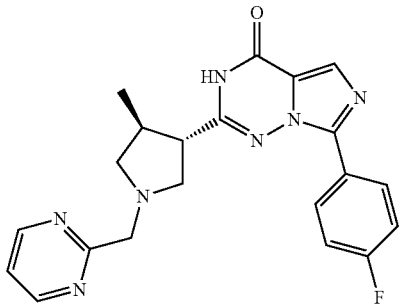 [SMILES: C[C@@H]1CN(Cc2ncccn2)C[C@H]1c1nn2c(-c3ccc(F)cc3)ncc2c(=O)[nH]1]

30% yield. Chiral analytical HPLC (Column=chiralcel OJ-H; Mobile phase=n-Hexane/EtOH 70/30; Flow rate=1.0 mL/min): $T_R$=7.68. LC-MS: m/z 406.2 [M+1]$^+$. $^1$H NMR (400 MHz, MeOH-d4): δ 8.74 (d, J=5.2 Hz, 2H), 8.28~8.25 (m, 2H), 7.78 (s, 1H), 7.32 (m, 1H), 7.18 (m, 2H), 4.04 (d, J=15.2 Hz, 1H), 4.87 (d, J=15.2 Hz, 1H), 3.19 (m, 2H), 2.89~2.82 (m, 3H), 2.31 (m, 1H), 1.11 (d, J=6.8 Hz, 3H).

7-(4-fluorophenyl)-2-((3R,4R)-4-methyl-1-(pyrimidin-2-ylmethyl)pyrrolidin-3-yl)imidazo[1,5-f][1,2,4]triazin-4(3H)-one

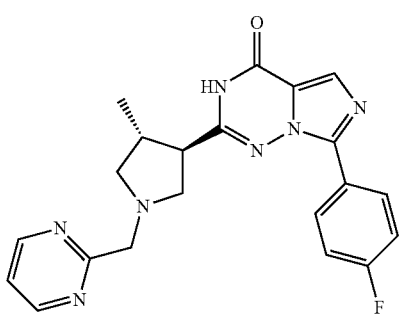 [SMILES: C[C@H]1CN(Cc2ncccn2)C[C@@H]1c1nn2c(-c3ccc(F)cc3)ncc2c(=O)[nH]1]

30% yield. Chiral analytical HPLC (Column=chiralcel OJ-H; Mobile phase=n-Hexane/EtOH 70/30; Flow rate=1.0 mL/min): $T_R$=9.39. LC-MS: m/z 406.2 [M+1]$^+$. $^1$H NMR (400 MHz, MeOH-d4): δ 8.74 (d, J=4.8 Hz, 2H), 8.28~8.25 (m, 2H), 7.78 (s, 1H), 7.32 (m, 1H), 7.18 (m, 2H), 4.04 (d, J=15.6 Hz, 1H), 4.87 (d, J=15.6 Hz, 1H), 3.19 (m, 2H), 2.89~2.82 (m, 3H), 2.31 (m, 1H), 1.11 (d, J=6.8 Hz, 3H).

2-(4-Methyl-1-pyrimidin-2-ylmethyl-pyrrolidin-3-yl)-7-(tetrahydro-pyran-4-yl)-3H-imidazo[5,1-f][1,2,4]triazin-4-one

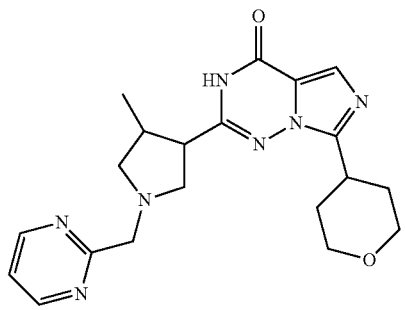 [SMILES: CC1CN(Cc2ncccn2)CC1c1nn2c(C3CCOCC3)ncc2c(=O)[nH]1]

33% yield. LC-MS: m/z 396.2 [M+1]⁺. ¹H NMR (400 MHz, CD₃OD-d4): δ 8.73 (d, J=5.2 Hz, 2H), 7.62 (s, 1H), 7.30 (t, J=4.8 Hz, 1H), 4.08~4.04 (d, J=15.6 Hz, 1H), 3.96~3.86 (m, 3H), 3.54~3.44 (m, 3H), 3.26~3.15 (m, 2H), 2.85~2.82 (m, 2H), 2.52 (m, 1H), 2.30~2.28 (m, 1H), 1.92~1.89 (m, 2H), 1.88~1.79 (m, 2H), 1.11 (d, J=7.2 Hz, 3H).

2-((3S,4S)-4-methyl-1-(pyrimidin-2-yl methyl)pyrrolidin-3-yl)-7-(tetrahydro-2H-pyran-4-yl)imidazo[1,5-f][1,2,4]triazin-4(3H)-one

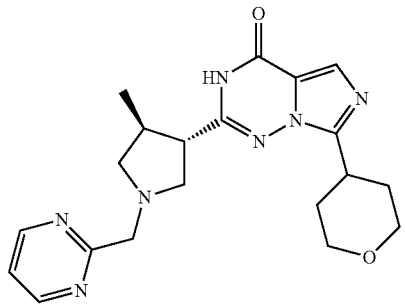 [SMILES: C[C@@H]1CN(Cc2ncccn2)C[C@H]1c1nn2c(C3CCOCC3)ncc2c(=O)[nH]1]

29% yield. Chiral analytical HPLC (Column=chiralcel OJ-H; Mobile phase=n-Hexane/EtOH 70/30; Flow rate=1.0 mL/min): T$_R$=6.63. LC-MS: m/z 396 [M+1]⁺. ¹H NMR (400 MHz, CDCl₃): δ 8.84 (d, J=4.8 Hz, 2H), 7.81 (s, 1H), 7.23 (t, J=4.8 Hz, 1H), 4.30 (d, J=16.8 Hz, 1H), 4.07 (m, 2H), 3.87 (d, J=16.8 Hz, 1H), 3.64~3.57 (m, 2H), 3.51~3.44 (m, 2H), 3.26 (d, J=10.0 Hz, 1H), 2.83~2.81 (m, 1H), 2.63~2.60 (m, 1H), 2.51~2.48 (m, 1H), 2.30~2.26 (m, 1H), 2.12~2.05 (m, 2H), 1.95~1.89 (m, 2H), 1.27 (d, J=7.2 Hz, 3H).

2-((3R,4R)-4-methyl-1-(pyrimidin-2-ylmethyl)pyrrolidin-3-yl)-7-(tetrahydro-2H-pyran-4-yl)imidazo[1,5-f][1,2,4]triazin-4(3H)-one

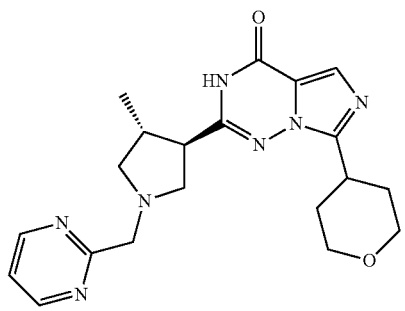 [SMILES: C[C@H]1CN(Cc2ncccn2)C[C@@H]1c1nn2c(C3CCOCC3)ncc2c(=O)[nH]1]

29% yield. Chiral analytical HPLC (Column=chiralcel OJ-H; Mobile phase=n-Hexane/EtOH 70/30; Flow rate=1.0 mL/min): T$_R$=8.13. LC-MS: m/z 396 [M+1]⁺. ¹H NMR (400 MHz, CDCl₃): δ 8.84 (d, J=4.8 Hz, 2H), 7.81 (s, 1H), 7.23 (t, J=4.8 Hz, 1H), 4.30 (d, J=16.8 Hz, 1H), 4.07 (m, 2H), 3.87 (d, J=16.8 Hz, 1H), 3.64~3.57 (m, 2H), 3.51~3.44 (m, 2H), 3.26 (d, J=10.0 Hz, 1H), 2.83~2.81 (m, 1H), 2.62~2.58 (m, 1H), 2.49~2.47 (m, 1H), 2.29~2.25 (m, 1H), 2.12~2.05 (m, 2H), 1.95~1.89 (m, 2H), 1.27 (d, J=7.2 Hz, 3H).

2-(1-Benzyl-4-methoxy-pyrrolidin-3-yl)-7-(tetrahydro-pyran-4-yl)-3H-imidazo[5,1-f][1,2,4]triazin-4-one

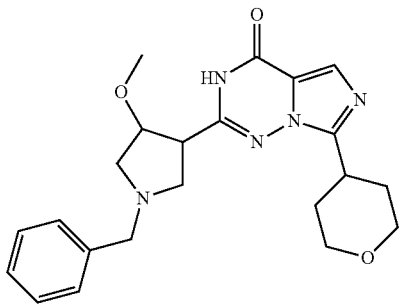 [SMILES: COC1CN(Cc2ccccc2)CC1c1nn2c(C3CCOCC3)ncc2c(=O)[nH]1]

32% yield. LC-MS: m/z=410.2 [M+1]⁺. ¹H NMR (300 MHz, CDCl₃): δ 7.86 (s, 1H), 7.46~7.43 (m, 5H), 4.77~4.71 (m, 1H), 4.53~4.35 (m, 2H), 4.23~4.18 (m, 1H), 4.07~4.04 (m, 2H), 3.81~3.71 (m, 3H), 3.56~3.46 (m, 2H), 3.42 (s, 3H), 3.38~3.31 (m, 2H), 2.10~2.01 (m, 1H), 1.88~1.83 (m, 2H).

2-(3S,4S)-(1-Benzyl-4-methoxy-pyrrolidin-3-yl)-7-(tetrahydro-pyran-4-yl)-3H-imidazo[5,1-f][1,2,4]triazin-4-one

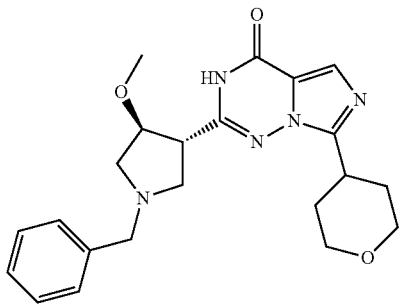 [SMILES: CO[C@@H]1CN(Cc2ccccc2)C[C@H]1c1nn2c(C3CCOCC3)ncc2c(=O)[nH]1]

40% yield. Chiral analytical HPLC (Column=chiralcel AD-H; Mobile phase=n-Hexane/EtOH 60/40; Flow rate=0.6 mL/min): T$_R$=10.8. LC-MS m/z=410.2 [M+1]⁺. ¹H NMR (400 MHz, CDCl₃): δ 7.81 (s, 1H), 7.40~7.34 (m, 5H), 4.10~4.07 (m, 2H), 4.00~3.97 (m, 1H), 3.88 (d, J=12.4 Hz, 1H), 3.62~3.53 (m, 4H), 3.44~3.37 (m, 4H), 3.15 (d, J=6.4 Hz, 1H), 2.99 (d, J=10.0 Hz, 1H), 2.72~2.68 (m, 1H), 2.36~2.32 (m, 1H), 2.13~2.03 (m, 2H), 1.91~1.87 (m, 2H).

2-(3R,4R)-(1-Benzyl-4-methoxy-pyrrolidin-3-yl)-7-(tetrahydro-pyran-4-yl)-3H-imidazo[5,1-f][1,2,4]triazin-4-one

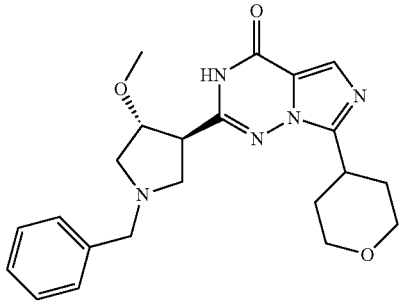 [SMILES: CO[C@H]1CN(Cc2ccccc2)C[C@@H]1c1nn2c(C3CCOCC3)ncc2c(=O)[nH]1]

40% yield. Chiral analytical HPLC (Column=chiralcel AD-H; Mobile phase=n-Hexane/EtOH 60/40; Flow rate=0.6 mL/min): $T_R$=11.9. LC-MS: m/z=410.2 [M+1]$^+$. $^1$H NMR (400 MHz, CDCl$_3$): δ 7.81 (s, 1H), 7.39~7.29 (m, 5H), 4.10~4.07 (m, 2H), 3.99~3.96 (m, 1H), 3.88 (d, J=12.4 Hz, 1H), 3.62~3.52 (m, 4H), 3.41~3.38 (m, 4H), 3.15 (d, J=6.0 Hz, 1H), 2.99 (d, J=10.0 Hz, 1H), 2.72~2.68 (m, 1H), 2.36~2.32 (m, 1H), 2.13~2.03 (m, 2H), 1.91~1.87 (m, 2H).

2-(4-Methyl-1-pyrimidin-4-ylmethyl-pyrrolidin-3-yl)-7-(tetrahydro-pyran-4-yl)-3H-imidazo[5,1-f][1,2,4]triazin-4-one

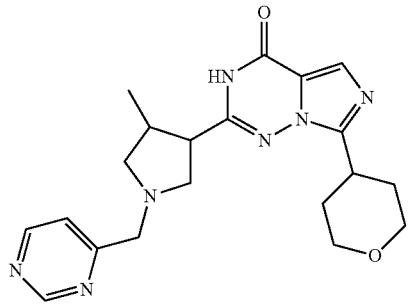 [SMILES: CC1CN(Cc2ccncn2)CC1c1nn2c(C3CCOCC3)ncc2c(=O)[nH]1]

5% yield. LC-MS: m/z=396.2 [M+1]$^+$. $^1$H NMR (400 MHz, CD$_3$OD-d4): δ 9.15 (s, 1H), 8.74 (d, J=5.2 Hz, 1H), 7.73 (s, 1H), 7.60 (d, J=6.0 Hz, 1H), 4.07~4.04 (m, 2H), 3.98 (d, J=15.2 Hz, 1H), 3.87 (d, J=15.2 Hz, 1H), 3.64~3.55 (m, 3H), 3.24~3.20 (m, 1H), 3.13~3.12 (m, 1H), 3.01~2.97 (m, 1H), 2.93~2.88 (m, 1H), 2.70~2.66 (m, 1H), 2.38~2.34 (m, 1H), 2.06~1.99 (m, 2H), 1.92~1.89 (m, 2H), 1.21 (d, J=6.8 Hz, 3H).

Example 3

2-(1-Benzyl-4-methyl-pyrrolidin-3-yl)-7-pyridin-3-yl-3H-imidazo[5,1-f][1,2,4]triazin-4-one

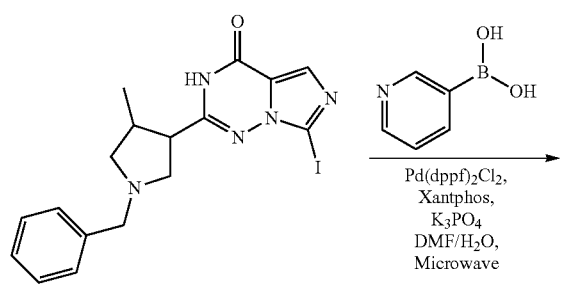

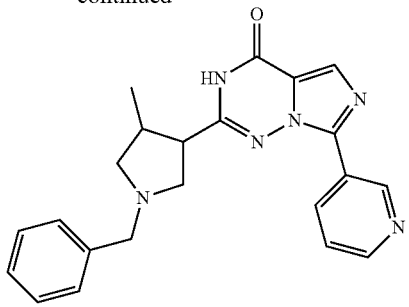

The procedure for the preparation of this compound was similar to that of compound 7.

60% yield. LC-MS: m/z 387.1 [M+1]$^+$. $^1$H NMR (400 MHz, CD$_3$OD-d4): δ 9.37 (br. s, 1H), 8.60 (d, J=8.0 Hz, 1H), 8.51 (m, 1H), 7.97 (br. s, 1H), 7.89 (m, 1H), 7.81 (s, 1H), 7.50~7.47 (m, 1H), 7.30~7.14 (m, 4H), 3.74~3.65 (m, 2H), 3.12~3.09 (m, 1H), 3.01~2.92 (m, 2H), 2.85~2.81 (m, 1H), 2.63~2.60 (m, 1H), 2.26~2.23 (m, 1H), 1.11 (d, J=6.4 Hz, 3H).

2-(1-benzyl-4-methylpyrrolidin-3-yl)-7-(4-(trifluoromethoxy)phenyl)imidazo[1,5-f][1,2,4]triazin-4(3H)-one

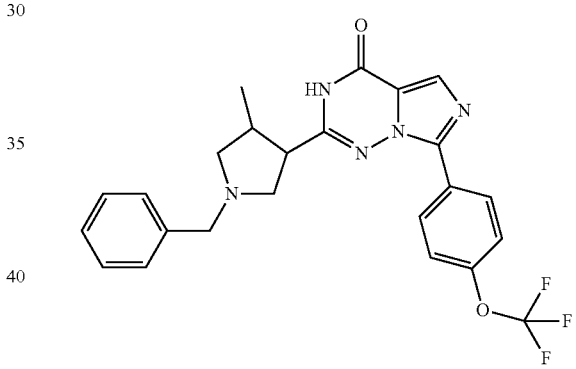

47% yield. LC-MS: m/z 470.2 [M+H]$^+$. $^1$H NMR (400 MHz, DMSO-d6): δ 8.49 (d, J=9.2 Hz, 2H), 7.90 (s, 1H), 7.54~7.52 (d, J=8.0 Hz, 2H), 7.34~7.28 (m, 3H), 7.25~7.23 (m, 1H), 3.64 (s, 2H), 2.99~2.87 (m, 3H), 2.85~2.82 (m, 1H), 2.28 (m, 1H), 2.00 (m, 1H), 1.13 (d, J=6.8 Hz, 3H).

2-(1-Benzyl-4-methyl-pyrrolidin-3-yl)-7-pyridin-4-yl-3H-imidazo[5,1-f][1,2,4]triazin-4-one

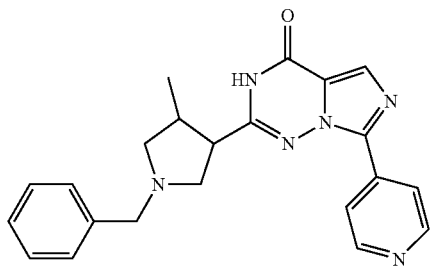 [SMILES: CC1CN(Cc2ccccc2)CC1c1nn2c(-c3ccncc3)ncc2c(=O)[nH]1]

20% yield. $^1$H NMR (400 MHz, CDCl$_3$): δ 8.72 (d, J=7.2 Hz, 2H), 8.29 (d, J=3.6 Hz, 2H), 8.01 (s, 1H), 7.39~7.31 (m, 5H), 3.87 (m, 1H), 3.65 (m, 1H), 3.49~3.43 (m, 1H), 3.08 (m, 1H), 2.88 (m, 1H), 2.53 (m, 1H), 2.24 (m, 2H), 1.27 (d, J=7.2 Hz, 3H).

2-(1-benzyl-4-methylpyrrolidin-3-yl)-7-(2,4-difluorophenyl)imidazo[1,5-f][1,2,4]triazin-4(3H)-one

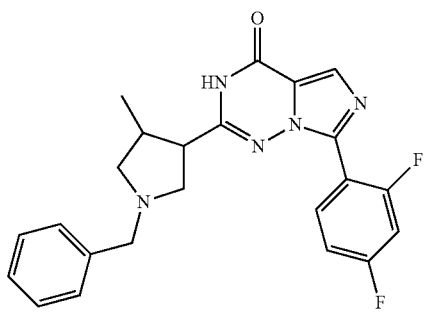 [SMILES: CC1CN(Cc2ccccc2)CC1c1nn2c(-c3ccc(F)cc3F)ncc2c(=O)[nH]1]

31% yield. LC-MS: m/z 422 [M+1]$^+$. $^1$H NMR (400 MHz, CDCl$_3$): δ 7.99 (s, 1H), 7.78~7.72 (m, 1H), 7.40~7.28 (m, 5H), 7.03~6.93 (m, 2H), 3.82 (d, J=12.4 Hz, 1H), 3.57 (d, J=12.4 Hz, 1H), 3.39 (t, J=8.4 Hz, 1H), 2.99 (d, J=10.0 Hz, 1H), 2.72~2.70 (m, 1H), 2.52~2.40 (m, 2H), 1.92 (dd, J=8.0, 9.2 Hz, 1H), 1.17 (d, J=6.8 Hz, 3H).

Part II (Azetidine Series)

Preparation of intermediates

2-Chloromethyl-7-(tetrahydro-pyran-4-yl)-3H-imidazo[5,1-f][1,2,4]triazin-4-one

Scheme 6

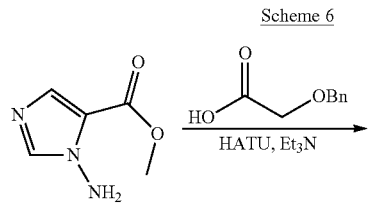

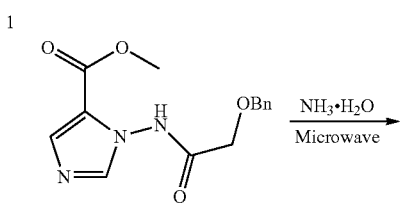

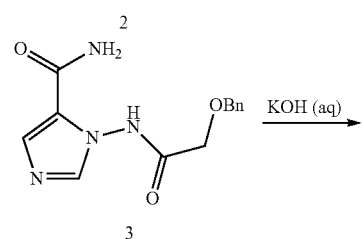

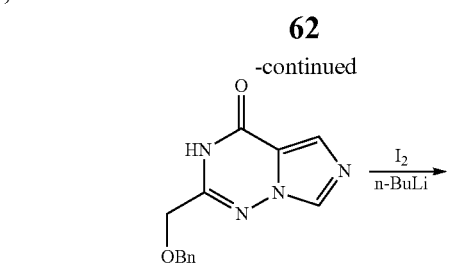

3-(2-Benzyloxy-acetylamino)-3H-imidazole-4-carboxylic acid methyl ester (2)

To a solution of compound 1 (5.0 g, 35.4 mmol), benzyloxy-acetic acid (6.5 g, 39.0 mmol) and DIEA (19 ml, 106.3 mmol) in DMF (50 mL) on an ice-water bath was added HATU (20.2 g, 53.1 mmol). The mixture was stirred at ambient temperature overnight. After removal of the solvent, the residue was purified by chromatography on silica gel column (eluted with PE/EtOAc=10:1 to 2:1) to afford compound 2 (8.7 g, 85% yield) as an oil. LC-MS: m/z 290.2 [M+H]+.

3-(2-Benzyloxy-acetylamino)-3H-imidazole-4-carboxylic acid amide (3)

Compound 2 (8.7 g, 30.1 mmol) and ammonium hydroxide (15 ml) were combined in a sealed tube and heated to 70° C. under microwave irradiation for 2 hours. The mixture was concentrated in vacuo to afford compound 3 (7.3 g, 88% yield) as a white solid. LC-MS: m/z 275.1 [M+H]+.

2-Benzyloxymethyl-3H-imidazo[5,1-f][1,2,4]triazin-4-one (4)

A solution of KOH (4.4 g, 78.5 mmol) in water (50 mL) was added dropwise to a solution of compound 3 (7.3 g, 26.6 mmol) in EtOH (60 mL) at room temperature. The resulting solution was heated to 110° C. for 3 hours. After removal of the organic solvent, the mixture was poured into ice water and the pH was adjusted to 7.0 with 1M aqueous HCl solution. The suspension was filtered and the filtrate was dried to afford compound 4 (4.9 g, 71% yield) as a white solid. $^1$H NMR (400 MHz, DMSO-d6): δ 12.05 (s, 1H), 8.45 (s, 1H), 7.74 (s, 1H), 7.39~7.29 (m, 5H), 4.59 (s, 2H), 4.36 (s, 2H). LC-MS: m/z 257.2 [M+H]+.

2-Benzyloxymethyl-7-iodo-3H-imidazo[5,1-f][1,2,4]triazin-4-one (5)

To a solution of compound 4 (4.9 g, 19.1 mmol) in THF (120 mL) was added n-BuLi (23 mL) dropwise at −78° C. and the resulting reaction mixture was stirred below −70° C. for one hour, followed by dropwise addition of iodine (19.4 g, 76.3 mmol) in THF (60 mL) at the same temperature. The reaction was allowed to warm to room temperature slowly. The reaction was quenched with saturated aqueous $Na_2SO_3$ solution (60 mL), and it was then extracted with EtOAc (60 mL×3). The organic phases were combined and dried over $Na_2SO_4$. The solid was filtered and the filtrate was concentrated in vacuo to give the crude product, which was purified by chromatography on silica gel column (eluted with PE/EtOAc=10:1 to 2:1) to afford compound 5 (4.1 g, 56% yield) as a white solid. $^1$H NMR (400 MHz, DMSO-d6): δ 12.16 (s, 1H), 7.84 (s, 1H), 7.42~7.29 (m, 5H), 4.62 (s, 2H), 4.40 (s, 2H). LC-MS: m/z 383.2 [M+H]+.

2-Benzyloxymethyl-7-(3,6-dihydro-2H-pyran-4-yl)-3H-imidazo[5,1-f][1,2,4]triazin-4-one (6)

To a solution of compound 5 (1.0 g, 2.61 mmol) in dioxane (12 mL) at room temperature was added dropwise a solution of $Cs_2CO_3$ (2.5 g, 7.66 mmol) in water (3 mL), followed by addition of Pd(PPh$_3$)$_4$ (300 mg, 0.26 mmol) and 4-(4,4,5,5-Tetramethyl-[1,3,2]dioxaborolan-2-yl)-3,6-dihydro-2H-pyran (636 mg, 3.0 mmol). The reaction mixture was degassed by purging with $N_2$ for 15 min. Then the mixture was heated to 125° C. under microwave irradiation for 40 min. After removal the solvent, the residue was purified by chromatography on silica gel column eluted with PE/EtOAc=10:1 to 1:5) to afford compound 6 (680 mg, 76% yield) as a white solid. LC-MS: m/z 339.1 [M+H]+.

2-Hydroxymethyl-7-(tetrahydro-pyran-4-yl)-3H-imidazo[5,1-f][1,2,4]triazin-4-one (7)

To a solution of compound 6 (650 mg, 1.14 mmol) in MeOH (30 mL) was added Pd(OH)$_2$/C (120 mg). The reaction mixture was stirred under 50 psi of hydrogen at 70° C. until LC-MS showed that the starting material was almost consumed. The suspension was filtered through celite and washed with MeOH (20 mL×2) and the filtrate was concentrated in vacuo to afford compound 7 (410 mg, 85% yield) as a white solid. LC-MS: m/z 251.3 [M+H]+.

2-Chloromethyl-7-(tetrahydro-pyran-4-yl)-3H-imidazo[5,1-f][1,2,4]triazin-4-one (8)

To a solution of compound 7 (400 mg, 1.6 mmol) in $CH_2Cl_2$ (50 mL) in ice-water bath was added $SOCl_2$ (10 mL) dropwise. The resulting mixture was then stirred at ambient temperature overnight. The reaction mixture was concentrated in vacuo to afford compound 8 (370 mg, 86% yield) as a white solid. LC-MS: m/z 269.1 [M+H]+. $^1$H NMR (400 MHz, DMSO-d6): δ 12.50 (s, 1H), 8.02 (s, 1H), 4.57 (s, 2H), 3.95 (m, 2H), 3.48 (m, 3H), 1.88 (m, 4H).

2-Acetyl-7-(tetrahydro-pyran-4-yl)-3H-imidazo[5,1-f][1,2,4]triazin-4-one

Scheme 7

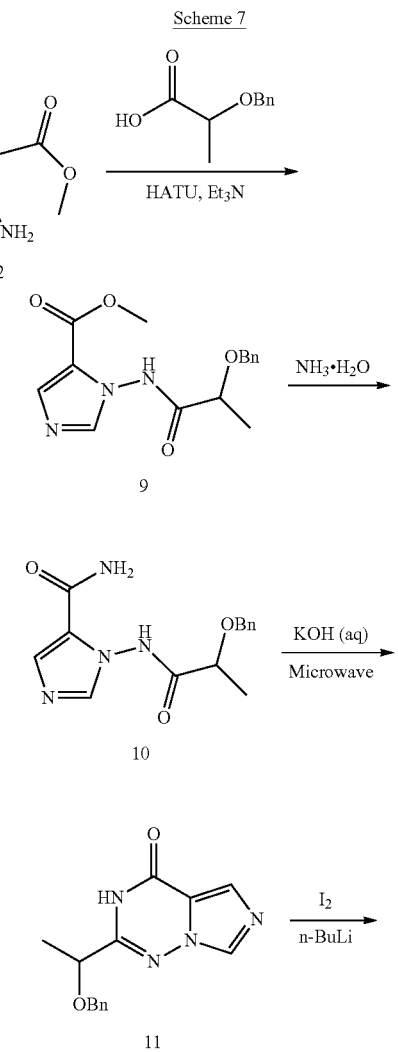

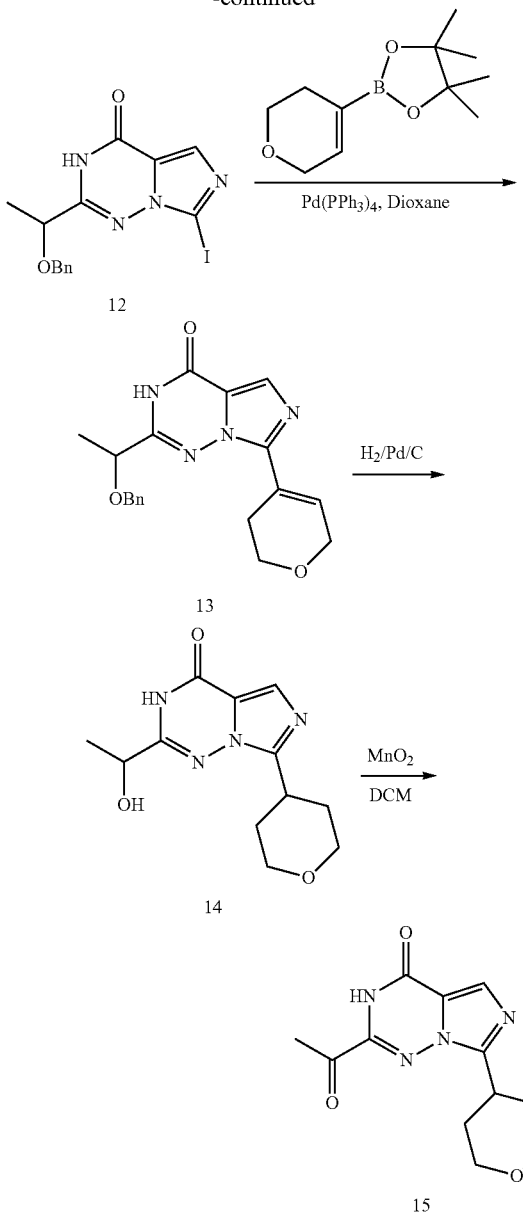

3-(2-Benzyloxy-propionylamino)-3H-imidazole-4-carboxylic acid methyl ester (9)

To a solution of compound 2 (4.2 g, 29.7 mmol), 2-Benzyloxy-propionic acid (5.5 g, 29.7 mmol) and DIEA (10 mL) in a mixture of DMF (1 mL) and THF (50 mL) in ice-water bath was added HATU (13.5 g, 35.7 mmol). The resulting mixture was then stirred at ambient temperature overnight. Water (100 mL) was added. The mixture was extracted with ethyl acetate (300 mL×2). The combined organic phases were concentrated to give a crude residue, which was purified by chromatography on silica gel column (eluted with PE/EtOAc=1:1 to 1:3) to afford compound 9 (8.2 g, 91% yield) as brown oil. LC-MS: m/z 304 [M+H]$^+$.

3-(2-Benzyloxy-propionylamino)-3H-imidazole-4-carboxylic acid amide (10)

Compound 9 (8.2 g, 27 mmol) and ammonium hydroxide (100 mL) were mixed and heated to 60° C. for two hours. The reaction mixture was concentrated in vacuo to give compound 10 (7.8 g, 100% yield) as white solid. LC-MS: m/z 289 [M+H]$^+$.

2-(1-Benzyloxy-ethyl)-3H-imidazo[5,1-f][1,2,4]triazin-4-one (11)

To a solution of compound 10 (1.5 g, 5.2 mmol) in EtOH (10 mL) was added a solution of KOH (870 mg, 15.6 mmol) in H$_2$O (4 mL). Then the resulting mixture was heated at 100° C. under microwave heating for one hour. After removal of the solvent, the mixture was poured into ice water and pH was adjusted to 7 with 1M aqueous HCl solution. The suspension was filtered and the solid was dried to give compound 11 (1.06 g, 75% yield) as a white solid. LC-MS: m/z 271 [M+H]$^+$. $^1$H NMR (400 MHz, CDCl$_3$): δ 8.70 (br. s, 1H), 8.10 (s, 1H), 7.92 (s, 1H), 7.39~7.32 (m, 5H), 4.60 (m, 2H), 4.46 (q, J=6.4 Hz, 1H), 1.57 (d, J=6.4 Hz, 3H).

2-(1-Benzyloxy-ethyl)-7-iodo-3H-imidazo[5,1-f][1,2,4]triazin-4-one (12)

To a solution of compound 11 (1.2 g, 4.4 mmol) in THF (100 mL) was added n-BuLi (2.5 M, 3.5 ml) dropwise at −78° C. over 30 minutes and the resulting reaction mixture was stirred below −70° C. for another one hour. Then a solution of iodine (2.2 g, 8.8 mmol) in THF (20 mL) was added dropwise and the dark brown mixture was allowed to warm up to room temperature slowly over one hour. The reaction was quenched with saturated aqueous solution of Na$_2$SO$_3$ (60 mL), and then the mixture was extracted with EtOAc (200 mL×2). The organic layers were combined and dried over Na$_2$SO$_4$, filtered and concentrated in vacuo to give the crude product, which was purified by chromatography on silica gel column (eluted with PE/EtOAc=10:1 to 2:1) to afford compound 12 (450 mg, 25% yield) as a yellow solid. LC-MS: m/z 397 [M+H]$^+$. $^1$H NMR (400 MHz, CDCl$_3$): δ 8.82 (br. s, 1H), 7.94 (s, 1H), 7.36~7.32 (m, 5H), 4.65~4.55 (m, 3H), 1.60 (d, J=6.4 Hz, 3H).

2-(1-Benzyloxy-ethyl)-7-(3,6-dihydro-2H-pyran-4-yl)-3H-imidazo[5,1-f][1,2,4]triazin-4-one (13)

To a solution of compound 12 (300 mg, 0.75 mmol) in dioxane (2 mL) was added a solution of Cs$_2$CO$_3$ (492 mg, 1.51 mmol) in H$_2$O (0.5 mL) dropwise, followed by addition of 4-(4,4,5,5-tetramethyl-[1,3,2]dioxaborolan-2-yl)-3,6-dihydro-2H-pyran (318 mg, 1.5 mmol) and Pd(PPh$_3$)$_4$ (86 mg, 0.075 mmol). The reaction mixture was degassed by purging with N$_2$ for 15 min. Then the reaction was heated to 125° C. under microwave heating for 40 min. After removal of the solvent, the residue was purified by chromatography on silica gel column (eluted with PE/EtOAc=10:1 to 1:5) to afford compound 13 (200 mg, 75% yield) as white solid. LC-MS: m/z 353 [M+H]$^+$. $^1$H NMR (400 MHz, CDCl$_3$): δ 8.82 (br. s, 1H), 7.91 (s, 1H), 7.37~7.32 (m, 5H), 7.19 (br. s, 1H), 4.61 (m, 2H), 4.49 (q, J=6.8 Hz, 1H), 4.40 (m, 2H), 3.95 (t, J=5.2 Hz, 2H), 2.78 (m, 2H), 1.58 (d, J=6.4 Hz, 3H).

2-(1-Hydroxy-ethyl)-7-(tetrahydro-pyran-4-yl)-3H-imidazo[5,1-f][1,2,4]triazin-4-one (14)

To a solution of compound 13 (900 mg, 2.55 mmol) in MeOH (30 mL) was added Pd(OH)$_2$/C (120 mg). The mixture was stirred at 75° C. under H₂ (50 psi) overnight. The suspension was filtered through Celite, washed with MeOH (20 mL×2). The combined organic phases were concentrated in vacuo to afford compound 14 (540 mg, 80% yield) as a white solid. LC-MS: m/z 265 [M+H]⁺. H NMR (400 MHz, CDCl₃): δ 9.07 (br. s, 1H), 7.85 (s, 1H), 4.84 (q, J=6.4 Hz, 1H), 4.11 (m, 2H), 3.59 (m, 2H), 3.44~3.39 (m, 1H), 2.14~2.06 (m, 3H), 1.92~1.88 (m, 2H), 1.64 (d, J=6.4 Hz, 3H).

2-Acetyl-7-(tetrahydro-pyran-4-yl)-3H-imidazo[5,1-f][1,2,4]triazin-4-one (15)

To a solution of compound 14 (400 mg, 1.6 mmol) in CH₂Cl₂ (50 mL) was added MnO₂ (520 mg, 6 mmol). The mixture was heated at 50° C. overnight. The reaction mixture was filtered and washed with ethyl acetate. The filtrate was concentrated in vacuo to afford compound 15 (370 mg, 86% yield) as a white solid. LC-MS: m/z 263 [M+H]⁺. ¹H NMR (300 MHz, CDCl₃): δ 8.99 (br. s, 1H), 7.93 (s, 1H), 4.16~4.12 (m, 2H), 3.67~3.59 (m, 2H), 3.54~3.48 (m, 1H), 2.72 (s, 3H), 2.19~2.11 (m, 2H), 2.00~1.96 (m, 2H).
PREPARATION of target compounds:

Example 4

2-[3-(4-Fluoro-phenoxy)-azetidin-1-ylmethyl]-7-(tetrahydro-pyran-4-yl)-3H-imidazo[5,1-f][1,2,4]triazin-4-one

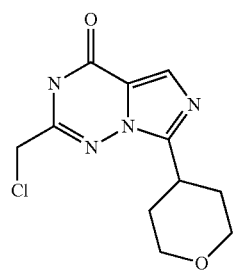

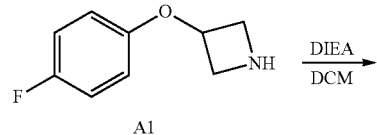

To a solution of compound 15 (40 mg, 0.15 mmol) and compound A1 (50 mg, 0.30 mmol) in CH₃CN (40 mL) was added DiEA (0.5 mL, 3.0 mmol). The resulting solution was heated to 70° C. for 2 h. The reaction was found to be complete by monitoring with TLC. The reaction was concentrated in vacuum. The residue was purified by column chromatography on silica gel (eluted with EtOAc/MeOH 100:1 to 30:1) to afford the desired product (25 mg, 42% yield) as a white solid. LC-MS: m/z 400.1 [M+1]⁺. ¹H NMR (400 MHz, CD₃OD-d4): δ 8.44 (br. s, 1H), 7.65 (s, 1H), 6.93 (m, 2H), 6.73 (m, 2H), 3.98~3.95 (m, 2H), 3.90~3.86 (m, 2H), 3.59 (s, 2H), 3.54~3.46 (m, 3H), 3.32 (m, 2H), 1.95~1.81 (m, 5H).

The following compounds were prepared in a similar way:

2-[3-(4-Methoxy-phenyl)-azetidin-1-ylmethyl]-7-(tetrahydro-pyran-4-yl)-3H-imidazo[5,1-f][1,2,4]triazin-4-one

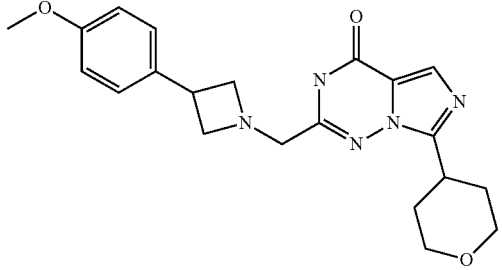 [SMILES: COc1ccc(C2CN(Cc3nn4c(C5CCOCC5)ncc4c(=O)[nH]3)C2)cc1]

31% yield. LC-MS: m/z 396.2 [M+1]⁺. 1H NMR (400 MHz, CDCl₃): δ 7.84 (s, 1H), 7.23~7.21 (d, J=8.4 Hz, 2H), 6.90~6.88 (d, J=8.4 Hz, 2H), 4.11~4.08 (m, 2H), 3.88~3.86 (m, 2H), 3.84 (s, 3H), 3.81~3.72 (m, 1H), 3.62 (s, 2H), 3.59~3.56 (m, 2H), 3.45~3.41 (m, 1H), 3.38~3.35 (m, 2H), 2.11~2.04 (m, 2H), 1.89~1.82 (m, 2H).

7-(4-Fluoro-phenyl)-2-[3-(4-methoxy-phenyl)-azetidin-1-ylmethyl]-3H-imidazo[5,1-f][1,2,4]triazin-4-one

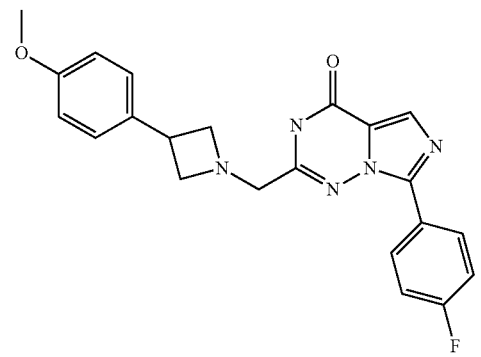 [SMILES: COc1ccc(C2CN(Cc3nn4c(-c5ccc(F)cc5)ncc4c(=O)[nH]3)C2)cc1]

20% yield. LC-MS: m/z 406.1[M+1]⁺. ¹H NMR (400 MHz, CD₃OD-d4): δ 8.38~8.34 (m, 2H), 7.91 (s, 1H), 7.32~7.29 (m, 4H), 6.92~6.90 (d, J=8.8 Hz, 2H), 3.97~3.94 (m, 2H), 3.82 (s, 3H), 3.80~3.77 (m, 1H), 3.75 (s, 2H), 3.51~3.47 (m, 2H).

7-(4-Fluoro-phenyl)-2-[3-(4-fluoro-phenyl)-azetidin-1-ylmethyl]-3H-imidazo[5,1-f][1,2,4]triazin-4-one

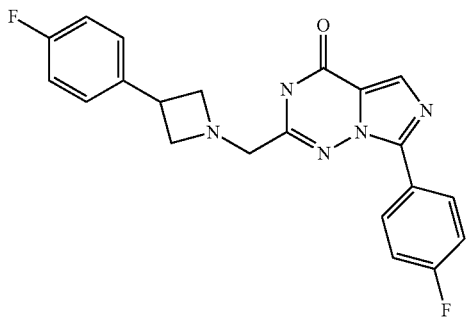 [SMILES: O=c1[nH]c(CN2CC(c3ccc(F)cc3)C2)nn2c(-c3ccc(F)cc3)ncc12]

14% yield. LC-MS: m/z 394.1[M+1]+. 1H NMR (400 MHz, CD3OD-d4): δ 8.19~8.16 (m, 2H), 7.94 (s, 1H), 7.46~7.42 (m, 2H), 7.33~7.29 (m, 2H), 7.17~7.13 (m, 2H), 4.73~4.65 (m, 2H), 4.61 (s, 2H), 4.50~4.45 (m, 2H), 4.36~4.29 (m, 1H).

2-[3-(4-Fluoro-phenyl)-azetidin-1-ylmethyl]-7-(tetrahydro-pyran-4-yl)-3H-imidazo[5,1-f][1,2,4]triazin-4-one

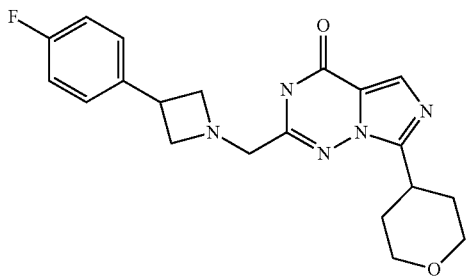

18 mg, 20% yield. LC-MS: m/z 384.1[M+1]+. 1H NMR (400 MHz, CD3OD-d4): δ 7.62 (s, 1H), 7.30~7.26 (m, 2H), 6.97~6.93 (m, 2H), 3.96~3.93 (m, 2H), 3.83~3.79 (m, 2H), 3.71~3.67 (m, 1H), 3.55 (s, 2H), 3.53~3.45 (m, 2H), 3.38 (m, 1H), 3.33~3.30 (m, 2H), 1.93~1.87 (m, 2H), 1.82~1.78 (m, 2H).

2-[3-(2,6-Difluoro-phenoxy)-azetidin-1-ylmethyl]-7-(tetrahydro-pyran-4-yl)-3H-imidazo[5,1-f][1,2,4]triazin-4-one

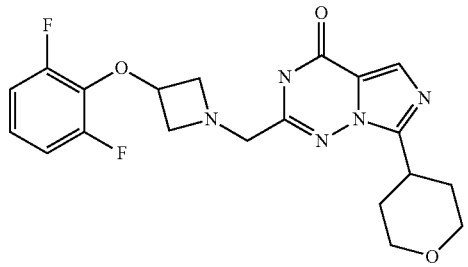 [SMILES: O=c1[nH]c(CN2CC(Oc3c(F)cccc3F)C2)nn2c(C3CCOCC3)ncc12]

36% yield. LC-MS: m/z 418.1 [M+1]+. 1H NMR (400 MHz, DMSO-d6): δ 12.20 (br. s, 1H), 7.70 (s, 1H), 7.23~7.19 (m, 3H), 5.08 (m, 1H), 4.70 (m, 2H), 4.56 (s, 2H), 4.52~4.48 (m, 2H), 3.97 (d, J=10.7 Hz, 2H), 3.52~3.40 (m, 3H), 1.85 (m, 4H).

7-(Tetrahydro-pyran-4-yl)-2-[3-(4-trifluoromethoxy-phenoxy)-azetidin-1-ylmethyl]-3H-imidazo[5,1-f][1,2,4]triazin-4-one

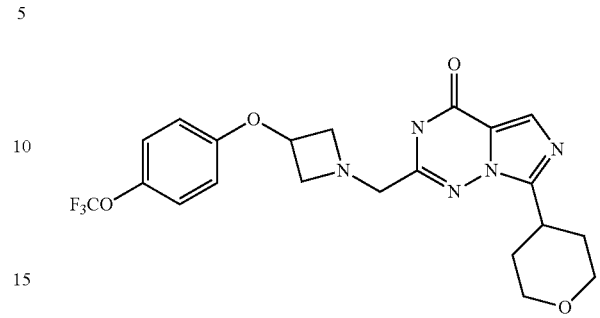

35% yield. LC-MS: m/z 466.1 [M+1]+. 1H NMR (400 MHz, CDCl3): δ 7.84 (s, 1H), 7.16~7.14 (d, J=8.8 Hz, 2H), 6.77~6.74 (d, J=8.8 Hz, 2H), 4.84~4.81 (m, 1H), 4.11~4.07 (m, 2H), 3.97~3.93 (m, 2H), 3.67 (s, 2H), 3.61~3.55 (m, 2H), 3.44~3.38 (m, 3H), 2.11~2.04 (m, 2H), 1.91~1.87 (m, 2H).

2-[3-(4-Dimethylamino-phenyl)-azetidin-1-ylmethyl]-7-(tetrahydro-pyran-4-yl)-3H-imidazo[5,1-f][1,2,4]triazin-4-one

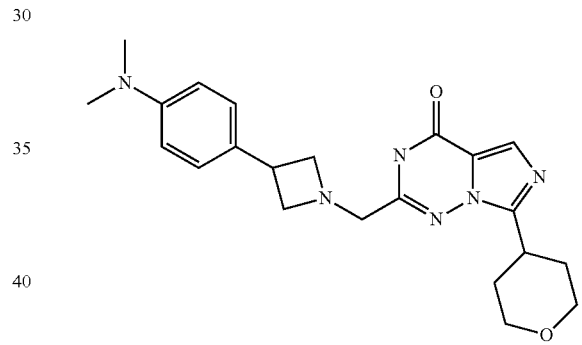

26% yield. LC-MS: m/z 409.2 [M+1]+. 1H NMR (400 MHz, CDCl3): δ 7.84 (s, 1H), 7.19~7.17 (d, J=8.8 Hz, 2H), 6.74~6.72 (d, J=8.8 Hz, 2H), 4.11~4.08 (m, 2H), 3.86~3.82 (m, 2H), 3.72~3.68 (m, 1H), 3.62~3.56 (m, 4H), 3.42~3.37 (m, 1H), 3.35~3.33 (m, 2H), 2.94 (s, 6H), 2.11~2.05 (m, 2H), 1.92~1.89 (m, 2H).

2-(3-Phenoxy-azetidin-1-ylmethyl)-7-(tetrahydro-pyran-4-yl)-3H-imidazo[5,1-f][1,2,4]triazin-4-one

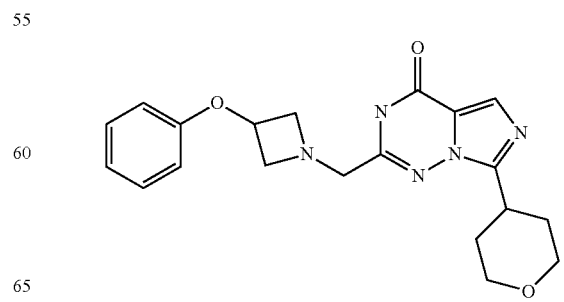

32% yield. LC-MS: m/z 382.1 [M+H]+. 1H NMR (400 MHz, DMSO-d6): δ 11.73 (br. s, 1H), 7.67 (s, 1H), 7.27 (m, 2H), 6.95 (m, 1H), 6.82 (m, 2H), 4.83 (m, 1H), 3.93~3.84 (m, 4H), 3.54 (s, 2H), 3.47 (m, 2H), 3.32 (m, 1H), 3.24 (m, 2H), 1.85 (m, 4H).

2-(3-Pyrimidin-2-yl-azetidin-1-ylmethyl)-7-(tetra-hydro-pyran-4-yl)-3H-imidazo[5,1-f][1,2,4]triazin-4-one

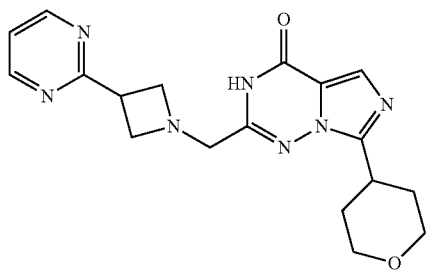 [SMILES: O=c1[nH]c(CN2CC(c3ncccn3)C2)nn2c(C3CCOCC3)ncc12]

12% yield. LC-MS: m/z=368.2 [M+1]+. 1H NMR (400 MHz, CD3OD-d6): δ 8.76~8.75 (m, 2H), 7.65~7.63 (m, 1H), 7.37~7.35 (m, 1H), 3.98~3.80 (m, 5H), 3.58~3.38 (m, 7H), 1.87~1.81 (m, 4H).

2-[3-(4-Methyl-benzyloxy)-azetidin-1-ylmethyl]-7-(tetrahydro-pyran-4-yl)-3H-imidazo[5,1-f][1,2,4]triazin-4-one

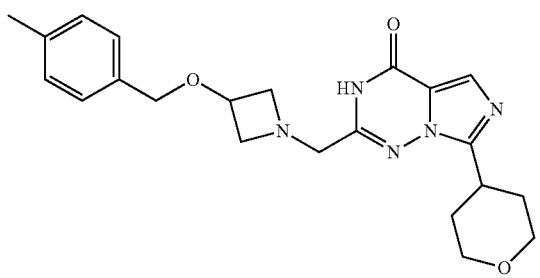 [SMILES: Cc1ccc(COC2CN(Cc3nn4c(C5CCOCC5)ncc4c(=O)[nH]3)C2)cc1]

9% yield. LC-MS: m/z=410.2 [M+1]+. 1H NMR (300 MHz, CD3OD-d4): δ 7.93 (s, 1H), 7.29 (d, J=8.1 Hz, 2H), 7.20 (d, J=8.1 Hz, 2H), 4.57~4.60 (m, 7H), 4.23~4.26 (m, 2H), 4.05~4.10 (m, 2H), 3.58~3.66 (m, 3H), 2.34 (s, 3H), 1.92~2.00 (m, 4H).

2-(3-Benzyl-azetidin-1-ylmethyl)-7-(tetrahydro-pyran-4-yl)-3H-imidazo[5,1-f][1,2,4]triazin-4-one

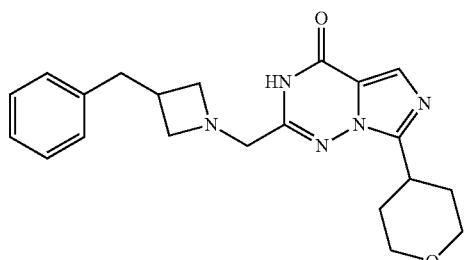

23% yield. LC-MS: m/z=380.2 [M+1]+. 1H NMR (400 MHz, CDCl3): δ 7.82 (s, 1H), 7.31~7.27 (m, 2H), 7.23~7.21 (m, 1H), 7.14~7.12 (m, 2H), 4.10~4.07 (m, 2H), 3.61~3.50 (m, 6H), 3.43~3.37 (m, 1H), 3.12~3.09 (m, 2H), 2.91~2.89 (m, 2H), 2.84~2.83 (m, 1H), 2.11~2.083 (m, 2H), 1.91~1.87 (m, 2H).

2-[3-(4-Methoxy-phenoxymethyl)-azetidin-1-yl methyl]-7-(tetrahydro-pyran-4-yl)-3H-imidazo[5,1-f][1,2,4]triazin-4-one

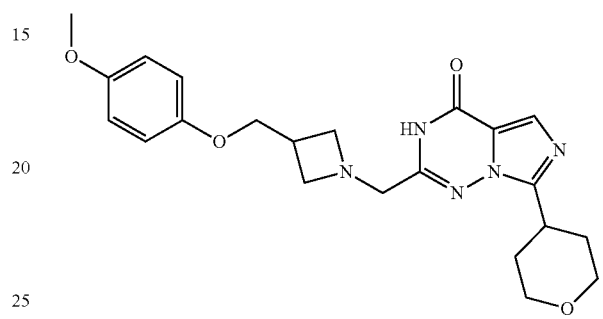

15% yield. LC-MS: m/z=426.2 [M+1]+. 1H NMR (400 MHz, CD3OD-d4): δ 7.84 (s, 1H), 7.04 (d, J=12.0 Hz, 2H), 6.92 (d, J=12.0 Hz, 2H), 4.62 (m, 4H), 4.46 (m, 2H), 4.13~4.15 (m, 2H), 4.02~4.07 (m, 2H), 3.78 (s, 3H), 3.54~3.60 (m, 3H), 3.37 (m, 1H), 1.89~2.06 (m, 4H).

2-[3-(4-Pyrrolidin-1-yl-phenyl)-azetidin-1-ylm-ethyl]-7-(tetrahydro-pyran-4-yl)-3H-imidazo[5,1-f][1,2,4]triazin-4-one

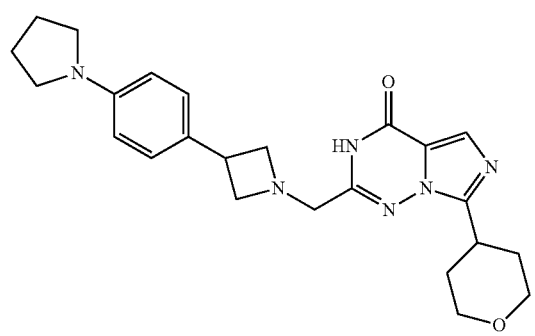 [SMILES: O=c1[nH]c(CN2CC(c3ccc(N4CCCC4)cc3)C2)nn2c(C3CCOCC3)ncc12]

23% yield. LC-MS: m/z=435.2 [M+1]+. 1H NMR (400 MHz, CDCl3): δ 7.84 (s, 1H), 7.16 (d, J=8.8 Hz, 2H), 6.55 (d, J=8.4 Hz, 2H), 4.11~4.08 (m, 2H), 3.86~3.84 (m, 2H), 3.71~3.67 (m, 1H), 3.62~3.56 (m, 4H), 3.45~3.39 (m, 1H), 3.36~3.33 (m, 2H), 3.29~3.26 (m, 4H), 2.17~2.10 (m, 2H), 2.08~1.99 (m, 4H), 1.92~1.89 (m, 2H).

Example 5

2-{1-[3-(4-Methoxy-phenyl)-azetidin-1-yl]-ethyl}-7-(tetrahydro-pyran-4-yl)-3H-imidazo[5,1-f][1,2,4]triazin-4-one

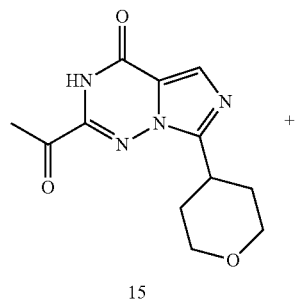

15

+

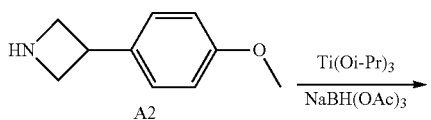

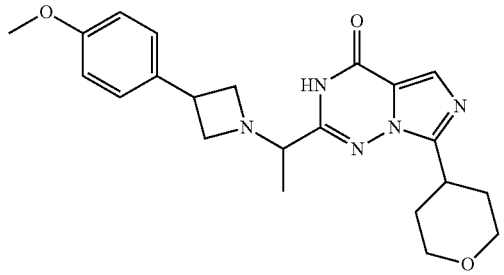

To a solution of compound 15 (57 mg, 0.21 mmol) and compound A2 (43 mg, 0.21 mmol) in THF (50 mL) was added Ti(Oi-Pr)$_3$ (1 mL). The mixture was then stirred at ambient temperature overnight. Then NaBH(OAc)$_3$ (200 mg, 0.95 mmol) was added and the reaction was stirred at room temperature overnight. The reaction mixture was poured into 10 ml of water and the pH of the solution was adjusted to 7 with a saturated aqueous solution of NaHCO$_3$. The reaction mixture was extracted with ethyl acetate (100 mL×2). The combined organic layers were dried over Na$_2$SO$_4$, and the solid was filtered off. The filtrate was concentrated in vacuo to give a crude residue which was subjected to Prep-HPLC to afford the desired compound (7 mg, 7.8% yield) as a white solid. LC-MS: m/z 410.2 [M+H]$^+$. $^1$H NMR (400 MHz, CD$_3$OD-d4): δ 7.63 (s, 1H), 7.18 (dd, J=2.0, 7.2 Hz, 2H), 6.80 (dd, J=2.0, 7.2 Hz, 2H), 3.98~3.95 (m, 2H), 3.83~3.73 (m, 2H), 3.68 (s, 3H), 3.67~3.63 (m, 1H), 3.56~3.47 (m, 1H), 3.32~3.22 (m, 2H), 1.96~1.80 (m, 4H), 1.31 (d, J=6.4 Hz, 3H).

The racemic mixture of 2-{1-[3-(4-Methoxy-phenyl)-azetidin-1-yl]-ethyl}-7-(tetrahydro-pyran-4-yl)-3H-imidazo[5,1-f][1,2,4]triazin-4-one was submitted for preparative chiral H PLC (Column=chiralpak IA; Mobile phase=n-Hexane/EtOH 70/30; Flow rate=12 mL/min; UV: 230 nm; 30 mg/inj in) and gave two enantiomers:

2-{1-[3-(4-Methoxy-phenyl)-azetidin-1-yl]-ethyl}-7-(tetrahydro-pyran-4-yl)-3H-imidazo[5,1-f][1,2,4]triazin-4-one

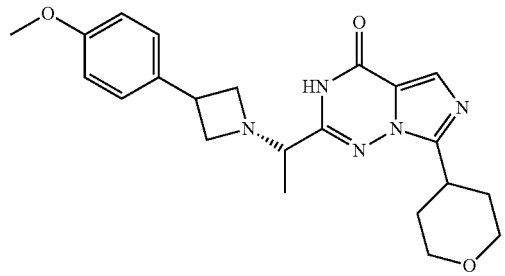

40% yield. Chiral analytical HPLC (Column=chiralpak IA; Mobile phase=n-Hexane/EtOH 70/30; Flow rate=1.0 mL/min): T$_R$=9.98. LC-MS (ESI) m/z=410.2 [M+1]$^+$. $^1$H NMR (400 MHz, CDCl$_3$): δ 7.84 (s, 1H), 7.21 (d, J=8.4 Hz, 2H), 6.88 (dd, J=1.6 Hz, J=6.4 Hz, 2H), 4.12~4.08 (m, 2H), 3.81 (s, 3H), 3.77~3.68 (m, 3H), 3.63~3.57 (m, 2H), 3.46~3.40 (m, 2H), 3.31~3.28 (m, 1H), 3.23~3.20 (m, 1H), 2.11~2.07 (m, 2H), 1.93~1.89 (m, 2H), 1.33 (d, J=6.4 Hz, 3H).

2-{1-[3-(4-Methoxy-phenyl)-azetidin-1-yl]-ethyl}-7-(tetrahydro-pyran-4-yl)-3H-imidazo[5,1-f][1,2,4]triazin-4-one

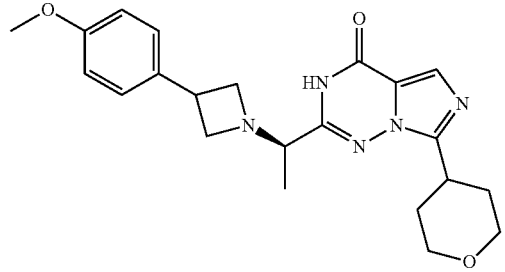 [SMILES: COc1ccc(C2CN([C@H](C)c3nn4c(C5CCOCC5)ncc4c(=O)[nH]3)C2)cc1]

40% yield. Chiral analytical HPLC (Column=chiralpak IA; Mobile phase=n-Hexane/EtOH 70/30; Flow rate=1.0 mL/min): T$_R$=14.7. LC-MS (ESI) m/z=410.2 [M+1]$^+$. $^1$H NMR (400 MHz, CDCl$_3$): δ 7.84 (s, 1H), 7.21 (d, J=8.4 Hz, 2H), 6.88 (d, J=8.8 Hz, 2H), 4.12~4.08 (m, 2H), 3.80 (s, 3H), 3.77~3.74 (m, 1H), 3.72~3.68 (m, 2H), 3.62~3.57 (m, 2H), 3.46~3.40 (m, 2H), 3.31~3.28 (m, 1H), 3.23~3.20 (m, 1H), 2.11~2.07 (m, 2H), 1.93~1.90 (m, 2H), 1.32 (d, J=6.8 Hz, 3H).

The following compound was prepared in a similar way:

2-{1-[3-(4-Fluoro-phenyl)-azetidin-1-yl]-ethyl}-7-(tetrahydro-pyran-4-yl)-3H-imidazo[5,1-f][1,2,4]triazin-4-one

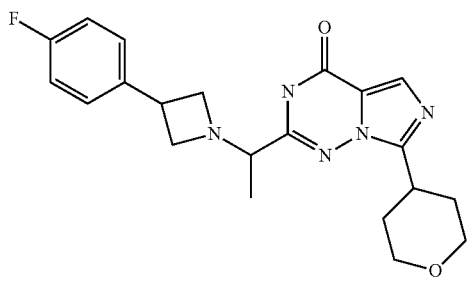 [SMILES: CC(c1nn2c(C3CCOCC3)ncc2c(=O)[nH]1)N1CC(c2ccc(F)cc2)C1]

15% yield. LC-MS: m/z 398.2 [M+H]$^+$. $^1$H NMR (400 MHz, MeOD-d4): δ 7.85 (s, 1H), 7.26~7.23 (m, 2H), 7.05~7.01 (m, 2H), 4.12~4.09 (m, 2H), 3.80~3.72 (m, 3H), 3.63~3.57 (m, 2H), 3.47~3.40 (m, 2H), 3.33~3.29 (m, 1H), 3.25~3.22 (m, 1H), 2.12~2.06 (m, 2H), 1.93~1.90 (m, 2H), 1.31 (d, J=7.2 Hz, 3H).

2-{1-[3-(4-Fluoro-phenoxy)-azetidin-1-yl]-ethyl}-7-(tetrahydro-pyran-4-yl)-3H-imidazo[5,1-f][1,2,4]triazin-4-one

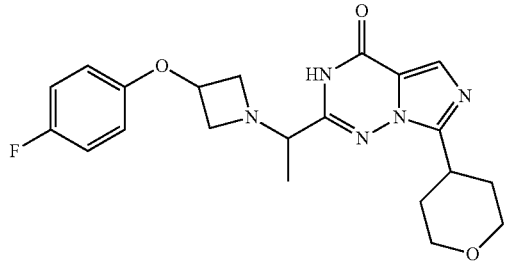 [SMILES: CC(c1nn2c(C3CCOCC3)ncc2c(=O)[nH]1)N1CC(Oc2ccc(F)cc2)C1]

10% yield. LC-MS: (ESI) m/z=414.1 [M+1]$^+$. $^1$H NMR (400 MHz, CDCl$_3$): δ 7.83 (s, 1H), 6.99~6.94 (m, 2H), 6.71~6.69 (m, 2H), 4.77~4.74 (m, 1H), 4.10~4.08 (m, 2H), 3.86~3.77 (m, 2H), 3.61~3.56 (m, 2H), 3.49~3.46 (m, 1H), 3.42~3.33 (m, 2H), 3.25~3.21 (m, 1H), 2.11~2.04 (m, 2H), 1.92~1.88 (m, 2H), 1.34 (d, J=6.4 Hz, 3H).

7-(Tetrahydro-pyran-4-yl)-2-[1-(3-p-tolyloxy-azetidin-1-yl)-ethyl]-3H-imidazo[5,1-f][1,2,4]triazin-4-one

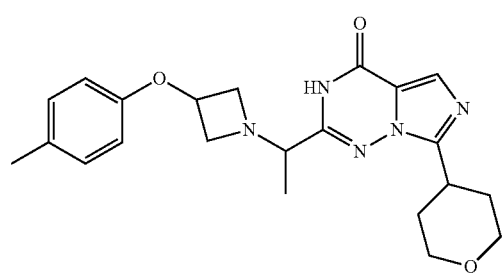 [SMILES: Cc1ccc(OC2CN(C(C)c3nn4c(C5CCOCC5)ncc4c(=O)[nH]3)C2)cc1]

35% yield. LC-MS: m/z=410 [M+1]$^+$. $^1$H NMR (300 MHz, CDCl$_3$): δ 7.84 (s, 1H), 7.07 (d, J=8.4 Hz, 2H), 7.07 (d, J=8.4 Hz, 2H), 4.80~4.76 (m, 1H), 4.12~4.07 (m, 2H), 3.87~3.77 (m, 2H), 3.63~3.55 (m, 2H), 3.49~3.32 (m, 3H), 3.24~3.20 (m, 1H), 2.28 (s, 3H), 2.11~2.06 (m, 2H), 1.93~1.88 (m, 2H), 1.33 (d, J=6.9 Hz, 3H).

2-[1-(3-Phenyl-azetidin-1-yl)-ethyl]-7-(tetrahydro-pyran-4-yl)-3H-imidazo[5,1-f][1,2,4]triazin-4-one

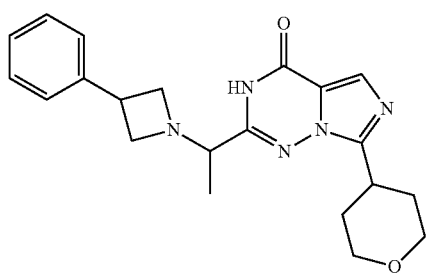 [SMILES: CC(c1nn2c(C3CCOCC3)ncc2c(=O)[nH]1)N1CC(c2ccccc2)C1]

62% yield. LC-MS: m/z=380.1 [M+1]$^+$. $^1$H NMR (400 MHz, CDCl$_3$): δ 7.84 (s, 1H), 7.37~7.33 (m, 2H), 7.29~7.24 (m, 3H), 4.11~4.09 (m, 2H), 3.80~3.73 (m, 3H), 3.63~3.57 (m, 2H), 3.47~3.40 (m, 2H), 3.37~3.34 (m, 1H), 3.30~3.25 (m, 1H), 2.16~2.05 (m, 2H), 1.93~1.90 (m, 2H), 1.33 (d, J=6.8 Hz, 3H).

2-{1-[3-(3-Fluoro-4-methoxy-phenyl)-azetidin-1-yl]-ethyl}-7-(tetrahydro-pyran-4-yl)-3H-imidazo[5,1-f][1,2,4]triazin-4-one

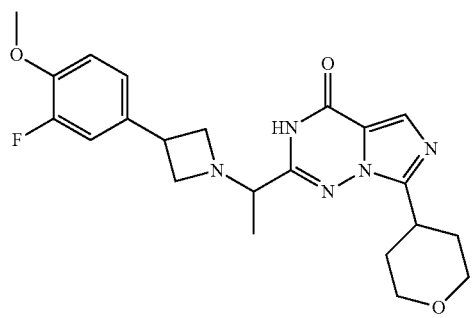 [SMILES: COc1ccc(C2CN(C(C)c3nn4c(C5CCOCC5)ncc4c(=O)[nH]3)C2)cc1F]

25% yield. LC-MS: m/z=428.2 [M+1]$^+$. $^1$H NMR (400 MHz, CDCl$_3$): δ 7.84 (s, 1H), 7.04~6.90 (m, 3H), 4.11~4.09 (m, 2H), 3.89 (s, 3H), 3.76~3.57 (m, 5H), 3.46~3.40 (m, 2H), 3.29~3.26 (m, 1H), 3.22~3.19 (m, 1H), 2.11~2.04 (m, 2H), 1.93~1.90 (m, 2H), 1.33 (d, J=6.8 Hz, 3H).

2-{1-[3-(2-Fluoro-4-methoxy-phenyl)-azetidin-1-yl]-ethyl}-7-(tetrahydro-pyran-4-yl)-3H-imidazo[5,1-f][1,2,4]triazin-4-one

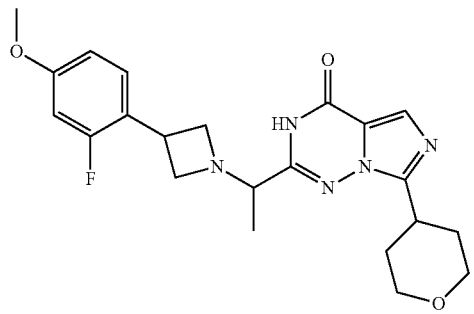 [SMILES: COc1ccc(C2CN(C(C)c3nn4c(C5CCOCC5)ncc4c(=O)[nH]3)C2)c(F)c1]

36% yield. LC-MS: m/z=428.2 [M+1]$^+$. $^1$H NMR (400 MHz, CDCl$_3$): δ 7.84 (s, 1H), 7.16 (dd, J=8.8 Hz, J=8.8 Hz, 1H), 6.68 (dd, J=2.4 Hz, J=6.8 Hz, 1H), 6.59 (dd, J=2.4 Hz, J=12.0 Hz, 1H), 4.11~4.08 (m, 2H), 3.88~3.81 (m, 2H), 3.79 (s, 3H), 3.75~3.72 (m, 1H), 3.62~3.57 (m, 2H), 3.46~3.39 (m, 2H), 3.36~3.33 (m, 1H), 3.27~3.23 (m, 1H), 2.14~2.04 (m, 2H), 1.93~1.90 (m, 2H), 1.32 (d, J=6.4 Hz, 3H).

2-{1-[3-(4-Ethoxy-phenyl)-azetidin-1-yl]-ethyl}-7-(tetrahydro-pyran-4-yl)-3H-imidazo[5,1-f][1,2,4]triazin-4-one

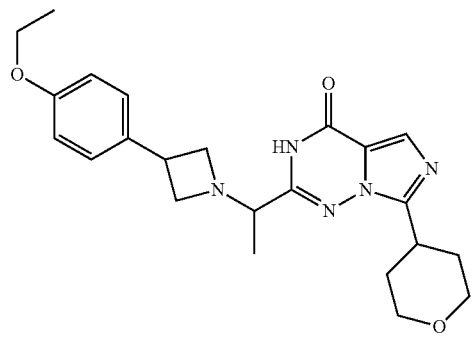 [SMILES: CCOc1ccc(C2CN(C(C)c3nn4c(C5CCOCC5)ncc4c(=O)[nH]3)C2)cc1]

18% yield. LC-MS: m/z=424.2 [M+1]$^+$. $^1$H NMR (400 MHz, CDCl$_3$): δ 7.84 (s, 1H), 7.19 (d, J=8.8 Hz, 2H), 6.87 (d, J=8.4 Hz, 2H), 4.11~4.09 (m, 2H), 4.05~4.00 (m, 2H), 3.78~3.66 (m, 3H), 3.63~3.57 (m, 2H), 3.46~3.40 (m, 2H), 3.32~3.29 (m, 1H), 3.24~3.20 (m, 1H), 2.11~2.05 (m, 2H), 1.93~1.90 (m, 2H), 1.41 (t, J=6.8 Hz, 3H), 1.32 (d, J=6.4 Hz, 3H).

2-{1-[3-(4-Hydroxy-phenyl)-azetidin-1-yl]-ethyl}-7-(tetrahydro-pyran-4-yl)-3H-imidazo[5,1-f][1,2,4]triazin-4-one

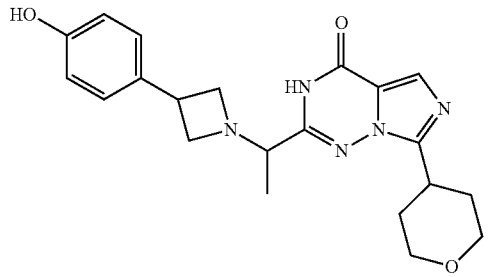 [SMILES: CC(c1nn2c(C3CCOCC3)ncc2c(=O)[nH]1)N1CC(c2ccc(O)cc2)C1]

10% yield. LC-MS (ESI): m/z=396.2 [M+1]$^+$. $^1$H NMR (400 MHz, CD$_3$OD-d4): δ 7.91 (s, 1H), 7.27 (d, J=11.2 Hz, 2H), 6.84 (d, J=11.2 Hz, 2H), 4.72~4.65 (m, 3H), 4.44~4.41 (m, 2H), 4.22~4.19 (m, 1H), 4.11~4.06 (m, 2H), 3.69~3.60 (m, 3H), 2.05~1.92 (m, 4H), 1.70 (d, J=8.8 Hz, 3H).

2-{1-[3-(4-Pyrrolidin-1-yl-phenyl)-azetidin-1-yl]-ethyl}-7-(tetrahydro-pyran-4-yl)-4a,7-dihydro-3H-imidazo[5,1-f][1,2,4]triazin-4-one

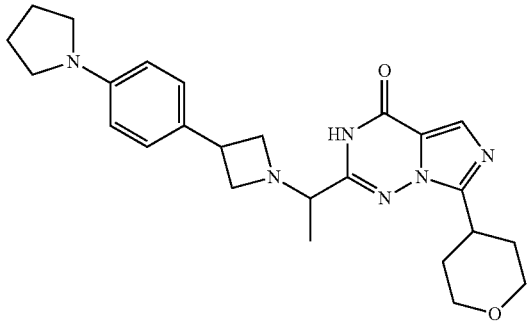 [SMILES: CC(c1nn2c(C3CCOCC3)ncc2c(=O)[nH]1)N1CC(c2ccc(N3CCCC3)cc2)C1]

28% yield. LC-MS: m/z=449.2 [M+1]$^+$. $^1$H NMR (400 MHz, CDCl$_3$): δ 7.84 (s, 1H), 7.15 (d, J=8.4 Hz, 2H), 6.54 (d, J=8.4 Hz, 2H), 4.11~4.08 (m, 2H), 3.74~3.57 (m, 5H), 3.46~3.40 (m, 2H), 3.27~3.25 (m, 5H), 3.20~3.17 (m, 1H), 2.11~2.08 (m, 2H), 2.05~2.00 (m, 4H), 1.93~1.90 (m, 2H), 1.32 (d, J=6.8 Hz, 3H).

2-{1-[3-(4-Dimethylamino-phenyl)-azetidin-1-yl]-ethyl}-7-(tetrahydro-pyran-4-yl)-3H-imidazo[5,1-f][1,2,4]triazin-4-one

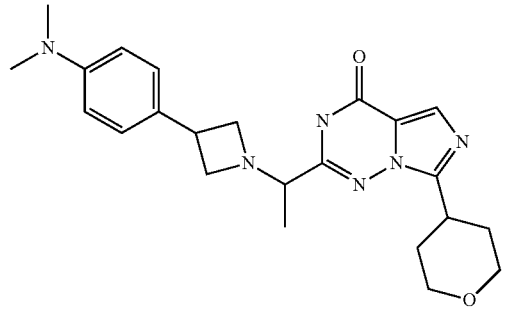 [SMILES: CC(c1nn2c(C3CCOCC3)ncc2c(=O)[nH]1)N1CC(c2ccc(N(C)C)cc2)C1]

23% yield. LC-MS: m/z=423.2 [M+1]$^+$. $^1$H NMR (400 MHz, CDCl$_3$): δ 7.83 (s, 1H), 7.16 (d, J=8.4 Hz, 2H), 6.72 (d, J=8.4 Hz, 2H), 4.11~4.08 (m, 2H), 3.74~3.69 (m, 1H), 3.68~3.57 (m, 4H), 3.45~3.40 (m, 2H), 3.30~3.27 (m, 1H), 3.21~3.17 (m, 1H), 2.94 (s, 6H), 2.11~2.08 (m, 2H), 1.93~1.90 (m, 2H), 1.32 (d, J=6.8 Hz, 3H).

7-(Tetrahydro-pyran-4-yl)-2-{1-[3-(4-trifluoromethoxy-phenyl)-azetidin-1-yl]-ethyl}-3H-imidazo[5,1-f][1,2,4]triazin-4-one

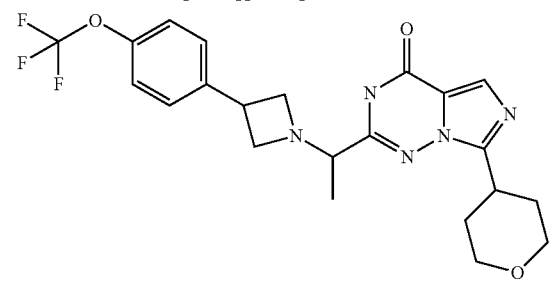

36% yield. LC-MS: m/z=464.2 [M+1]$^+$. $^1$H NMR (400 MHz, CDCl$_3$): δ 8.92 (br. s, 1H), 7.84 (s, 1H), 7.30 (d, J=8.4 Hz, 2H), 7.19 (d, J=8.0 Hz, 2H), 4.11~4.08 (m, 2H), 3.81~3.72 (m, 3H), 3.62~3.57 (m, 2H), 3.47~3.40 (m, 2H), 3.34~3.31 (m, 1H), 3.29~3.26 (m, 1H), 2.14~2.04 (m, 2H), 1.93~1.89 (m, 2H), 1.29 (d, J=8.8 Hz, 3H).

2-{1-[3-(4-Methoxy-benzyl)-azetidin-1-yl]-ethyl}-7-(tetrahydro-pyran-4-yl)-3H-imidazo[5,1-f][1,2,4]triazin-4-one

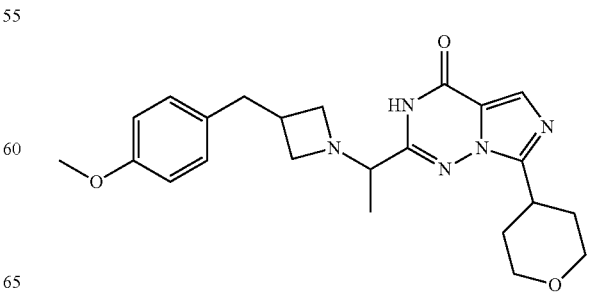

18% yield. LC-MS: m/z=424.2 [M+1]+. 1H NMR (400 MHz, CD3OD-d4): δ 7.59 (s, 1H), 6.98 (d, J=8.4 Hz, 2H), 6.72 (d, J=8.4 Hz, 2H), 3.97~3.94 (m, 2H), 3.65 (s, 3H), 3.54~3.43 (m, 6H), 3.10~3.07 (m, 2H), 2.72 (m, 3H), 1.94~1.88 (m, 2H), 1.85~1.77 (m, 2H), 1.25 (d, J=6.8 Hz, 3H).

2-{1-[3-(3-Chloro-4-methoxy-phenyl)-azetidin-1-yl]-ethyl}-7-(tetrahydro-pyran-4-yl)-3H-imidazo[5,1-f][1,2,4]triazin-4-one

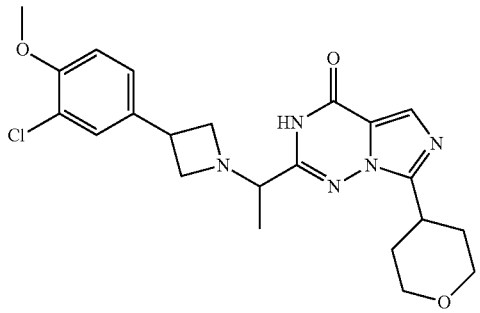 [SMILES: COc1ccc(C2CN(C(C)c3nn4c(C5CCOCC5)ncc4c(=O)[nH]3)C2)cc1Cl]

26% yield. LC-MS: m/z=444.1 [M+1]+. 1H NMR (400 MHz, CDCl3): δ 7.84 (s, 1H), 7.29 (s, 1H), 7.13 (d, J=8.0 Hz, 1H), 6.89 (d, J=8.0 Hz, 1H), 4.12~4.09 (m, 2H), 3.94 (s, 3H), 3.76~3.57 (m, 5H), 3.45~3.43 (m, 2H), 3.28 (t, J=6.4 Hz, 1H), 3.21 (t, J=6.4 Hz, 1H), 2.17~2.05 (m, 2H), 1.93~1.90 (m, 2H), 1.33 (d, J=6.4 Hz, 3H).

2-{1-[3-(3,4-Dimethoxy-phenyl)-azetidin-1-yl]-ethyl}-7-(tetrahydro-pyran-4-yl)-3H-imidazo[5,1-f][1,2,4]triazin-4-one

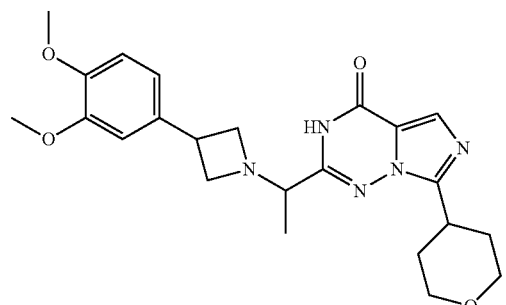

18% yield. LC-MS: m/z=440.2 [M+1]+. 1H NMR (400 MHz, CDCl3): δ 7.84 (s, 1H), 6.85 (m, 2H), 6.74 (s, 1H), 4.12~4.09 (m, 2H), 3.90 (s, 3H), 3.88 (s, 3H), 3.80~3.68 (m, 3H), 3.63~3.57 (m, 2H), 3.49~3.41 (m, 2H), 3.32 (t, J=6.4 Hz, 1H), 3.23 (t, J=6.0 Hz, 1H), 2.13~2.06 (m, 2H), 1.93~1.90 (m, 2H), 1.34 (d, J=6.4 Hz, 3H).

2-{1-[3-(4-Fluoro-3-methoxy-phenyl)-azetidin-1-yl]-ethyl}-7-(tetrahydro-pyran-4-yl)-3H-imidazo[5,1-f][1,2,4]triazin-4-one

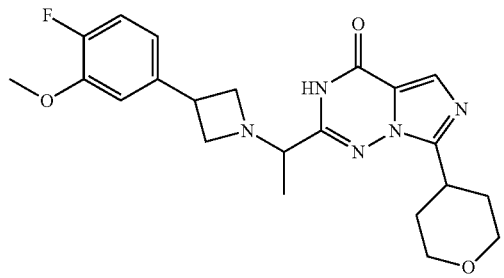 [SMILES: COc1cc(C2CN(C(C)c3nn4c(C5CCOCC5)ncc4c(=O)[nH]3)C2)ccc1F]

15% yield. LC-MS: m/z=428.2 [M+1]+. 1H NMR (300 MHz, CDCl3): δ 7.85 (s, 1H), 7.06 (dd, J=8.4 Hz, J=10.5 Hz, 1H), 6.85~6.81 (m, 2H), 4.14~4.09 (m, 2H), 3.92 (s, 3H), 3.81~3.71 (m, 3H), 3.65~3.57 (m, 2H), 3.47~3.42 (m, 2H), 3.35~3.33 (m, 1H), 3.24 (m, 1H), 2.14~2.10 (m, 2H), 1.95~1.90 (m, 2H), 1.35 (d, J=6.6 Hz, 3H).

2-{1-[3-(3,5-Difluoro-4-methoxy-phenyl)-azetidin-1-yl]-ethyl}-7-(tetrahydro-pyran-4-yl)-3H-imidazo[5,1-f][1,2,4]triazin-4-one

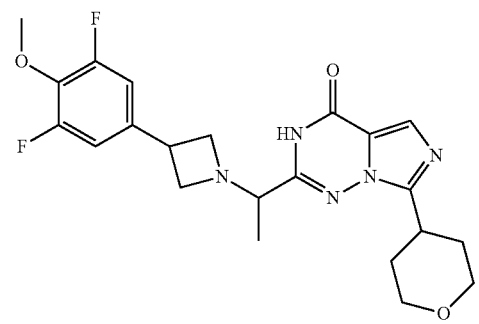 [SMILES: COc1c(F)cc(C2CN(C(C)c3nn4c(C5CCOCC5)ncc4c(=O)[nH]3)C2)cc1F]

15% yield. LC-MS: m/z=446.2 [M+1]+. 1H NMR (400 MHz, CDCl3): δ 7.85 (s, 1H), 6.86~6.83 (m, 2H), 4.13~4.09 (m, 2H), 3.99 (s, 3H), 3.77~3.71 (m, 2H), 3.67~3.57 (m, 3H), 3.48~3.41 (m, 2H), 3.29~3.20 (m, 2H), 2.13~2.08 (m, 2H), 1.95~1.90 (m, 2H), 1.34 (d, J=8.8 Hz, 3H).

2-{1-[3-(3-Methoxy-phenyl)-azetidin-1-yl]-ethyl}-7-(tetrahydro-pyran-4-yl)-3H-imidazo[5,1-f][1,2,4]triazin-4-one

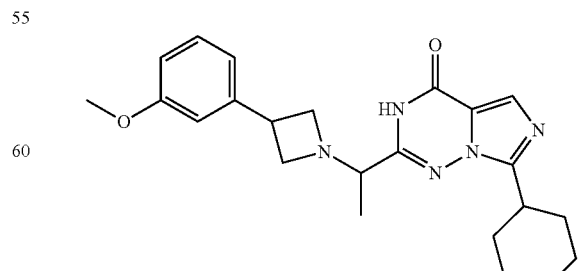

5% yield. LC-MS: m/z=410.2 [M+1]+. 1H NMR (400 MHz, CDCl3): δ 7.84 (s, 1H), 7.13 (s, 1H), 6.86 (d, J=7.6 Hz, 1H), 6.82~6.89 (m, 2H), 4.11~4.09 (m, 2H), 3.82 (s, 3H), 3.79~3.70 (m, 2H), 3.63~3.57 (m, 2H), 3.46~3.40 (m, 2H), 3.36~3.34 (m, 1H), 3.33~3.26 (m, 1H), 2.23 (s, 1H), 2.12~2.05 (m, 2H), 1.93~1.90 (m, 2H), 1.33 (d, J=6.4 Hz, 3H).

2-{1-[3-(4-Methoxy-3-methyl-phenyl)-azetidin-1-yl]-ethyl}-7-(tetrahydro-pyran-4-yl)-3H-imidazo[5,1-f][1,2,4]triazin-4-one

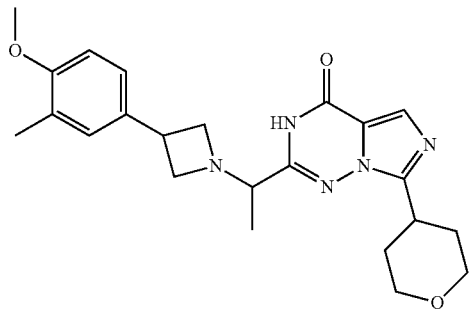 [SMILES: COc1ccc(C2CN(C(C)c3nn4c(C5CCOCC5)ncc4c(=O)[nH]3)C2)cc1C]

21% yield. LC-MS: m/z=424.2 [M+1]+. 1H NMR (300 MHz, CDCl3): δ 7.85 (s, 1H), 7.09~7.06 (m, 2H), 6.80 (d, J=7.8 Hz, 1H), 4.14~4.09 (m, 2H), 3.84 (s, 3H), 3.78~3.67 (m, 3H), 3.66~3.57 (m, 2H), 3.49~3.42 (m, 2H), 3.34~3.29 (m, 1H), 3.24~3.22 (m, 1H), 2.24 (s, 3H), 2.14~2.08 (m, 2H), 1.96~1.91 (m, 2H), 1.34 (d, J=6.6 Hz, 3H).

2-[1-(3-Benzo[1,3]dioxol-5-yl-azetidin-1-yl)-ethyl]-7-(tetrahydro-pyran-4-yl)-3H-imidazo[5,1-f][1,2,4]triazin-4-one

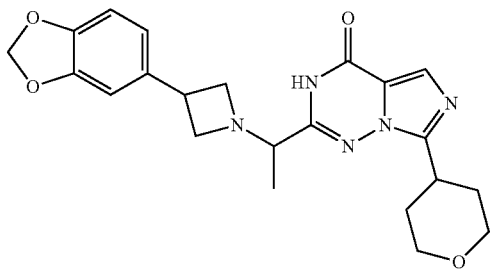 [SMILES: CC(c1nn2c(C3CCOCC3)ncc2c(=O)[nH]1)N1CC(c2ccc3c(c2)OCO3)C1]

10% yield. LC-MS: m/z=424.2 [M+1]+. 1H NMR (300 MHz, CDCl3): δ 7.85 (s, 1H), 6.81~6.70 (m, 3H), 5.97 (s, 2H), 4.14~4.10 (m, 2H), 3.77~3.70 (m, 3H), 3.68~3.58 (m, 2H), 3.49~3.41 (m, 2H), 3.29 (t, J=6.6 Hz, 1H), 3.22 (t, J=6.0 Hz, 1H), 2.13~2.09 (m, 2H), 1.95~1.91 (m, 2H), 1.34 (d, J=6.6 Hz, 3H).

2-{1-[3-(4-Methoxy-phenyl)-pyrrolidin-1-yl]-ethyl}-7-(tetrahydro-pyran-4-yl)-3H-imidazo[5,1-f][1,2,4]triazin-4-one

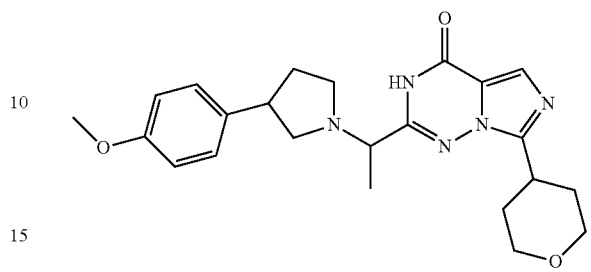

6% yield. LC-MS: m/z=424.2 [M+1]+. 1H NMR (400 MHz, CDCl3): δ 7.84 (s, 1H), 7.17~7.15 (d, J=7.6 Hz, 2H), 6.87~6.84 (dd, J=2.4, 8.4 Hz, 2H), 4.11~4.08 (m, 2H), 3.79 (s, 3H), 3.62~3.42 (m, 3H), 3.33~3.39 (m, 2H), 3.11~3.04 (m, 1H), 2.90~2.78 (m, 2H), 2.62~2.57 (m, 1H), 2.35~2.31 (m, 1H), 2.11~2.04 (m, 2H), 1.93~1.90 (m, 3H), 1.25 (d, J=6.6 Hz, 3H).

In Vitro Testing

PDE9 Inhibition Assay

A PDE9 assay may for example, be performed as follows: The assay is performed in 60 uL samples containing a fixed amount of the relevant PDE enzyme (sufficient to convert 20~25% of the cyclic nucleotide substrate), a buffer (50 mM HEPES7.6; 10 mM MgCl2; 0.02% Tween20), 0.1 mg/ml BSA, 225 pCi of 3H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and IC50 values can be calculated using the XLfit extension to EXCEL.

In the context of the present invention the assay was performed in 60 uL assay buffer (50 mM HEPES pH 7.6; 10 mM MgCl2; 0.02% Tween20) containing enough PDE9 to convert 20-25% of 10 nM 3H-cAMP and varying amounts of inhibitors. Following a 1 hour incubation the reactions were terminated by addition of 15 uL 8 mg/mL yttrium silicate SPA beads (Amersham). The beads were allowed to settle for one hr in the dark before the plates were counted in a Wallac 1450 Microbeta counter. IC50 values were calculated by non linear regression using XLfit (IDBS).

Results of the experiments showed that the tested compounds of the invention inhibit the PDE9 enzyme with IC50 values below 250 nM.

The invention claimed is:

1. A method of treating a subject suffering from a neurodegenerative disorder selected from the group consisting of Alzheimer's disease, mental retardation, cognitive impairments associated with schizophrenia (CIAS), attention-deficit/hyperactivity disorder, age-related cognitive decline, and substance-induced psychotic disorder; wherein said method comprises administering to said subject a therapeutically effective amount of a pharmaceutical composition comprising:

(A) a compound having the structure (I):

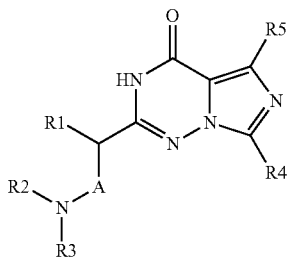

or a tautomer or pharmaceutically acceptable acid addition salt of said compound;
wherein R2 is cyclized with either R1 or R3,
wherein R1, R2 and R3 are:
R1, when cyclized with R2, is:

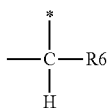

wherein R6 is selected from the group consisting of H, —CH$_3$, —C$_2$H$_5$, and —C$_3$H$_7$,
wherein * denotes the cyclization point, and
R1, when not cyclized, is selected from the group consisting of:
H and

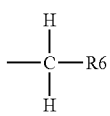

wherein R6 is selected from the group consisting of H, —CH$_3$, —C$_2$H$_5$, and —C$_3$H$_7$;
R2 is selected from the group consisting of:

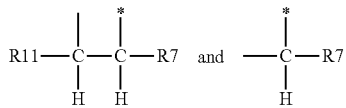

wherein R7 and R11 independently are selected from the group consisting of H, —CH$_3$, —C$_2$H$_5$, and —C$_3$H$_7$;
wherein * denotes the cyclization point; and
R3, when cyclized with R2, is:

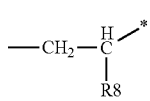

wherein * denotes the cyclization point, and
wherein R8 is selected from the group consisting of H, C$_1$-C$_6$ alkyl, branched C$_3$-C$_6$ alkyl, C$_3$-C$_6$ cycloalkyl, C$_6$-C$_{10}$ aryl, substituted C$_6$-C$_{10}$ aryl, C$_3$-C$_9$ heteroaryl, substituted C$_3$-C$_9$ heteroaryl, C$_1$-C$_6$ alkoxy, branched C$_3$-C$_6$ alkoxy, C$_3$-C$_6$ cycloalkoxy, C$_6$-C$_{10}$ aryloxy, substituted C$_6$-C$_{10}$ aryloxy, C$_3$-C$_9$ heteroaryloxy, and substituted C$_3$-C$_9$ heteroaryloxy; and
R3, when not cyclized, is:

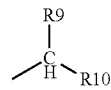

wherein:
R9 is selected from the group consisting of H, —CH$_3$, and —C$_2$H$_5$; and
R10 is selected from the group consisting of C$_6$-C$_{10}$ aryl, substituted C$_6$-C$_{10}$ aryl, C$_3$-C$_9$ heteroaryl, and substituted C$_3$-C$_9$ heteroaryl;
R4 is selected from the group consisting of C$_6$-C$_{10}$ aryl, substituted C$_6$-C$_{10}$ aryl, C$_3$-C$_9$ heteroaryl, substituted C$_3$-C$_9$ heteroaryl, C$_3$-C$_6$ heterocyclyl, substituted C$_3$-C$_6$ heterocyclyl, C$_3$-C$_6$ cycloalkyl, and substituted C$_3$-C$_6$ cycloalkyl;
R5 is selected from the group consisting of hydrogen, F, Cl, CN, —CH$_3$, —C$_2$H$_5$, —C$_3$H$_7$, and —CF$_3$;
A is absent;
and
(B) one or more pharmaceutically acceptable carriers, diluents or excipients.

2. The method of claim 1, wherein the neurodegenerative disorder is a substance-induced psychotic disorder and said substance-induced psychotic disorder is psychosis induced by: alcohol, an amphetamine, cannabis, cocaine, a hallucinogen, an inhalant, an opioid, or phencyclidine.

3. The method of claim 1, wherein the one or more heteroaryls of R4, R8 and R10 independently of each other comprise one or two nitrogen.

4. The method of claim 1, wherein said method comprises administering to said subject a therapeutically effective amount of a pharmaceutical composition comprising a compound, or a tautomer or pharmaceutically acceptable acid addition salt thereof; wherein said compound is selected from the group consisting of:
(14) 2-[[3-(4-methoxyphenyl)azetidin-1-yl]methyl]-7-tetrahydropyran-4-yl-3H-imidazo[5,1-f][1,2,4]triazin-4-one;
(15) 7-(4-fluorophenyl)-2-[[3-(4-methoxyphenyl)azetidin-1-yl]methyl]-3H-imidazo[5,1-f][1,2,4]triazin-4-one;
(16) 7-(4-fluorophenyl)-2-[[3-(4-fluorophenyl)azetidin-1-yl]methyl]-3H-imidazo[5,1-f][1,2,4]triazin-4-one;
(19) 2-[[3-(4-fluorophenyl) azetidin-1-yl]methyl]-7-tetrahydropyran-4-yl-3H-imidazo[5,1-f][1,2,4]triazin-4-one;
(32) 2-[[3-(2,6-difluorophenoxy)azetidin-1-yl]methyl]-7-tetrahydropyran-4-yl-3H-imidazo[5,1-f][1,2,4]triazin-4-one;
(33) 7-tetrahydropyran-4-yl-2-[[3-[4-(trifluoromethoxy)phenoxy]azetidin-1-yl]methyl]-3H-imidazo[5,1-f][1,2,4]triazin-4-one;
(34) 2-[[3-(4-dimethylaminophenyl)azetidin-1-yl]methyl]-7-tetrahydropyran-4-yl-3H-imidazo[5,1-f][1,2,4]triazin-4-one;
(37) 2-[(3-phenoxyazetidin-1-yl)methyl]-7-tetrahydropyran-4-yl-3H-imidazo[5,1-f][1,2,4]triazin-4-one;

(38) 2-[1-[3-(4-methoxyphenyl)azetidin-1-yl]ethyl]-7-tetrahydropyran-4-yl-3H-imidazo[5,1-f][1,2,4]triazin-4-one;
(41) 2-[1-[3-(4-fluorophenyl)azetidin-1-yl]ethyl]-7-tetrahydropyran-4-yl-3H-imidazo[5,1-f][1,2,4]triazin-4-one;
(42) 2-[(3-phenylazetidin-1-yl)methyl]-7-tetrahydropyran-4-yl-3H-imidazo[5,1-f][1,2,4]triazin-4-one;
(43) 2-[[3-(4-methylphenoxy)azetidin-1-yl]methyl]-7-tetrahydropyran-4-yl-3H-imidazo[5,1-f][1,2,4]triazin-4-one;
(46) 2-[[3-(2-pyridyl)azetidin-1-yl]methyl]-7-tetrahydropyran-4-yl-3H-imidazo[5,1-f][1,2,4]triazin-4-one;
(47) 2-[[3-(4-isopropylphenoxy)azetidin-1-yl]methyl]-7-tetrahydropyran-4-yl-3H-imidazo[5,1-f][1,2,4]triazin-4-one;
(53) 7-tetrahydropyran-4-yl-2-[[3-[5-(trifluoromethyl)-2-pyridyl]azetidin-1-yl]methyl]-3H-imidazo[5,1-f][1,2,4]triazin-4-one;
(54) 2-[[3-(3-pyridyloxy)azetidin-1-yl]methyl]-7-tetrahydropyran-4-yl-3H-imidazo[5,1-f][1,2,4]triazin-4-one;
(56) 2-[(1R)-1-[3-(4-methoxyphenyl)azetidin-1-yl]ethyl]-7-tetrahydropyran-4-yl-3H-imidazo[5,1-f][1,2,4]triazin-4-one;
(57) 2-[1-[3-(4-fluorophenoxy)azetidin-1-yl]ethyl]-7-tetrahydropyran-4-yl-3H-imidazo[5,1-f][1,2,4]triazin-4-one;
(62) 2-[1-[3-(4-hydroxyphenyl)azetidin-1-yl]ethyl]-7-tetrahydropyran-4-yl-3H-imidazo[5,1-f][1,2,4]triazin-4-one;
(63) 2-[1-[3-(4-methylphenoxy)azetidin-1-yl]ethyl]-7-tetrahydropyran-4-yl-3H-imidazo[5,1-f][1,2,4]triazin-4-one;
(64) 2-[(3-pyrimidin-2-ylazetidin-1-yl)methyl]-7-tetrahydropyran-4-yl-3H-imidazo[5,1-f][1,2,4]triazin-4-one;
(65) 2-[1-[3-(4-pyrrolidin-1-ylphenyl)azetidin-1-yl]ethyl]-7-tetrahydropyran-4-yl-3H-imidazo[5,1-f][1,2,4]triazin-4-one;
(66) 2-[[3-(5-pyrrolidin-1-ylpyrimidin-2-yl)azetidin-1-yl]methyl]-7-tetrahydropyran-4-yl-3H-imidazo[5,1-f][1,2,4]triazin-4-one;
(67) 2-[1-[3-(4-dimethylaminophenyl)azetidin-1-yl]ethyl]-7-tetrahydropyran-4-yl-3H-imidazo[5,1-f][1,2,4]triazin-4-one;
(68) 2-[1-(3-phenylazetidin-1-yl)ethyl]-7-tetrahydropyran-4-yl-3H-imidazo[5,1-f][1,2,4]triazin-4-one;
(69) 2-[1-[3-(3-fluoro-4-methoxy-phenyl)azetidin-1-yl]ethyl]-7-tetrahydropyran-4-yl-3H-imidazo[5,1-f][1,2,4]triazin-4-one;
(70) 2-[1-[3-(2-fluoro-4-methoxy-phenyl)azetidin-1-yl]ethyl]-7-tetrahydropyran-4-yl-3H-imidazo[5,1-f][1,2,4]triazin-4-one;
(71) 2-[1-[3-(4-ethoxyphenyl)azetidin-1-yl]ethyl]-7-tetrahydropyran-4-yl-3H-imidazo[5,1-f][1,2,4]triazin-4-one; and
(72) 7-tetrahydropyran-4-yl-2-[1-[3-[4-(trifluoromethoxy)phenyl]azetidin-1-yl]ethyl]-3H-imidazo[5,1-f][1,2,4]triazin-4-one.

5. A method of treating a subject suffering from a neurodegenerative disorder selected from the group consisting of Alzheimer's disease, mental retardation, cognitive impairments associated with schizophrenia (CIAS), attention-deficit/hyperactivity disorder, age-related cognitive decline, and substance-induced psychotic disorder; wherein said method comprises administering to said subject a therapeutically effective amount of a pharmaceutical composition comprising:

(A) a compound, or a tautomer or pharmaceutically acceptable acid addition salt thereof; wherein said compound is selected from the group consisting of:
(1) 2-(benzyloxymethyl)-7-tetrahydropyran-4-yl-3H-imidazo[5,1-f][1,2,4]triazin-4-one;
(2) 2-[1-(cyclohexylmethyl)-4-methyl-pyrrolidin-3-yl]-7-tetrahydropyran-4-yl-3H-imidazo[5,1-f][1,2,4]triazin-4-one;
(3) 2-(1-ethyl-4-methyl-pyrrolidin-3-yl)-7-tetrahydropyran-4-yl-3H-imidazo[5,1-f][1,2,4]triazin-4-one;
(4) 2-(1-benzyl-4-methoxy-pyrrolidin-3-yl)-7-tetrahydropyran-4-yl-3H-imidazo[5,1-f][1,2,4]triazin-4-one;
(5) 2-[1-[(4-fluorophenyl)methyl]-4-methoxy-pyrrolidin-3-yl]-7-tetrahydropyran-4-yl-3H-imidazo[5,1-f][1,2,4]triazin-4-one;
(6) 2-[4-methoxy-1-(p-tolylmethyl)pyrrolidin-3-yl]-7-tetrahydropyran-4-yl-3H-imidazo[5,1-f][1,2,4]triazin-4-one;
(7) 2-[[3-(p-tolylmethoxy)azetidin-1-yl]methyl]-7-tetrahydropyran-4-yl-3H-imidazo[5,1-f][1,2,4]triazin-4-one;
(8) 2-[(3-benzylazetidin-1-yl)methyl]-7-tetrahydropyran-4-yl-3H-imidazo[5,1-f][1,2,4]triazin-4-one;
(9) 2-[(3S,4S)-1-benzyl-4-methoxy-pyrrolidin-3-yl]-7-tetrahydropyran-4-yl-3H-imidazo[5,1-f][1,2,4]triazin-4-one;
(10) 2-[1-benzyl-4-(trifluoromethyl)pyrrolidin-3-yl]-7-tetrahydropyran-4-yl-3H-imidazo[5,1-f][1,2,4]triazin-4-one;
(11) 2-[4-methoxy-1-[(4-methoxyphenyl)methyl]pyrrolidin-3-yl]-7-tetrahydropyran-4-yl-3H-imidazo[5,1-f][1,2,4]triazin-4-one; and
(12) 2-[1-[3-[(4-methoxyphenyl)methyl]azetidin-1-yl]ethyl]-7-tetrahydropyran-4-yl-3H-imidazo[5,1-f][1,2,4]triazin-4-one; and
(B) one or more pharmaceutically acceptable carriers, diluents or excipients.

6. A method of treating a subject suffering from a substance-induced psychotic disorder and said substance-induced psychotic disorder is psychosis induced by: alcohol, an amphetamine, cannabis, cocaine, a hallucinogen, an inhalant, an opioid, or phencyclidine, wherein said method comprises administering to said subject a therapeutically effective amount of a pharmaceutical composition comprising:

(A) a compound, or a tautomer or pharmaceutically acceptable acid addition salt thereof; wherein said compound is selected from the group consisting of:
(1) 2-(benzyloxymethyl)-7-tetrahydropyran-4-yl-3H-imidazo[5,1-f][1,2,4]triazin-4-one;
(2) 2-[1-(cyclohexylmethyl)-4-methyl-pyrrolidin-3-yl]-7-tetrahydropyran-4-yl-3H-imidazo[5,1-f][1,2,4]triazin-4-one;
(3) 2-(1-ethyl-4-methyl-pyrrolidin-3-yl)-7-tetrahydropyran-4-yl-3H-imidazo[5,1-f][1,2,4]triazin-4-one;
(4) 2-(1-benzyl-4-methoxy-pyrrolidin-3-yl)-7-tetrahydropyran-4-yl-3H-imidazo[5,1-f][1,2,4]triazin-4-one;
(5) 2-[1-[(4-fluorophenyl)methyl]-4-methoxy-pyrrolidin-3-yl]-7-tetrahydropyran-4-yl-3H-imidazo[5,1-f][1,2,4]triazin-4-one;
(6) 2-[4-ethoxy-1-(p-tolylmethyl)pyrrolidin-3-yl]-7-tetrahydropyran-4-yl-3H-imidazo[5,1-f][1,2,4]triazin-4-one;

(7) 2-[[3-(p-tolylmethoxy)azetidin-1-yl]methyl]-7-tetrahydropyran-4-yl-3H-imidazo[5,1-f][1,2,4]triazin-4-one;

(8) 2-[(3-benzylazetidin-1-yl)methyl]-7-tetrahydropyran-4-yl-3H-imidazo[5,1-f][1,2,4]triazin-4-one;

(9) 2-[(3S,4S)-1-benzyl-4-methoxy-pyrrolidin-3-yl]-'7-tetrahydropyran-4-yl-3H-imidazo[5,1-f][1,2,4]triazin-4-one;

(10) 2-[1-benzyl-4-(trifluoromethyl)pyrrolidin-3-yl]-7-tetrahydropyran-4-yl-3H-imidazo[5,1-f][1,2,4]triazin-4-one;

(11) 2-[4-methoxy-1-[(4-methoxyphenyl)methyl]pyrrolidin-3-yl]-'7-tetrahydropyran-4-yl-3H-imidazo[5,1-f][1,2,4]triazin-4-one; and

(12) 2-[1-[3-[(4-methoxyphenyl)methyl]azetidin-1-yl]ethyl]-7-tetrahydropyran-4-yl-3H-imidazo[5,1-f][1,2,4]triazin-4-one; and (B) one or more pharmaceutically acceptable carriers, diluents or excipients.

7. A method of treating a subject suffering from a neurodegenerative disorder selected from the group consisting of Alzheimer's disease, mental retardation, cognitive impairments associated with schizophrenia (CIAS), attention-deficit/hyperactivity disorder, age-related cognitive decline, and substance-induced psychotic disorder; wherein said method comprises administering to said subject a therapeutically effective amount of a pharmaceutical composition comprising:

2-[[3-[(4-fluorophenyl)methoxy]azetidin-1-yl]methyl]-7-tetrahydropyran-4-yl-3H-imidazo[5,1-f][1,2,4]triazin-4-one, or a tautomer or pharmaceutically acceptable acid addition salt thereof.

8. The method of claim 7, wherein the neurodegenerative disorder is a substance-induced psychotic disorder and said substance-induced psychotic disorder is psychosis induced by: alcohol, an amphetamine, cannabis, cocaine, a hallucinogen, an inhalant, an opioid, or phencyclidine.

9. A method of treating a subject suffering from a substance-induced psychotic disorder and said substance-induced psychotic disorder is psychosis induced by: alcohol, an amphetamine, cannabis, cocaine, a hallucinogen, an inhalant, an opioid, or phencyclidine, wherein said method comprises administering to said subject a therapeutically effective amount of a pharmaceutical composition comprising:

(A) a compound having the structure (I):

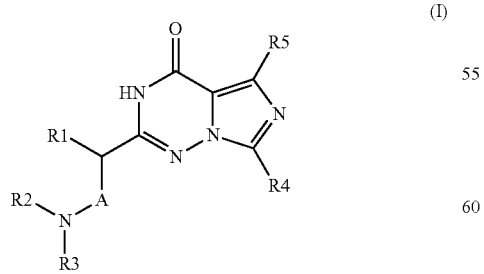

(I)

or a tautomer or pharmaceutically acceptable acid addition salt of said compound;
wherein R2 is cyclized with either R1 or R3, wherein R1, R2 and R3 are:
R1, when cyclized with R2, is:

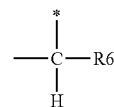

wherein R6 is selected from the group consisting of H, —CH₃, —C₂H₅, and —C₃H₇,
wherein * denotes the cyclization point, and
R1, when not cyclized, is selected from the group consisting of:
H and

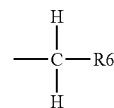

wherein R6 is selected from the group consisting of H, —CH₃, —C₂H₅, and —C₃H₇;
R2 is selected from the group consisting of:

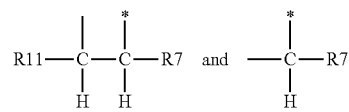

wherein R7 and R11 independently are selected from the group consisting of H, —CH₃, —C₂H₅, and —C₃H₇;
wherein * denotes the cyclization point; and
R3, when cyclized with R2, is:

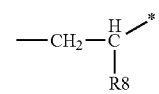

wherein * denotes the cyclization point, and
wherein R8 is selected from the group consisting of H, C₁-C₆ alkyl, branched C₃-C₆ alkyl, C₃-C₆ cycloalkyl, C₆-C₁₀ aryl, substituted C₆-C₁₀ aryl, C₃-C₉ heteroaryl, substituted C₃-C₉ heteroaryl, C₁-C₆ alkoxy, branched C₃-C₆ alkoxy, C₃-C₆ cycloalkoxy, C₆-C₁₀ aryloxy, substituted C₆-C₁₀ aryloxy, C₃-C₉ heteroaryloxy, and substituted C₃-C₉ heteroaryloxy; and
R3, when not cyclized, is:

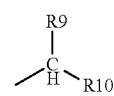

wherein:
R9 is selected from the group consisting of H, —CH₃, and —C₂H₅; and
R10 is selected from the group consisting of C₆-C₁₀ aryl, substituted C₆-C₁₀ aryl, C₃-C₉ heteroaryl, and substituted C₃-C₉ heteroaryl;

R4 is selected from the group consisting of $C_6$-$C_{10}$ aryl, substituted $C_6$-$C_{10}$ aryl, $C_3$-$C_9$ heteroaryl, substituted $C_3$-$C_9$ heteroaryl, $C_3$-$C_6$ heterocyclyl, substituted $C_3$-$C_6$ heterocyclyl, $C_3$-$C_6$ cycloalkyl, and substituted $C_3$-$C_6$ cycloalkyl;

R5 is selected from the group consisting of hydrogen, F, Cl, CN, —$CH_3$, —$C_2H_5$, —$C_3H_7$, and —$CF_3$;

A is absent or —$CH_2$—;

provided that the compound is not:
(1) 2-[4-methyl-1-(2-pyridylmethyl)pyrrolidin-3-yl]-7-tetrahydropyran-4-yl-3H-imidazo[5,1-f][1,2,4]triazin-4-one;
(2) 2-[1-[(4-fluorophenyl)methyl]-4-methyl-pyrrolidin-3-yl]-7-tetrahydropyran-4-yl-3H-imidazo[5,1-f][1,2,4]triazin-4-one;
(3) 2-(1-benzyl-4-methyl-pyrrolidin-3-yl)-7-tetrahydropyran-4-yl-3H-imidazo[5,1-f][1,2,4]triazin-4-one;
(4) 2-[4-methyl-1-(pyrimidin-2-ylmethyl)pyrrolidin-3-yl]-7-tetrahydropyran-4-yl-3H-imidazo[5,1-f][1,2,4]triazin-4-one;
(5) 2-[1-[(6-methoxy-2-pyridyl)methyl]-4-methyl-pyrrolidin-3-yl]-7-tetrahydropyran-4-yl-3H-imidazo[5,1-f][1,2,4]triazin-4-one;
(6) 2-[(3S,4S)-1-benzyl-4-methyl-pyrrolidin-3-yl]-7-tetrahydropyran-4-yl-3H-imidazo[5,1-f][1,2,4]triazin-4-one;
(7) 2-[(3R,4R)-1-benzyl-4-methyl-pyrrolidin-3-yl]-7-tetrahydropyran-4-yl-3H-imidazo[5,1-f][1,2,4]triazin-4-one;
(8) 2-[(3R,4R)-4-methyl-1-(pyrimidin-2-ylmethyl)pyrrolidin-3-yl]-7-tetrahydropyran-4-yl-3H-imidazo[5,1-f][1,2,4]triazin-4-one;
(9) 4-[3-methyl-4-(4-oxo-7-tetrahydropyran-4-yl-3H-imidazo[5,1-f][1,2,4]triazin-2-yl)pyrrolidin-1-yl]benzonitrile;
(10) 2-[(3S,4S)-1-[(4-fluorophenyl)methyl]-4-methyl-pyrrolidin-3-yl]-7-tetrahydropyran-4-yl-3H-imidazo[5,1-f][1,2,4]triazin-4-one;
(11) 2-[(3R,4R)-1-[(4-fluorophenyl)methyl]-4-methyl-pyrrolidin-3-yl]-7-tetrahydropyran-4-yl-3H-imidazo[5,1-f][1,2,4]triazin-4-one; or
(12) 2-[4-methyl-1-(pyrazin-2-ylmethyl)pyrrolidin-3-yl]-7-tetrahydropyran-4-yl-3H-imidazo[5,1-f][1,2,4]triazin-4-one;

and (B) one or more pharmaceutically acceptable carriers, diluents or excipients.

\* \* \* \* \*